(12) United States Patent
Nallani et al.

(10) Patent No.: US 12,239,736 B2
(45) Date of Patent: Mar. 4, 2025

(54) POLYMERSOMES COMPRISING A SOLUBLE ENCAPSULATED ANTIGEN AS WELL AS METHODS OF MAKING AND USES THEREOF

(71) Applicant: ACM BIOLABS PTE LTD, Singapore (SG)

(72) Inventors: Madhavan Nallani, Singapore (SG); Fabien Decaillot, Singapore (SG); Thomas Andrew Cornell, Singapore (SG); Amit Kumar Khan, Singapore (SG)

(73) Assignee: ACM BIOLABS PTE LTD, Singapore (SG)

( * ) Notice: Subject to any disclaimer, the term of this patent is extended or adjusted under 35 U.S.C. 154(b) by 277 days.

(21) Appl. No.: 16/964,931

(22) PCT Filed: Jan. 25, 2019

(86) PCT No.: PCT/EP2019/051853
§ 371 (c)(1),
(2) Date: Jul. 24, 2020

(87) PCT Pub. No.: WO2019/145475
PCT Pub. Date: Aug. 1, 2019

(65) Prior Publication Data
US 2021/0251899 A1    Aug. 19, 2021

(30) Foreign Application Priority Data
Jan. 25, 2018    (EP) .................................. 18153348

(51) Int. Cl.
*A61K 39/00*    (2006.01)
*A61K 9/127*    (2006.01)
*A61K 9/1273*    (2025.01)

(52) U.S. Cl.
CPC ........ *A61K 9/1273* (2013.01); *A61K 39/0011* (2013.01); *A61K 2039/552* (2013.01);
(Continued)

(58) Field of Classification Search
CPC .............. A61K 9/1273; A61K 39/0011; A61K 2039/552; A61K 2039/55555; A61K 2039/572; A61K 39/39
See application file for complete search history.

(56) References Cited

FOREIGN PATENT DOCUMENTS

| CN | 104936579 A | 9/2015 |
|---|---|---|
| EP | 2919758 B1 | 9/2020 |

(Continued)

OTHER PUBLICATIONS

Habel, J et al Journal of Polymer Science Part B: Polymer Physics, vol. 54, Issue 7 pp. 699-708.*

(Continued)

*Primary Examiner* — Brian Gulledge
(74) *Attorney, Agent, or Firm* — Acuity Law Group, PC; Michael A. Whittaker

(57) ABSTRACT

The present invention relates to polymersomes comprising a soluble encapsulated antigen, wherein said soluble encapsulated antigen is selected from the group consisting of: a polypeptide, a carbohydrate, a polynucleotide and combinations thereof. The present invention further relates to a method for production of encapsulated antigens in a polymersome as well as to polymersomes produced by said method. The present invention further relates to compositions comprising a polymersome of the present invention, isolated antigen presenting cells or hybridoma cells exposed to the polymersome or composition of the present invention. The present invention also relates to vaccines comprising polymersomes of the present invention, methods of eliciting an immune response or methods for treatment, amelioration, (Continued)

prophylaxis or diagnostics of a cancer, autoimmune or infectious disease, comprising providing polymersomes of the present invention.

13 Claims, 15 Drawing Sheets

Specification includes a Sequence Listing.

(52) U.S. Cl.
CPC ............... *A61K 2039/55555* (2013.01); *A61K 2039/572* (2013.01)

(56) References Cited

FOREIGN PATENT DOCUMENTS

| JP | 2007-502780 A2 | 2/2007 |
| JP | 2016-500071 A2 | 1/2016 |
| WO | 2008/060557 A2 | 5/2008 |
| WO | 2014077781 A1 | 5/2014 |
| WO | 2016/055611 A1 | 4/2016 |
| WO | WO2017151922 A1 | 9/2017 |

OTHER PUBLICATIONS

International Search Report and Written Opinion issued in PCT/EP2019/051853 on Jul. 31, 20169 (31 pages).
Gao et al., "Effective intracellular delivery and Th1 immune response induced by ovalbumin loaded in pH-responsive polyphosphazene polymersomes", Nanomedicine. Jul. 2018;14(5):1609-1618. doi: 10.1016/j.nano.2018.04.001. Epub Apr. 9, 2018.
Kim et al., "Reactive Oxygen Species-Regulating Polymersome as an Antiviral Agent against Influenza Virus", Small. Aug. 2017;13(32). doi: 10.1002/smll.201700818. Epub Jul. 10, 2017.
Liu et al., "The highly efficient delivery of exogenous proteins into cells mediated by biodegradable chimaeric polymersomes", Biomaterials. Oct. 2010;31(29):7575-85. doi: 10.1016/j.biomaterials.2010.06.021.
Nazemi et al., "Multifunctional dendritic sialopolymersomes as potential antiviral agents: their lectin binding and drug release properties", Langmuir. May 28, 2013;29(21):6420-8. doi: 10.1021/la400890f. Epub May 14, 2013.
O'Neil et al., "A novel method for the encapsulation of biomolecules into polymersomes via direct hydration", Langmuir. Aug. 18, 2009;25(16):9025-9. doi: 10.1021/la900779t.
Quer et al., "Polymersomes enhance the immunogenicity of influenza subunit vaccine", Polym. Chem., 2, 1482.
Rincon-Restrepo et al., "Vaccine nanocarriers: Coupling intracellular pathways and cellular biodistribution to control CD4 vs CD8 T cell responses", Biomaterials. Jul. 2017;132:48-58. doi: 10.1016/j.biomaterials.2017.03.047. Epub Mar. 30, 2017.
Scott et al., "Dendritic cell activation and T cell priming with adjuvant- and antigen-loaded oxidation-sensitive polymersomes", Biomaterials. Sep. 2012;33(26):6211-9. doi: 10.1016/j.biomaterials.2012.04.060. Epub Jun. 1, 2012.
Stano et al., "Tunable T cell immunity towards a protein antigen using polymersomes vs. solid-core nanoparticles", Biomaterials. Jun. 2013;34(17):4339-46. doi: 10.1016/j.biomaterials.2013.02.024. Epub Mar. 9, 2013.
Scott et al.,, "Dendritic cell activation and T cell priming with adjuvant- and antigen-loaded oxidation-sensitive polymersomes", Biomaterials 33 (2012) 6211-6219.
Lam et al., Next generation vaccine platform: polymersomes as stable nanocarriers for a highly immunogenic and durable SARS-CoV-2 spike protein subunit vaccine. Accessed online at: https://www.biorxiv.org/content/10.1101/2021.01.24.427729v1.full.pdf pp. 1-48 [retrieved on Oct. 8, 2021].
Leong et al., Engineering Polymersomes for Diagnostics and Therapy. Adv Healthc Mater. Apr. 2018;7(8):e1701276.
Sexton et al., A Protective Vaccine Delivery System for In Vivo T Cell Stimulation Using Nanoengineered Polymer Hydrogel Capsules. ACS Nano. Nov. 24, 2009;3(11):3391-3400.
Office Action issued by the EPO in European Patent Application dated Jan. 26, 2023 (14 pages).
Kuai et al., Designer vaccine nanodiscs for personalized cancer immunotherapy.Nat Mater. Apr. 2017;16(4):489-496.
Zhu et al., Albumin/vaccine nanocomplexes that assemble in vivo for combination cancer immunotherapy. Nat Commun. Dec. 5, 2017;8(1):1954.
Office Action issued by the JPO in Japanese Patent Application No. 2020-560590 dated Mar. 1, 2023—incl Engl lang transl (12 pages total).
Habel et al., How Preparation and Modification Parameters Affect PB-PEO Polymersome Properties in Aqueous Solution. J Poly Sci Part B; Poly Physics 2016;15(16):1581-1592.
Office action issued by the JPO in Japanese patent application No. 2020-560590 dated Nov. 15, 2023 (incl Engl lang transl)—8 pages total.
Office Action issued by the CNIPA in Chinese patent Application # 201980021354.5 dated Aug. 12, 2023—incl Engl lang transl. (57 pages total).

* cited by examiner

| Formulation | Antigen/Peptide/DNA | Size (d. nm) | PDI[1] |
|---|---|---|---|
| BD21 | OVA | 173.1 | 0.108 |
| PDMS-PEG | PEDv S Protein | 127.3 | 0.206 |
| PDMS-PEG/DSPE-PEG | PEDv S Protein | 126.4 | 0.183 |
| PLA-PEG/Asolectin lipids | PEDv S Protein | 131.2 | 0.185 |
| $BD21-NH_2$ | eGFP-DNA | 155.8 | 0.11 |

[1] PDI, polydispersity index from dynamic light scattering (DLS)

SEQUENCE LISTING

```
<160> NUMBER OF SEQ ID NOS: 15

<210> SEQ ID NO 1
<211> LENGTH: 28
<212> TYPE: PRT
<213> ORGANISM: Artificial Sequence
<220> FEATURE:
<223> OTHER INFORMATION: Reps1 P45A peptide

<400> SEQUENCE: 1

Gly Arg Val Leu Glu Leu Phe Arg Ala Ala Gln Leu Ala Asn Asp Val
1               5                   10                  15

Val Leu Gln Ile Met Glu Leu Cys Gly Ala Thr Arg
            20                  25

<210> SEQ ID NO 2
<211> LENGTH: 28
<212> TYPE: PRT
<213> ORGANISM: Artificial Sequence
<220> FEATURE:
<223> OTHER INFORMATION: Adpgk R304M peptide

<400> SEQUENCE: 2

Gly Ile Pro Val His Leu Glu Leu Ala Ser Met Thr Asn Met Glu Leu
1               5                   10                  15

Met Ser Ser Ile Val His Gln Gln Val Phe Pro Thr
            20                  25

<210> SEQ ID NO 3
<211> LENGTH: 25
<212> TYPE: PRT
<213> ORGANISM: Artificial Sequence
<220> FEATURE:
<223> OTHER INFORMATION: Dpagt1 V213L peptide

<400> SEQUENCE: 3

Glu Ala Gly Gln Ser Leu Val Ile Ser Ala Ser Ile Ile Val Phe Asn
1               5                   10                  15

Leu Leu Glu Leu Glu Gly Asp Tyr Arg
            20                  25

<210> SEQ ID NO 4
```

```
<211> LENGTH: 386
<212> TYPE: PRT
<213> ORGANISM: Gallus gallus
<220> FEATURE:
<221> NAME/KEY: MISC_FEATURE
<222> LOCATION: (1)..(386)
<223> OTHER INFORMATION: Ovalbumin, UniProtKB Accession Number P01012

<400> SEQUENCE: 4

Met Gly Ser Ile Gly Ala Ala Ser Met Glu Phe Cys Phe Asp Val Phe
1               5                   10                  15

Lys Glu Leu Lys Val His His Ala Asn Glu Asn Ile Phe Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365
```

```
Ile Lys His Ile Ala Thr Asn Ala Val Leu Phe Phe Gly Arg Cys Val
        370                 375                 380

Ser Pro
385

<210> SEQ ID NO 5
<211> LENGTH: 566
<212> TYPE: PRT
<213> ORGANISM: Influenza A virus
<220> FEATURE:
<221> NAME/KEY: MISC_FEATURE
<222> LOCATION: (1)..(566)
<223> OTHER INFORMATION: Influenza A virus (A/New York/38/2016(H1N1))
      Hemagglutinin, UniProtKB Accession Number: A0A192ZYK0

<400> SEQUENCE: 5

Met Lys Ala Ile Leu Val Val Leu Leu Tyr Thr Phe Thr Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Asn Gln Ser Tyr Ile Asn Asp Lys Gly Lys Glu Val Leu Val
            180                 185                 190

Leu Trp Gly Ile His His Pro Ser Thr Thr Ala Asp Gln Gln Ser Leu
        195                 200                 205

Tyr Gln Asn Ala Asp Ala Tyr Val Phe Val Gly Thr Ser Arg Tyr Ser
210                 215                 220

Lys Lys Phe Lys Pro Glu Ile Ala Thr Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Thr Met Glu Arg Asn Ala Gly Ser Gly Ile Ile Ile Ser Asp Thr Pro
        275                 280                 285

Val His Asp Cys Asn Thr Thr Cys Gln Thr Pro Glu Gly Ala Ile Asn
290                 295                 300

Thr Ser Leu Pro Phe Gln Asn Ile His Pro Ile Thr Ile Gly Lys Cys
305                 310                 315                 320
```

```
Pro Lys Tyr Val Lys Ser Thr Lys Leu Arg Leu Ala Thr Gly Leu Arg
            325                 330                 335

Asn Val Pro

```
Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Pro Thr Ser Ala Asp Gln Gln Ser Leu
        195                 200                 205

Tyr Gln Asn Ala Asp Thr Tyr Val Phe Val Gly Ser Ser Arg Tyr Ser
    210                 215                 220

Lys Lys Phe Lys Pro Glu Ile Ala Ile Arg Pro Lys Val Arg Xaa Xaa
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Val Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
```

-continued

```
                500             505             510
Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
            530                 535             540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 7
<211> LENGTH: 565
<212> TYPE: PRT
<213> ORGANISM: Influenza A virus
<220> FEATURE:
<221> NAME/KEY: MISC_FEATURE
<222> LOCATION: (1)..(565)
<223> OTHER INFORMATION: Influenza A virus (H1N1/A/Puerto rico/8/1934)
      Hemagglutinin

<400> SEQUENCE: 7

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
```

```
                275                 280                 285
His Glu Cys Asn Thr Lys Cys Gln Thr Pro Leu Gly Ala Ile Asn Ser
        290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 8
<211> LENGTH: 566
<212> TYPE: PRT
<213> ORGANISM: Influenza A virus
<220> FEATURE:
<221> NAME/KEY: MISC_FEATURE
<222> LOCATION: (1)..(566)
<223> OTHER INFORMATION: Influenza A virus (A/California/07/2009(H1N1))
      Hemagglutinin

<400> SEQUENCE: 8

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
```

```
            50                  55                  60
Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Ala Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Ile Gly Asn Gly
465                 470                 475                 480
```

```
Cys Phe Glu Phe Tyr His Lys Cys Asp Asn Thr Cys Met Glu Ser Val
485 490 495

Lys Asn Gly Thr Tyr Asp Tyr Pro Lys Tyr Ser Glu Glu Ala Lys Leu
500 505 510

Asn Arg Glu Glu Ile Asp Gly Val Lys Leu Glu Ser Thr Arg Ile Tyr
515 520 525

Gln Ile Leu Ala Ile Tyr Ser Thr Val Ala Ser Ser Leu Val Leu Val
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 9
<211> LENGTH: 24
<212> TYPE: PRT
<213> ORGANISM: Artificial Sequence
<220> FEATURE:
<223> OTHER INFORMATION: CD8 Trp2 173-196 peptide

<400> SEQUENCE: 9

Gln Pro Gln Ile Ala Asn Cys Ser Val Tyr Asp Phe Phe Val Trp Leu
1 5 10 15

His Tyr Tyr Ser Val Arg Asp Thr
20

<210> SEQ ID NO 10
<211> LENGTH: 27
<212> TYPE: PRT
<213> ORGANISM: Artificial Sequence
<220> FEATURE:
<223> OTHER INFORMATION: CD4 M30 Kif18b K739N peptide

<400> SEQUENCE: 10

Pro Ser Lys Pro Ser Phe Gln Glu Phe Val Asp Trp Glu Asn Val Ser
1 5 10 15

Pro Glu Leu Asn Ser Thr Asp Gln Pro Phe Leu
20 25

<210> SEQ ID NO 11
<211> LENGTH: 27
<212> TYPE: PRT
<213> ORGANISM: Artificial Sequence
<220> FEATURE:
<223> OTHER INFORMATION: CD4 M44 Cpsf3l D314N peptide

<400> SEQUENCE: 11

Glu Phe Lys His Ile Lys Ala Phe Asp Arg Thr Phe Ala Asn Asn Pro
1 5 10 15

Gly Pro Met Val Val Phe Ala Thr Pro Gly Met
20 25

<210> SEQ ID NO 12
<211> LENGTH: 1309
<212> TYPE: PRT
<213> ORGANISM: Porcine epidemic diarrhea virus

<400> SEQUENCE: 12

Leu Pro Gln Asp Val Thr Arg Cys Ser Ala Asn Thr Asn Phe Arg Arg
1 5 10 15

Phe Phe Ser Lys Phe Asn Val Gln Ala Pro Ala Val Val Val Leu Gly

-continued

```
                 20                  25                  30
Gly Tyr Leu Pro Ile Gly Glu Asn Gln Gly Val Asn Ser Thr Trp Tyr
             35                  40                  45
Cys Ala Gly Gln His Pro Thr Ala Ser Gly Val His Gly Ile Phe Leu
         50                  55                  60
Ser His Ile Arg Gly Gly His Gly Phe Glu Ile Gly Ile Ser Gln Glu
 65                  70                  75                  80
Pro Phe Asp Pro Ser Gly Tyr Gln Leu Tyr Leu His Lys Ala Thr Asn
                 85                  90                  95
Gly Asn Thr Asn Ala Thr Ala Arg Leu Arg Ile Cys Gln Phe Pro Ser
                100                 105                 110
Ile Lys Thr Leu Gly Pro Thr Ala Asn Asn Asp Val Thr Thr Gly Arg
            115                 120                 125
Asn Cys Leu Phe Asn Lys Ala Ile Pro Ala His Met Ser Glu His Ser
            130                 135                 140
Val Val Gly Ile Thr Trp Asp Asn Asp Arg Val Thr Val Phe Ser Asp
145                 150                 155                 160
Lys Ile Tyr Tyr Phe Tyr Phe Lys Asn Asp Trp Ser Arg Val Ala Thr
                165                 170                 175
Lys Cys Tyr Asn Ser Gly Gly Cys Ala Met Gln Tyr Val Tyr Glu Pro
                180                 185                 190
Thr Tyr Tyr Met Leu Asn Val Thr Ser Ala Gly Glu Asp Gly Ile Ser
            195                 200                 205
Tyr Gln Pro Cys Thr Ala Asn Cys Ile Gly Tyr Ala Ala Asn Val Phe
        210                 215                 220
Ala Thr Glu Pro Asn Gly His Ile Pro Glu Gly Phe Ser Phe Asn Asn
225                 230                 235                 240
Trp Phe Leu Leu Ser Asn Asp Ser Thr Leu Val His Gly Lys Val Val
                245                 250                 255
Ser Asn Gln Pro Leu Leu Val Asn Cys Leu Leu Ala Ile Pro Lys Ile
                260                 265                 270
Tyr Gly Leu Gly Gln Phe Phe Ser Phe Asn Gln Thr Ile Asp Gly Val
            275                 280                 285
Cys Asn Gly Ala Ala Val Gln Arg Ala Pro Glu Ala Leu Arg Phe Asn
        290                 295                 300
Val Asp Asp Thr Ser Val Ile Leu Ala Glu Gly Ser Ile Val Leu His
305                 310                 315                 320
Thr Ala Leu Gly Thr Asn Phe Ser Phe Val Cys Ser Asn Ser Ser Asp
                325                 330                 335
Pro His Leu Ala Thr Phe Ala Ile Pro Leu Gly Ala Thr Gln Val Pro
            340                 345                 350
Tyr Tyr Cys Phe Leu Lys Val Asp Thr Tyr Asn Ser Thr Val Tyr Lys
        355                 360                 365
Phe Leu Ala Val Leu His Pro Thr Val Arg Glu Ile Val Ile Thr Lys
    370                 375                 380
Tyr Gly Asp Val Tyr Val Asn Gly Phe Gly Tyr Leu His Leu Gly Leu
385                 390                 395                 400
Leu Asp Ala Val Thr Ile Asn Phe Thr Gly His Gly Thr Asp Asp Asp
                405                 410                 415
Val Pro Gly Phe Trp Thr Ile Ala Ser Thr Asn Phe Val Asp Ala Leu
            420                 425                 430
Ile Glu Val Gln Gly Thr Ala Ile Gln Arg Ile Leu Tyr Cys Asp Asp
        435                 440                 445
```

-continued

```
Pro Val Ser Gln Leu Lys Cys Ser Gln Val Ala Phe Asp Leu Asp Asp
450                 455                 460
Gly Phe Tyr Pro Ile Ser Ser Arg Asn Leu Leu Ser His Glu Gln Pro
465                 470                 475                 480
Ile Ser Phe Val Thr Leu Pro Ser Phe Asn Asp His Ser Phe Val Asn
                485                 490                 495
Ile Thr Val Ser Ala Ser Phe Gly Gly His Ser Gly Ala Asn Leu Ile
                500                 505                 510
Ala Ser Asp Thr Thr Ile Asn Gly Phe Ser Ser Phe Cys Val Asp Thr
                515                 520                 525
Arg Gln Phe Thr Ile Ser Leu Phe Tyr Asn Val Thr Asn Ser Tyr Gly
530                 535                 540
Tyr Val Ser Lys Ser Gln Asp Ser Asn Cys Pro Phe Thr Leu Gln Ser
545                 550                 555                 560
Val Asn Asp Tyr Leu Ser Phe Ser Lys Phe Cys Val Ser Thr Ser Leu
                565                 570                 575
Leu Ala Ser Ala Cys Thr Ile Asp Leu Phe Gly Tyr Pro Glu Phe Gly
                580                 585                 590
Ser Gly Val Lys Phe Thr Ser Leu Tyr Phe Gln Phe Thr Lys Gly Glu
                595                 600                 605
Leu Ile Thr Gly Thr Pro Lys Pro Leu Glu Gly Val Thr Asp Val Ser
610                 615                 620
Phe Met Thr Leu Asp Val Cys Thr Lys Tyr Thr Ile Tyr Gly Phe Lys
625                 630                 635                 640
Gly Glu Gly Ile Ile Thr Leu Thr Asn Ser Ser Phe Leu Ala Gly Val
                645                 650                 655
Tyr Tyr Thr Ser Asp Ser Gly Gln Leu Leu Ala Phe Lys Asn Val Thr
                660                 665                 670
Ser Gly Ala Val Tyr Ser Val Thr Pro Cys Ser Phe Ser Glu Gln Ala
                675                 680                 685
Ala Tyr Val Asp Asp Asp Ile Val Gly Val Ile Ser Ser Leu Ser Asn
                690                 695                 700
Ser Thr Phe Asn Ser Thr Arg Glu Leu Pro Gly Phe Phe Tyr His Ser
705                 710                 715                 720
Asn Asp Gly Ser Asn Cys Thr Glu Pro Val Leu Val Tyr Ser Asn Ile
                725                 730                 735
Gly Val Cys Lys Ser Gly Ser Ile Gly Tyr Val Pro Ser Gln Ser Gly
                740                 745                 750
Gln Val Lys Ile Ala Pro Thr Val Ile Gly Asn Ile Ser Ile Pro Thr
                755                 760                 765
Asn Phe Ser Met Ser Ile Arg Thr Glu Tyr Leu Gln Leu Tyr Asn Thr
                770                 775                 780
Pro Val Ser Val Asp Cys Ala Thr Tyr Val Cys Asn Gly Asn Ser Arg
785                 790                 795                 800
Cys Lys Gln Leu Leu Thr Gln Tyr Thr Ala Ala Cys Lys Thr Ile Glu
                805                 810                 815
Ser Ala Leu Gln Leu Ser Ala Arg Leu Glu Ser Val Glu Val Asn Ser
                820                 825                 830
Met Leu Thr Ile Ser Glu Glu Ala Leu Gln Leu Ala Thr Ile Ser Ser
                835                 840                 845
Phe Asn Gly Asp Gly Tyr Asn Phe Thr Asn Val Leu Gly Val Ser Val
850                 855                 860
```

```
Tyr Asp Pro Ala Ser Gly Arg Val Val Gln Lys Arg Ser Phe Ile Glu
865                 870                 875                 880

Asp Leu Leu Phe Asn Lys Val Val Thr Asn Gly Leu Gly Thr Val Asp
                885                 890                 895

Glu Asp Tyr Lys Arg Cys Ser Asn Gly Arg Ala Val Ala Asp Leu Val
            900                 905                 910

Cys Ala Gln Tyr Tyr Ser Gly Val Met Val Leu Pro Gly Val Val Asp
            915                 920                 925

Ala Glu Lys Leu His Met Tyr Ser Ala Ser Leu Ile Gly Gly Met Val
930                 935                 940

Phe Gly Gly Phe Thr Ala Ala Ala Leu Pro Phe Ser Tyr Ala Val
945                 950                 955                 960

Gln Ala Arg Leu Asn Tyr Leu Ala Leu Gln Thr Asp Val Leu Gln Arg
            965                 970                 975

Asn Gln Gln Leu Leu Ala Glu Ser Phe Asn Ser Ala Ile Gly Asn Ile
                980                 985                 990

Thr Ser Ala Phe Glu Ser Val Lys Glu Ala Ile Ser Gln Thr Ser Lys
            995                 1000                1005

Gly Leu Asn Thr Val Ala His Ala Leu Thr Lys Val Gln Glu Phe
    1010                1015                1020

Val Asn Ser Gln Gly Ala Ala Leu Thr Gln Leu Thr Val Gln Pro
    1025                1030                1035

Gln His Asn Phe Gln Ala Ile Ser Ser Ser Ile Asp Asp Ile Tyr
    1040                1045                1050

Ser Arg Leu Asp Ile Leu Ser Ala Asp Val Gln Val Asp Arg Leu
    1055                1060                1065

Ile Thr Gly Arg Leu Ser Ala Leu Tyr Cys Phe Val Ala Gln Thr
    1070                1075                1080

Leu Thr Lys Tyr Thr Glu Val Gln Ala Ser Arg Lys Leu Ala Gln
    1085                1090                1095

Gln Lys Val Asn Glu Cys Val Lys Ser Gln Ser Gln Arg Tyr Gly
    1100                1105                1110

Phe Cys Gly Gly Asp Gly Glu His Ile Phe Ser Leu Val Gln Ala
    1115                1120                1125

Ala Pro Gln Gly Leu Leu Phe Leu His Thr Val Leu Val Pro Gly
    1130                1135                1140

Asp Phe Val Asn Val Ile Ala Ile Ala Gly Leu Cys Val Asn Asp
    1145                1150                1155

Glu Ile Ala Leu Thr Leu Arg Glu Pro Gly Leu Val Leu Phe Thr
    1160                1165                1170

His Glu Leu Gln Asn Tyr Asn Ala Thr Glu Tyr Phe Val Ser Ser
    1175                1180                1185

Arg Arg Met Phe Glu Pro Arg Lys Pro Thr Ala Ser Asp Phe Val
    1190                1195                1200

Gln Ile Glu Ser Cys Val Val Thr Tyr Val Asn Leu Thr Arg Asp
    1205                1210                1215

Gln Leu Pro Asp Val Ile Pro Asp Tyr Ile Asp Val Asn Lys Thr
    1220                1225                1230

Leu Asp Glu Ile Leu Ala Ser Leu Pro Asn Arg Thr Gly Pro Ser
    1235                1240                1245

Leu Pro Leu Asp Val Phe Asn Ala Thr Tyr Phe Asn Leu Thr Gly
    1250                1255                1260

Glu Met Ala Asp Leu Glu Leu Arg Ser Glu Ser Leu Arg Asn Asn
```

```
            1265                1270                1275

Thr Glu  Glu Leu Gln Ser Leu  Ile Tyr Asn Ile Asn  Asn Thr Leu
     1280                1285                1290

Val Asp  Leu Glu Trp Leu Asn  Arg Val Glu Thr Tyr  Ile Lys Trp
     1295                1300                1305

Pro

<210> SEQ ID NO 13
<211> LENGTH: 719
<212> TYPE: PRT
<213> ORGANISM: Porcine epidemic diarrhea virus

<400> SEQUENCE: 13

Leu Pro Gln Asp Val Thr Arg Cys Ser Ala Asn Thr Asn Phe Arg Arg
1               5                   10                  15

Phe Phe Ser Lys Phe Asn Val Gln Ala Pro Ala Val Val Leu Gly
                20                  25                  30

Gly Tyr Leu Pro Ile Gly Glu Asn Gln Gly Val Asn Ser Thr Trp Tyr
            35                  40                  45

Cys Ala Gly Gln His Pro Thr Ala Ser Gly Val His Gly Ile Phe Leu
        50                  55                  60

Ser His Ile Arg Gly Gly His Gly Phe Glu Ile Gly Ile Ser Gln Glu
65                  70                  75                  80

Pro Phe Asp Pro Ser Gly Tyr Gln Leu Tyr Leu His Lys Ala Thr Asn
                85                  90                  95

Gly Asn Thr Asn Ala Thr Ala Arg Leu Arg Ile Cys Gln Phe Pro Ser
            100                 105                 110

Ile Lys Thr Leu Gly Pro Thr Ala Asn Asn Asp Val Thr Thr Gly Arg
        115                 120                 125

Asn Cys Leu Phe Asn Lys Ala Ile Pro Ala His Met Ser Glu His Ser
130                 135                 140

Val Val Gly Ile Thr Trp Asp Asn Asp Arg Val Thr Val Phe Ser Asp
145                 150                 155                 160

Lys Ile Tyr Tyr Phe Tyr Phe Lys Asn Asp Trp Ser Arg Val Ala Thr
                165                 170                 175

Lys Cys Tyr Asn Ser Gly Gly Cys Ala Met Gln Tyr Val Tyr Glu Pro
            180                 185                 190

Thr Tyr Tyr Met Leu Asn Val Thr Ser Ala Gly Glu Asp Gly Ile Ser
        195                 200                 205

Tyr Gln Pro Cys Thr Ala Asn Cys Ile Gly Tyr Ala Ala Asn Val Phe
    210                 215                 220

Ala Thr Glu Pro Asn Gly His Ile Pro Glu Gly Phe Ser Phe Asn Asn
225                 230                 235                 240

Trp Phe Leu Leu Ser Asn Asp Ser Thr Leu Val His Gly Lys Val Val
                245                 250                 255

Ser Asn Gln Pro Leu Leu Val Asn Cys Leu Leu Ala Ile Pro Lys Ile
            260                 265                 270

Tyr Gly Leu Gly Gln Phe Phe Ser Phe Asn Gln Thr Ile Asp Gly Val
        275                 280                 285

Cys Asn Gly Ala Ala Val Gln Arg Ala Pro Glu Ala Leu Arg Phe Asn
    290                 295                 300

Val Asp Asp Thr Ser Val Ile Leu Ala Glu Gly Ser Ile Val Leu His
305                 310                 315                 320

Thr Ala Leu Gly Thr Asn Phe Ser Phe Val Cys Ser Asn Ser Ser Asp
```

325                 330                 335
Pro His Leu Ala Thr Phe Ala Ile Pro Leu Gly Ala Thr Gln Val Pro
            340                 345                 350
Tyr Tyr Cys Phe Leu Lys Val Asp Thr Tyr Asn Ser Thr Val Tyr Lys
        355                 360                 365
Phe Leu Ala Val Leu His Pro Thr Val Arg Glu Ile Val Ile Thr Lys
    370                 375                 380
Tyr Gly Asp Val Tyr Val Asn Gly Phe Gly Tyr Leu His Leu Gly Leu
385                 390                 395                 400
Leu Asp Ala Val Thr Ile Asn Phe Thr Gly His Gly Thr Asp Asp Asp
                405                 410                 415
Val Pro Gly Phe Trp Thr Ile Ala Ser Thr Asn Phe Val Asp Ala Leu
            420                 425                 430
Ile Glu Val Gln Gly Thr Ala Ile Gln Arg Ile Leu Tyr Cys Asp Asp
        435                 440                 445
Pro Val Ser Gln Leu Lys Cys Ser Gln Val Ala Phe Asp Leu Asp Asp
    450                 455                 460
Gly Phe Tyr Pro Ile Ser Ser Arg Asn Leu Leu Ser His Glu Gln Pro
465                 470                 475                 480
Ile Ser Phe Val Thr Leu Pro Ser Phe Asn Asp His Ser Phe Val Asn
                485                 490                 495
Ile Thr Val Ser Ala Ser Phe Gly Gly His Ser Gly Ala Asn Leu Ile
            500                 505                 510
Ala Ser Asp Thr Thr Ile Asn Gly Phe Ser Ser Phe Cys Val Asp Thr
        515                 520                 525
Arg Gln Phe Thr Ile Ser Leu Phe Tyr Asn Val Thr Asn Ser Tyr Gly
    530                 535                 540
Tyr Val Ser Lys Ser Gln Asp Ser Asn Cys Pro Phe Thr Leu Gln Ser
545                 550                 555                 560
Val Asn Asp Tyr Leu Ser Phe Ser Lys Phe Cys Val Ser Thr Ser Leu
                565                 570                 575
Leu Ala Ser Ala Cys Thr Ile Asp Leu Phe Gly Tyr Pro Glu Phe Gly
            580                 585                 590
Ser Gly Val Lys Phe Thr Ser Leu Tyr Phe Gln Phe Thr Lys Gly Glu
        595                 600                 605
Leu Ile Thr Gly Thr Pro Lys Pro Leu Glu Gly Val Thr Asp Val Ser
    610                 615                 620
Phe Met Thr Leu Asp Val Cys Thr Lys Tyr Thr Ile Tyr Gly Phe Lys
625                 630                 635                 640
Gly Glu Gly Ile Ile Thr Leu Thr Asn Ser Ser Phe Leu Ala Gly Val
                645                 650                 655
Tyr Tyr Thr Ser Asp Ser Gly Gln Leu Leu Ala Phe Lys Asn Val Thr
            660                 665                 670
Ser Gly Ala Val Tyr Ser Val Thr Pro Cys Ser Phe Ser Glu Gln Ala
        675                 680                 685
Ala Tyr Val Asp Asp Asp Ile Val Gly Val Ile Ser Ser Leu Ser Asn
    690                 695                 700
Ser Thr Phe Asn Ser Thr Arg Glu Leu Pro Gly Phe Phe Tyr His
705                 710                 715

<210> SEQ ID NO 14
<211> LENGTH: 590
<212> TYPE: PRT
<213> ORGANISM: Porcine epidemic diarrhea virus

<400> SEQUENCE: 14

```
Ser Asn Asp Gly Ser Asn Cys Thr Glu Pro Val Leu Val Tyr Ser Asn
1               5                   10                  15

Ile Gly Val Cys Lys Ser Gly Ser Ile Gly Tyr Val Pro Ser Gln Ser
            20                  25                  30

Gly Gln Val Lys Ile Ala Pro Thr Val Ile Gly Asn Ile Ser Ile Pro
        35                  40                  45

Thr Asn Phe Ser Met Ser Ile Arg Thr Glu Tyr Leu Gln Leu Tyr Asn
    50                  55                  60

Thr Pro Val Ser Val Asp Cys Ala Thr Tyr Val Cys Asn Gly Asn Ser
65                  70                  75                  80

Arg Cys Lys Gln Leu Leu Thr Gln Tyr Thr Ala Ala Cys Lys Thr Ile
                85                  90                  95

Glu Ser Ala Leu Gln Leu Ser Ala Arg Leu Glu Ser Val Glu Val Asn
            100                 105                 110

Ser Met Leu Thr Ile Ser Glu Glu Ala Leu Gln Leu Ala Thr Ile Ser
        115                 120                 125

Ser Phe Asn Gly Asp Gly Tyr Asn Phe Thr Asn Val Leu Gly Val Ser
    130                 135                 140

Val Tyr Asp Pro Ala Ser Gly Arg Val Val Gln Lys Arg Ser Phe Ile
145                 150                 155                 160

Glu Asp Leu Leu Phe Asn Lys Val Val Thr Asn Gly Leu Gly Thr Val
                165                 170                 175

Asp Glu Asp Tyr Lys Arg Cys Ser Asn Gly Arg Ala Val Ala Asp Leu
            180                 185                 190

Val Cys Ala Gln Tyr Tyr Ser Gly Val Met Val Leu Pro Gly Val Val
        195                 200                 205

Asp Ala Glu Lys Leu His Met Tyr Ser Ala Ser Leu Ile Gly Gly Met
    210                 215                 220

Val Phe Gly Gly Phe Thr Ala Ala Ala Leu Pro Phe Ser Tyr Ala
225                 230                 235                 240

Val Gln Ala Arg Leu Asn Tyr Leu Ala Leu Gln Thr Asp Val Leu Gln
                245                 250                 255

Arg Asn Gln Gln Leu Leu Ala Glu Ser Phe Asn Ser Ala Ile Gly Asn
            260                 265                 270

Ile Thr Ser Ala Phe Glu Ser Val Lys Glu Ala Ile Ser Gln Thr Ser
        275                 280                 285

Lys Gly Leu Asn Thr Val Ala His Ala Leu Thr Lys Val Gln Glu Phe
    290                 295                 300

Val Asn Ser Gln Gly Ala Ala Leu Thr Gln Leu Thr Val Gln Pro Gln
305                 310                 315                 320

His Asn Phe Gln Ala Ile Ser Ser Ser Ile Asp Asp Ile Tyr Ser Arg
                325                 330                 335

Leu Asp Ile Leu Ser Ala Asp Val Gln Val Asp Arg Leu Ile Thr Gly
            340                 345                 350

Arg Leu Ser Ala Leu Tyr Cys Phe Val Ala Gln Thr Leu Thr Lys Tyr
        355                 360                 365

Thr Glu Val Gln Ala Ser Arg Lys Leu Ala Gln Lys Val Asn Glu
    370                 375                 380

Cys Val Lys Ser Gln Ser Gln Arg Tyr Gly Phe Cys Gly Gly Asp Gly
385                 390                 395                 400

Glu His Ile Phe Ser Leu Val Gln Ala Ala Pro Gln Gly Leu Leu Phe
```

```
                        405                 410                 415
Leu His Thr Val Leu Val Pro Gly Asp Phe Val Asn Val Ile Ala Ile
                420                 425                 430

Ala Gly Leu Cys Val Asn Asp Glu Ile Ala Leu Thr Leu Arg Glu Pro
            435                 440                 445

Gly Leu Val Leu Phe Thr His Glu Leu Gln Asn Tyr Asn Ala Thr Glu
        450                 455                 460

Tyr Phe Val Ser Ser Arg Arg Met Phe Glu Pro Arg Lys Pro Thr Ala
465                 470                 475                 480

Ser Asp Phe Val Gln Ile Glu Ser Cys Val Val Thr Tyr Val Asn Leu
                485                 490                 495

Thr Arg Asp Gln Leu Pro Asp Val Ile Pro Asp Tyr Ile Asp Val Asn
            500                 505                 510

Lys Thr Leu Asp Glu Ile Leu Ala Ser Leu Pro Asn Arg Thr Gly Pro
        515                 520                 525

Ser Leu Pro Leu Asp Val Phe Asn Ala Thr Tyr Phe Asn Leu Thr Gly
    530                 535                 540

Glu Met Ala Asp Leu Glu Leu Arg Ser Glu Ser Leu Arg Asn Asn Thr
545                 550                 555                 560

Glu Glu Leu Gln Ser Leu Ile Tyr Asn Ile Asn Asn Thr Leu Val Asp
                565                 570                 575

Leu Glu Trp Leu Asn Arg Val Glu Thr Tyr Ile Lys Trp Pro
            580                 585                 590

<210> SEQ ID NO 15
<211> LENGTH: 237
<212> TYPE: PRT
<213> ORGANISM: Artificial Sequence
<220> FEATURE:
<223> OTHER INFORMATION: enhanced GFP

<400> SEQUENCE: 15

Ser Lys Gly Glu Glu Leu Phe Thr Gly Val Val Pro Ile Leu Val Glu
1               5                   10                  15

Leu Asp Gly Asp Val Asn Gly His Lys Phe Ser Val Arg Gly Glu Gly
                20                  25                  30

Glu Gly Asp Ala Thr Asn Gly Lys Leu Thr Leu Lys Phe Ile Cys Thr
            35                  40                  45

Thr Gly Lys Leu Pro Val Pro Trp Pro Thr Leu Val Thr Thr Leu Thr
        50                  55                  60

Tyr Gly Val Leu Cys Phe Ser Arg Tyr Pro Asp His Met Lys Arg His
65                  70                  75                  80

Asp Phe Phe Lys Ser Ala Met Pro Glu Gly Tyr Val Gln Glu Arg Thr
                85                  90                  95

Ile Ser Phe Lys Asp Asp Gly Thr Tyr Lys Thr Arg Ala Glu Val Lys
            100                 105                 110

Phe Glu Gly Asp Thr Leu Val Asn Arg Ile Glu Leu Lys Gly Ile Asp
        115                 120                 125

Phe Lys Glu Asp Gly Asn Ile Leu Gly His Lys Leu Glu Tyr Asn Phe
    130                 135                 140

Asn Ser His Asn Val Tyr Ile Thr Ala Asp Lys Gln Lys Asn Gly Ile
145                 150                 155                 160

Lys Ala Tyr Phe Lys Ile Arg His Asn Val Glu Asp Gly Ser Val Gln
                165                 170                 175

Leu Ala Asp His Tyr Gln Gln Asn Thr Pro Ile Gly Asp Gly Pro Val
```

-continued

```
              180                 185                 190
Leu Leu Pro Asp Asn His Tyr Leu Ser Thr Gln Ser Val Leu Ser Lys
        195                 200                 205

Asp Pro Asn Glu Lys Arg Asp His Met Val Leu Leu Glu Asp Val Thr
        210                 215                 220

Ala Ala Gly Ile Thr His Gly Met Asp Glu Leu Tyr Lys
225                 230                 235
```

POLYMERSOMES COMPRISING A SOLUBLE ENCAPSULATED ANTIGEN AS WELL AS METHODS OF MAKING AND USES THEREOF

CROSS-REFERENCE TO RELATED APPLICATIONS

The present invention is filed under 35 U.S.C. § 371 as the U.S. national phase of International Application No. PCT/EP2019/051853, filed Jan. 25, 2019, which designated the U.S. and claims the right of priority of European patent application No. 18153348.0, filed with the European Patent Office on Jan. 25, 2018. The entire disclosures of the above-identified priority applications are hereby fully incorporated herein by reference.

SEQUENCE LISTING

This application includes an electronically submitted sequence listing in .txt format. The .txt file contains a sequence listing entitled "2020-09-19_SCH-6300-US_ST25.txt" created on Sep. 19, 2020 and is 50,961 bytes in size. The sequence listing contained in this .txt file is part of the specification and is hereby incorporated by reference herein in its entirety.

TECHNICAL FIELD

The present invention relates to polymersomes including oxidation-stable polymersomes comprising a soluble or solubilized encapsulated antigen, wherein said soluble or solubilized encapsulated antigen is selected from the group consisting of: a polypeptide, a carbohydrate, a polynucleotide as well as combinations thereof.

BACKGROUND OF THE INVENTION

Although immunization is a well-established process, there are differences in the response level elicited between different immunogens or antigens. For example, membrane proteins form a class of antigens that produce a low response level, which in turn means that large amounts of membrane proteins are required to generate or elicit an immune response to the desired level. Membrane proteins are notoriously difficult to synthesize and are insoluble in water without the presence of a detergent. This makes it expensive and difficult to obtain membrane proteins in sufficient quantity for immunization. Furthermore, membrane proteins require proper folding to function correctly. The immunogenicity of correctly folded native membrane proteins is typically much better than that of their solubilized forms, which may not be folded in a physiologically relevant manner. Thus, even though adjuvants may be used to boost the immunogenicity of such solubilized antigens, it is an inefficient method that does not provide too much of an advantage (e.g., WO2014/077781A1).

Although transfected cells and lipid-based systems have been used to present membrane protein antigens to increase the chances of isolating antibodies that may be efficient in vivo, these systems are often unstable (e.g., oxidation sensitive), tedious and costly. Moreover, the current state of the art for such membrane protein antigens is to use inactive virus-like particles for immunization.

On the other hand, vaccines are the most efficient way to prevent diseases, mainly infectious diseases [e.g., Liu et al., 2016]. As of today, most of the licensed vaccines are made of either live or killed viruses. Despite their effectiveness in generating a humoral response (an antibody mediated response) to prevent viral propagation and entry into cells, safety of such vaccines remains a concern. In the past few decades, scientific advances have helped to overcome such issues by engineering vaccine vectors that are non-replicating recombinant viruses. In parallel, protein based antigens or sub-unit antigens are explored as safer alternatives. However, such protein based vaccines typically illicit poor immune (both humoral and cellular response). To improve immunogenic properties of antigens, several approaches have been used. For example, microencapsulation of antigens into polymers have been investigated extensively, although it did enhance the immunogenicity, aggregation and denaturing of antigens remain unsolved [e.g., Hilbert et al., 1999]. Furthermore, adjuvants (e.g., oil in water emulsions or polymer emulsions) [e.g., U.S. Pat. No. 9,636,397B2, US2015/0044242 A1] are used together with antigens to elicit a more pronounced humoral and cellular response. Despite these advances, they are less efficient in uptake and cross-presentation. To promote cross-presentation, based on the available information of the immune system during infection by viruses, viral like particles that mimics such properties have been exploited. Synthetic architectures such as liposomes with encapsulated antigens are particularly attractive. Liposomes are unilamellar self-assembling structures made of lipids and, cationic liposomes are more attractive and promising as delivery vehicles because of their efficient uptake by Antigen Presenting Cells (APCs) [e.g., Maji et al., 2016]. Furthermore, it allows to integrate immunomodulators such as Monophosphoryl Lipid A (MPL), CpG oligodeoxynucleotide, that are toll-like receptor (TLR) agonists which stimulate immune cells through receptors. Despite these opportunities of such delivery vehicles, one of the limiting factors is stability of liposomes in the presence of serum components. By PEGylations, loading with high melting temperature lipids, stability issues of liposomes are somewhat reduced with and one such well characterized example being interbilayered-crosslinked multilamellar vesicles (ICMVs), formed by stabilizing multilamellar vesicles with short covalent crosslinks linking lipids [e.g., Moon et al., 2011]. Other nanoparticle architectures have led to successful immunisations using nanodiscs [e.g., Kuai et al., 2017] or pH sensitive particles [e.g., Luo et al., 2017]. But such strategies either still requires adjuvants or are not as efficient outside the prototypical Ovalbumin (OVA) models.

In addition, polymersomes, offer as a stable alternative for liposomes and they have been used to integrate membrane proteins to elicit immune response [e.g., Quer et al., 2011, WO2014/077781A1]. Protein antigens were also encapsulated in a chemically altered membrane of the polymersome (however oxidation-sensitive membranes) to release antigens and the adjuvants to dendritic cells [e.g., Stano et al., 2013].

Despite this progress made by the use of polymers, there remains a need to provide for efficient uptake and stable cross-presentation delivery vehicles and methods that overcome, or at least alleviate, the above problems as well as possess an improved functionality inter alia in that they are also capable of eliciting a $CD8^{(+)}$ T cell-mediated immune response, which is particularly important in treatment and/or prevention of infectious diseases, cancers and autoimmune diseases.

SUMMARY OF THE INVENTION

The present invention relates to polymersomes including oxidation-stable polymersomes (as efficient uptake and stable cross-presentation delivery vehicles) comprising a soluble encapsulated antigen, wherein said soluble encapsulated antigen is selected from the group consisting of: a polypeptide, a carbohydrate, a polynucleotide and combinations thereof. The present invention further relates to a method for production of encapsulated antigens in a polymersome as well as to polymersomes produced by said method. The present invention further relates to compositions comprising polymersomes of the present invention, isolated antigen presenting cells and hybridoma cells exposed to polymersomes or compositions of the present invention. The present invention also relates to vaccines comprising polymersomes of the present invention, methods of eliciting an immune response or methods for treatment, amelioration, prophylaxis or diagnostics of cancers, autoimmune or infectious diseases, such methods comprising providing polymersomes of the present invention to subject in need thereof.

The invention also relates to the use of a polymersome having a diameter of about 120 nm or 140 nm or more comprising a soluble encapsulated antigen, wherein said soluble encapsulated antigen is selected from the group consisting of:
i) a polypeptide;
ii) a carbohydrate;
iii) a polynucleotide, preferably said polynucleotide is not an antisense oligonucleotide, further preferably said polynucleotide is a DNA or mRNA molecule, or
iv) a combination of i) and/or ii) and/or iii).
for eliciting an immune response.

The use of a collection of polymersomes having a mean diameter of about 120 nm, or 140 nm or more, the polymersomes of the collection comprising a soluble encapsulated antigen, wherein said soluble encapsulated antigen is selected from the group consisting of:
i) a polypeptide;
ii) a carbohydrate;
iii) a polynucleotide, preferably said polynucleotide is not an antisense oligonucleotide, further preferably said polynucleotide is a DNA or mRNA molecule, or
iv) a combination of i) and/or ii) and/or iii).
for eliciting an immune response.

Furthermore, in the course of the present invention it was found that providing the polymersomes of the present invention allows soluble (or solubilized) encapsulated (in said polymersomes) antigens to produce a stronger humoral immune response (compared to free antigens with or without adjuvants) as well as elicit a $CD8^{(+)}$ T cell-mediated immune response. Consequently, an increase in the efficiency of antibody production in a subject is achieved. The increase in the efficiency can be attained with or without the use of adjuvants. Furthermore, the ability of the polymersomes of the present invention to elicit a $CD8^{(+)}$ T cell-mediated immune response dramatically increases their potential as an immunotherapeutic antigen delivery and presentation system.

Because soluble (e.g., solubilized) encapsulated antigens presented by polymersomes, the antibodies produced by the use of polymersomes and methods of the present invention would not only have a higher production success rate and higher affinity for their corresponding in vitro or in vivo targets and accordingly improved sensitivity when used in various solution-based antibody applications, but also would make possible to easily raise antibodies to difficult antigens not capable of triggering antibody production by conventional methods using free antigen injections and/or decrease the amount of antigen required for such antibody production procedure thus decreasing the cost of such a production. Furthermore, soluble (e.g., solubilized) encapsulated antigens presented by polymersomes of the present invention are also capable of eliciting a $CD8^{(+)}$ T cell-mediated immune response, which extends the use of corresponding polymersomes to cell-mediated immunity and therefore improves their immunotherapeutic- and antigen delivery and presentation potential.

Therefore, the present application satisfies this demand by provision of oxidation-stable polymersomes that improve immunogenic properties of antigens, methods for their production and compositions comprising such polymersomes, described herein below, characterized in the claims and illustrated by the appended Examples and Figures.

OVERVIEW OF THE SEQUENCE LISTING

As described herein references are made to UniProtKB Accession Numbers (http://www.uniprot.org/e.g., as available in UniProtKB Release 2017_12).

SEQ ID NO: 1 is the amino acid sequence of the tumor neoantigen polypeptide Reps1 P45A derived from the colon cancer MC-38 mouse model.

SEQ ID NO: 2 is the amino acid sequence of the tumor neoantigen peptide Adpgk R304M derived from the colon cancer MC-38 mouse model.

SEQ ID NO: 3 is the amino acid sequence of the tumor neoantigen peptide Dpagt1 V213L derived from the colon cancer MC-38 mouse model.

SEQ ID NO: 4 is the amino acid sequence of the chicken Ovalbumin (OVA), UniProtKB Accession Number: P01012.

SEQ ID NO: 5 is the amino acid sequence of the influenza A virus (A/New York/38/2016(H1N1)) hemagglutinin, UniProtKB Accession Number: A0A192ZYK0.

SEQ ID NO: 6 is the amino acid sequence of the influenza A virus (A/swine/4/Mexico/2009(H1N1)) hemagglutinin, UniProtKB Accession Number: D2CE65.

SEQ ID NO: 7 is the amino acid sequence of the influenza A virus (A/Puerto rico/8/1934(H1N1)) hemagglutinin.

SEQ ID NO: 8 is the amino acid sequence of the influenza A virus (A/California/07/2009(H1N1)) hemagglutinin.

SEQ ID NO: 9 is the amino acid sequence of the tumor neoantigen polypeptide CD8 Trp2 173-196 derived from the melanoma B16-F10 mouse model.

SEQ ID NO: 10 is the amino acid sequence of the tumor neoantigen polypeptide CD4 M30 Kif18b K739N derived from the melanoma B16-F10 mouse model.

SEQ ID NO: 11 is the amino acid sequence of the tumor neoantigen polypeptide CD4 M44 Cpsf31 D314N derived from the melanoma B16-F10 mouse model.

SEQ ID NO: 12 is the amino acid sequence of the soluble portion (amino acid residues 19 to 1327) of the Porcine Epidemic Diarrhea virus (PEDv) Spike protein (S Protein) (UniProtKB Accession number: V5TA78)

SEQ ID NO: 13 is the amino acid sequence of the S1 region (amino acid residues 19 to 739) of the PEDv Spike protein (S Protein) and SEQ ID NO: 14 is the amino acid sequence of the S2 region (amino acid residues 739 to 1327) of the PEDv Spike protein (S Protein)

SEQ ID NO: 15 is the amino sequence of the enhanced Green Fluorescent Protein (eGFP).

BRIEF DESCRIPTION OF THE DRAWINGS

FIG. 2 shows the results of dynamic light scattering results for polymersome of the invention. FIG. 2B shows a table of mean diameter (Z average) measured by DLS for different polymersomes encapsulated with different antigens.

As seen in FIG. 11 the titres raises over time, showing that the orally administered polymersomes of the invention with PEDv S protein encapsulated therein, are able to elicit an immune response in the swine.

DETAILED DESCRIPTION OF THE INVENTION

Figure 1:
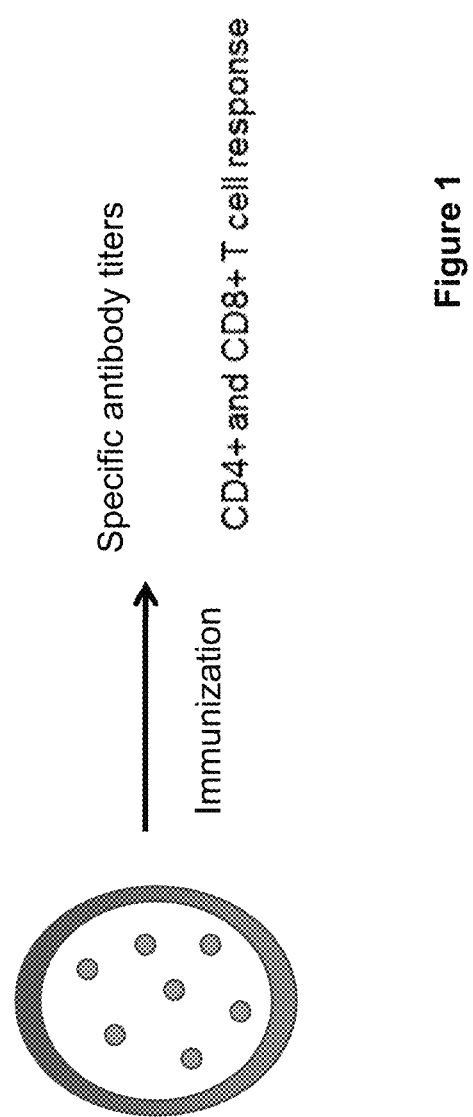
FIG. 1 shows a schematic view of the immunization with a polymersome of the present invention encapsulating antigens and measuring the humoral and cellular responses.

The following detailed description refers to the accompanying Examples and Figures that show, by way of illustration, specific details and embodiments, in which the invention may be practised. These embodiments are described in sufficient detail to enable those skilled in the art to practice the invention. Other embodiments may be utilized such that structural, logical, and eclectic changes may be made without departing from the scope of the invention. Various aspects of the present invention described herein are not necessarily mutually exclusive, as aspects of the present invention can be combined with one or more other aspects to form new embodiments of the present invention.

In the present context, polymersomes are vesicles with a polymeric membrane, which are typically, but not necessarily, formed from the self-assembly of dilute solutions of one or more amphiphilic block copolymers, which can be of different types such as diblock and triblock (A-B-A or A-B-C). Polymersomes of the present invention may also be formed of tetra-block or penta-block copolymers. For triblock copolymers, the central block is often shielded from the environment by its flanking blocks, while di-block copolymers self-assemble into bilayers, placing two hydrophobic blocks tail-to-tail, much to the same effect. In most cases, the vesicular membrane has an insoluble middle layer and soluble outer layers. The driving force for polymersome formation by self-assembly is considered to be the microphase separation of the insoluble blocks, which tend to associate in order to shield themselves from contact with water. Polymersomes of the present invention possess remarkable properties due to the large molecular weight of the constituent copolymers. Vesicle formation is favored upon an increase in total molecular weight of the block copolymers. As a consequence, diffusion of the (polymeric) amphiphiles in these vesicles is very low compared to vesicles formed by lipids and surfactants. Owing to this less mobility of polymer chains aggregated in vesicle structure, it is possible to obtain stable polymersome morphologies. Unless expressly stated otherwise, the term "polymersome" and "vesicle", as used herein, are taken to be analogous and may be used interchangeably. Importantly, a polymersome of the invention can be formed from either one kind pf block copolymers or from two or more kinds of block copolymers, meaning a polymersome can also be formed from a mixtures of polymersomes and thus can contain two or more block copolymers. In some aspects, the polymersome of the present invention is oxidation-stable.

In some aspects, the present invention relates to a method for eliciting an immune response to a soluble (e.g., solubilized) encapsulated antigen in a subject. The method is suitable for injecting the subject with a composition comprising a polymersome (e.g., carrier or vehicle) having a membrane (e.g., circumferential membrane) of an amphiphilic polymer. The composition comprises a soluble (e.g., solubilized) antigen encapsulated by the membrane (e.g., circumferential membrane) of the amphiphilic polymer of the polymersome of the present invention. The antigen may be one or more of the following: i) a polypeptide; ii) a carbohydrate; iii) a polynucleotide (e.g., said polynucleotide is not an antisense oligonucleotide, preferably said polynucleotide is a DNA or messenger RNA (mRNA) molecule) or a combination of i) and/or ii) and/or iii).

In some further aspects, the present invention relates to polymersomes capable of eliciting a CD8(+) T cell-mediated immune response.

In some aspects, the present invention relates to polymersomes capable of targeting of lymph node-resident macrophages and/or B cells. Exemplary non-limiting targeting mechanisms envisaged by the present invention include: i) delivery of encapsulated antigens (e.g., polypeptides, etc.) to dendritic cells (DCs) for T cell activation (CD4 and/or CD8). Another one is: ii) delivery of whole folded antigens (e.g., proteins, etc.) that will be route to DC and will also trigger a titer (B cells).

In some aspects, the present invention relates to polymersomes encapsulating an antigen selected from a group consisting of: i) a self-antigen, ii) a non-self antigen, iii) a non-self immunogen and iv) a self-immunogen. Accordingly, the products and methods of the present invention are suitable for uses in settings (e.g., clinical settings) of induced tolerance, e.g., when targeting an autoimmune disease.

In some aspects, the present invention relates to polymersomes of the present invention comprising a lipid polymer.

The polymersomes of the present invention can also have co-encapsulated (i.e. encapsulated in addition to the antigen) one or more adjuvants. Examples of adjuvants include synthetic oligodeoxynucleotides (ODNs) containing unmethylated CpG motifs which can trigger cells that express Toll-like receptor 9 (including human plasmacytoid dendritic cells and B cells) to mount an innate immune response characterized by the production of Th1 and proinflammatory cytokines, cytokines such as Interleukin-1, Interleukin-2 or Interleukin-12, keyhole limpet hemocyanin (KLH), serum albumin, bovine thyroglobulin, or soybean trypsin inhibitor, too name only a few illustrative examples.

Figure 2A:
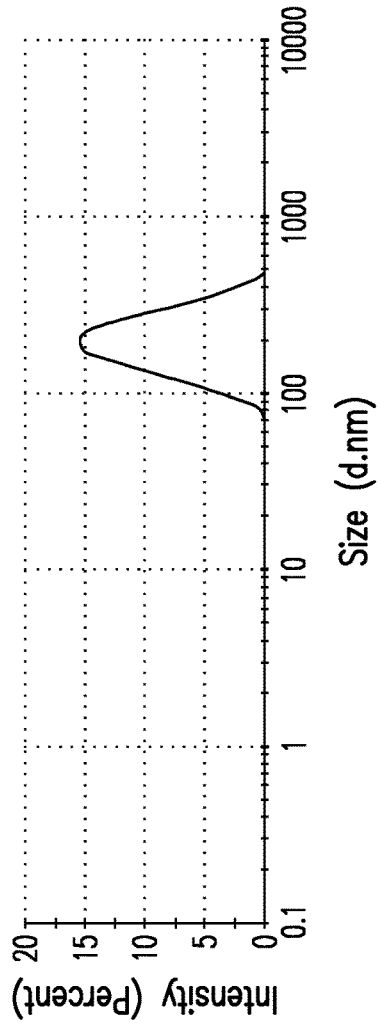
FIG. 2A shows dynamic light scattering plot of OVA encapsulating polymersomes with a monodisperse population of 173.1 nm (diameter).
Figure 3:
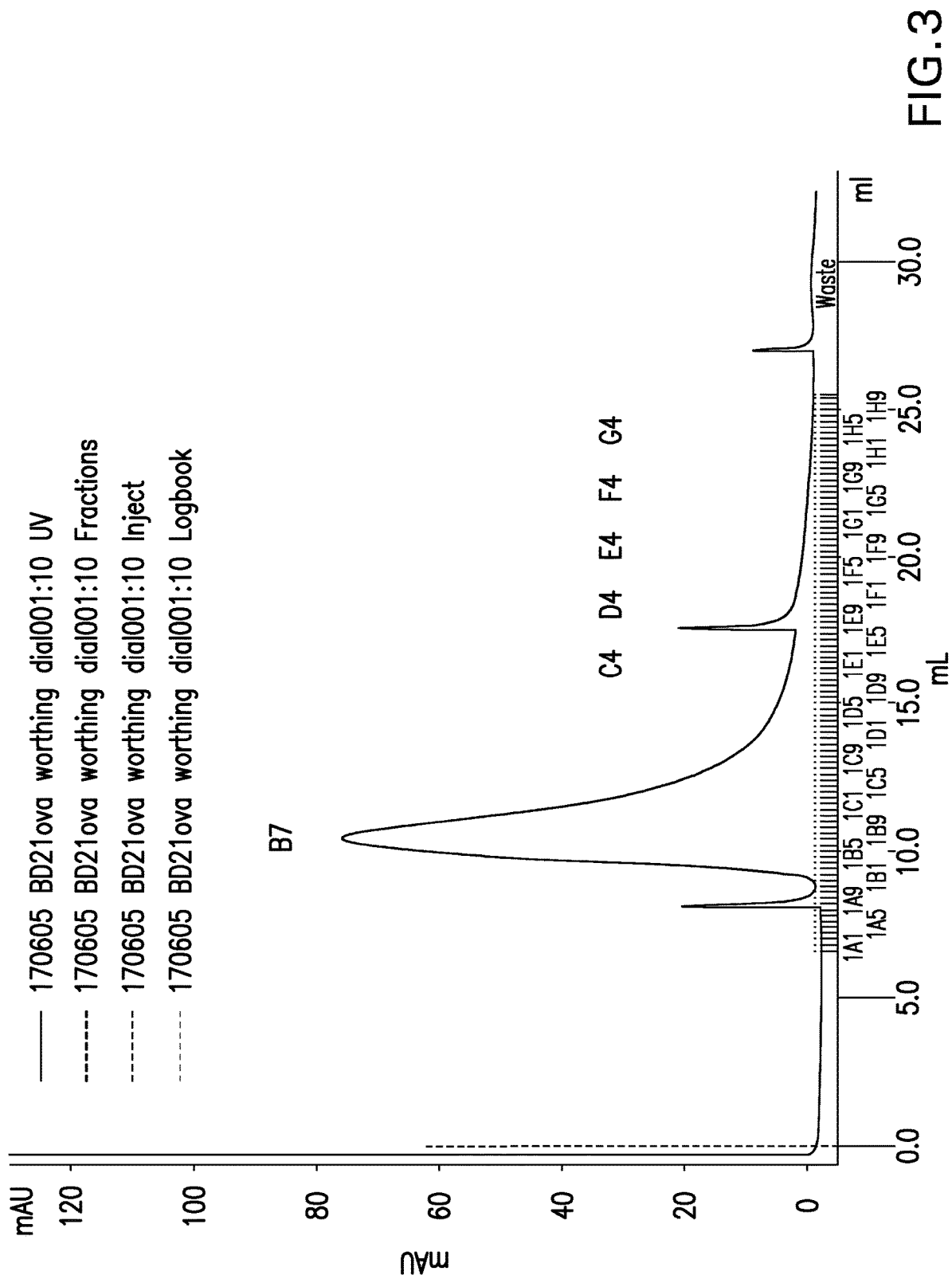
FIG. 3 shows an elution profile of OVA encapsulating polymersome in a size exclusion chromatography.
Figure 4:
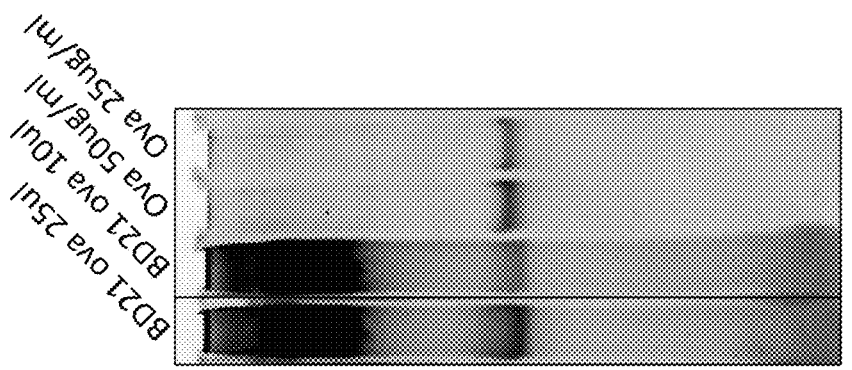
FIG. 4 shows sodium dodecyl sulphate-polyacrylamide gel electrophoresis (SDS-PAGE) of OVA encapsulating polymersomes.
Figure 4:
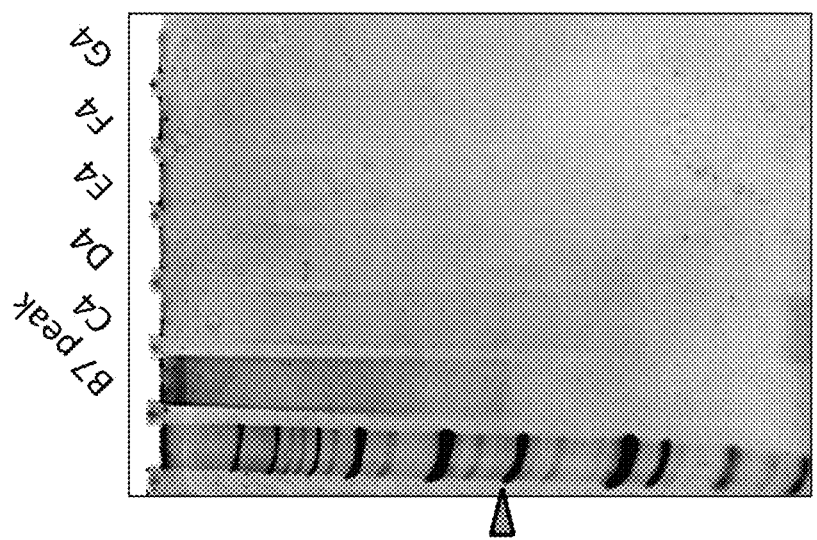
Figure 5A:
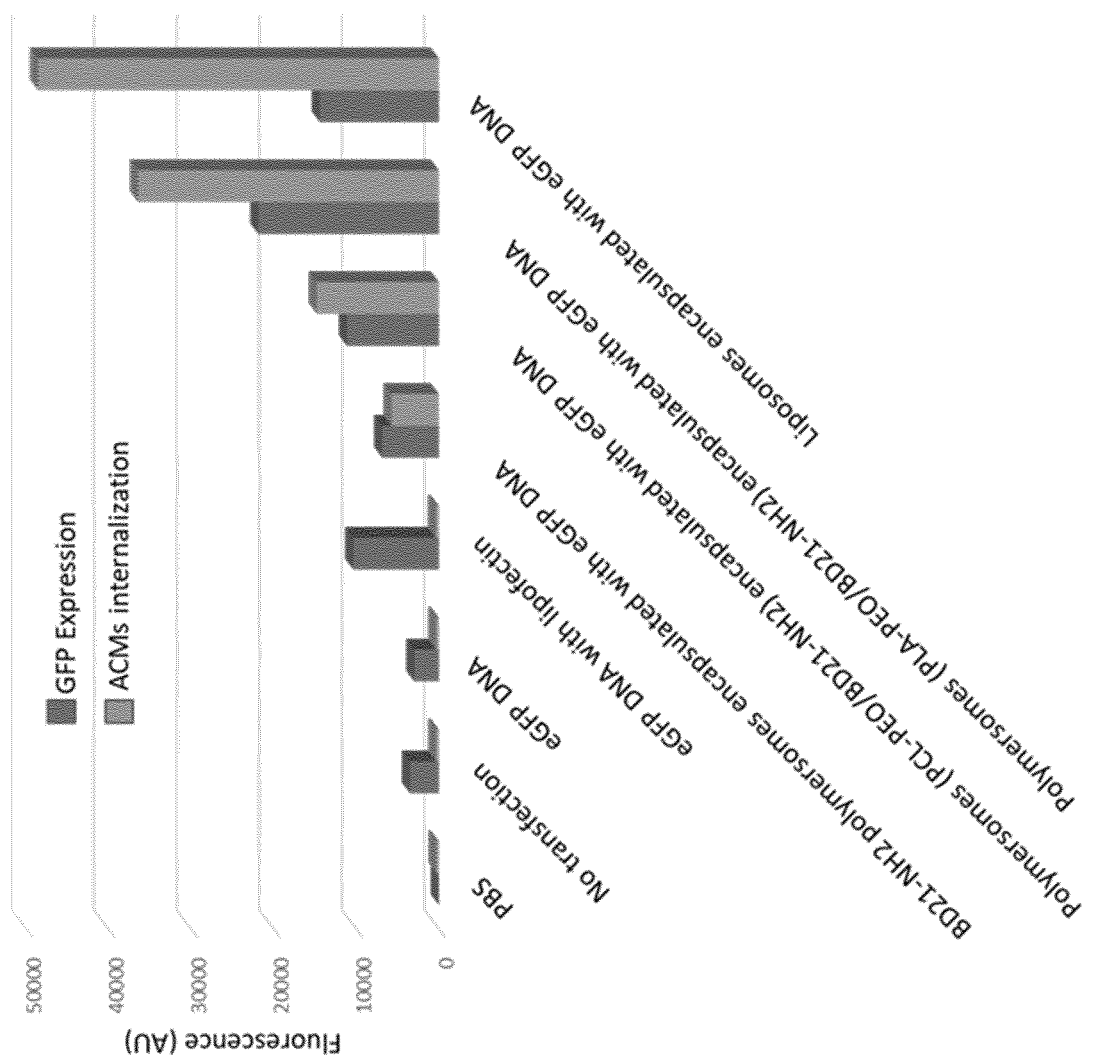
FIG. 5A shows.fluorescence intensity uptake of different polymersomes inside the cells and eGFP expression based on the DNA encapsulated in the polymersomes, while FIG. 5B and FIG. 5C show fluorescence images of cells that are transfected with DNA encapsulated polymersomes.
Figure 5B:
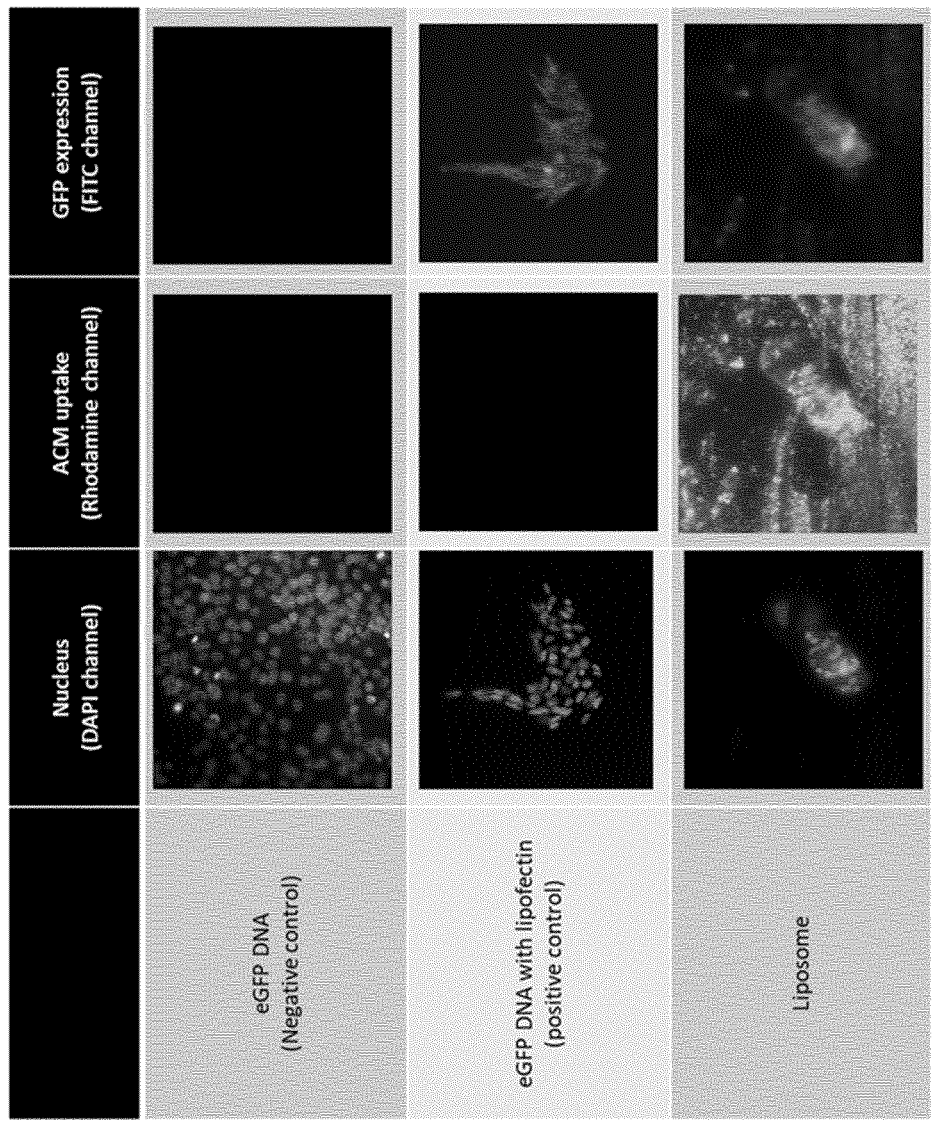
FIG. 5 shows the results of encapsulation of a nucleic acid (here the coding gene of enhanced Green Flourescent Protein (eGFP) in polymersomes of the invention and uptake of the polymers with the encapsulated nucleic acid in cells.
Figure 5C:
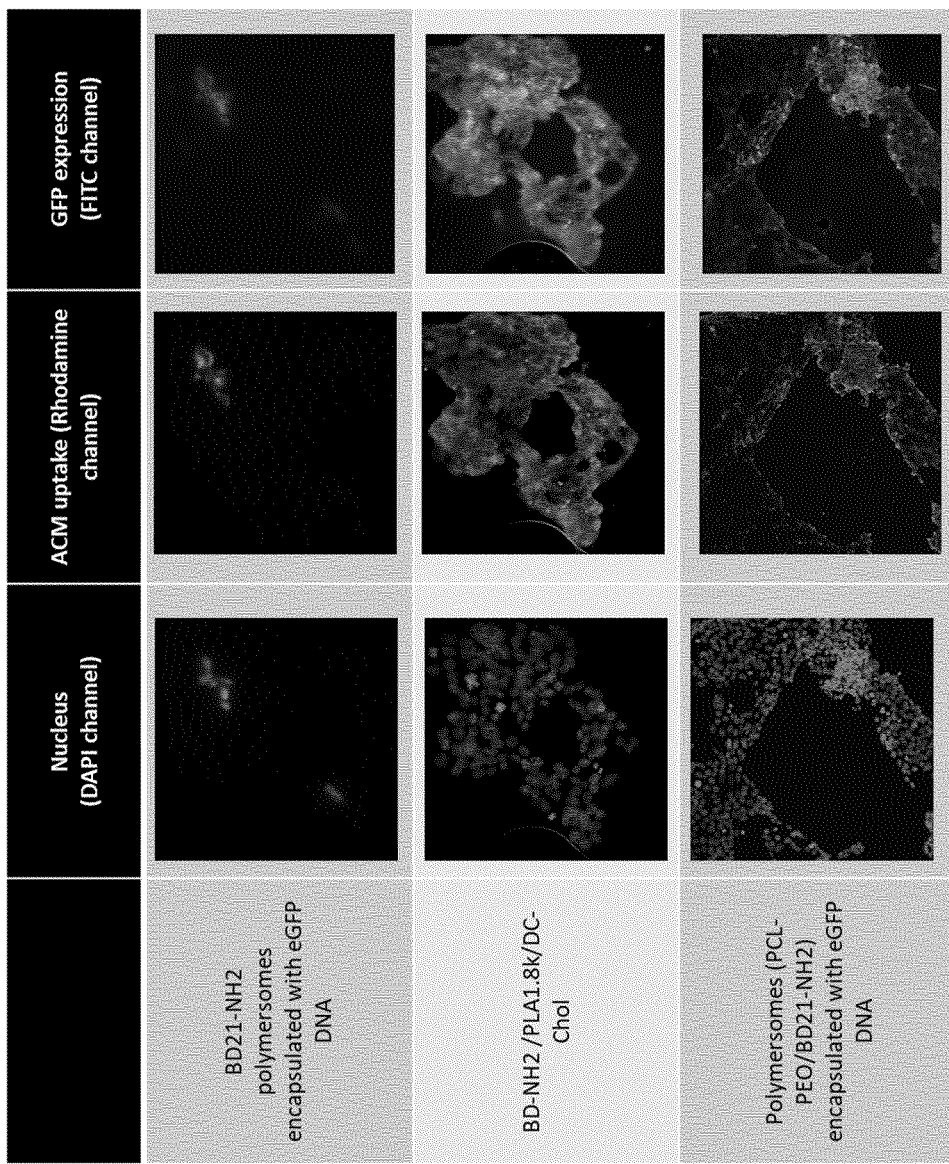
Figure 6:
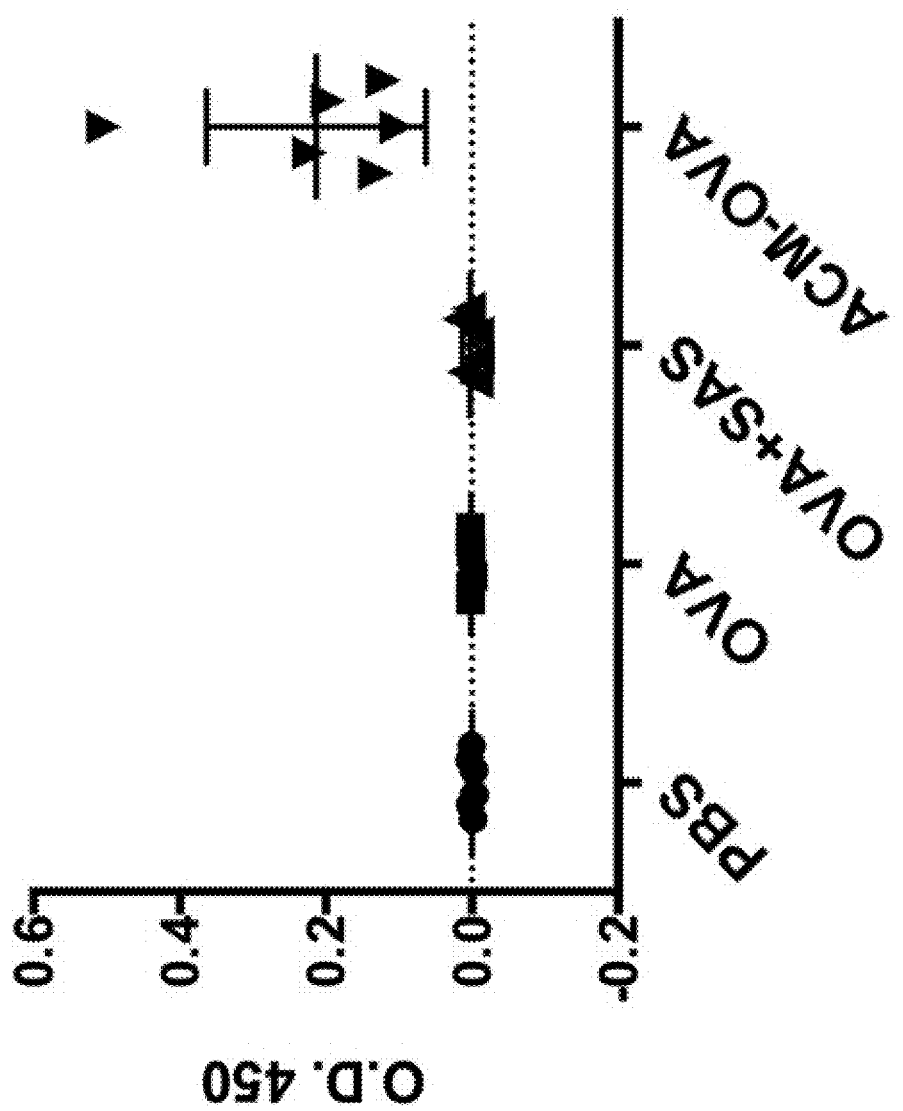
FIG. 6 shows antibody titers from the mice sera that were immunized with PBS, OVA alone, OVA with SAS adjuvant, OVA encapsulating polymersomes without adjuvants. Only ACM encapsulated OVA (herein after "ACM" refers to a polymersome of the present invention) was able to induce an IgG titer.
Figure 7:
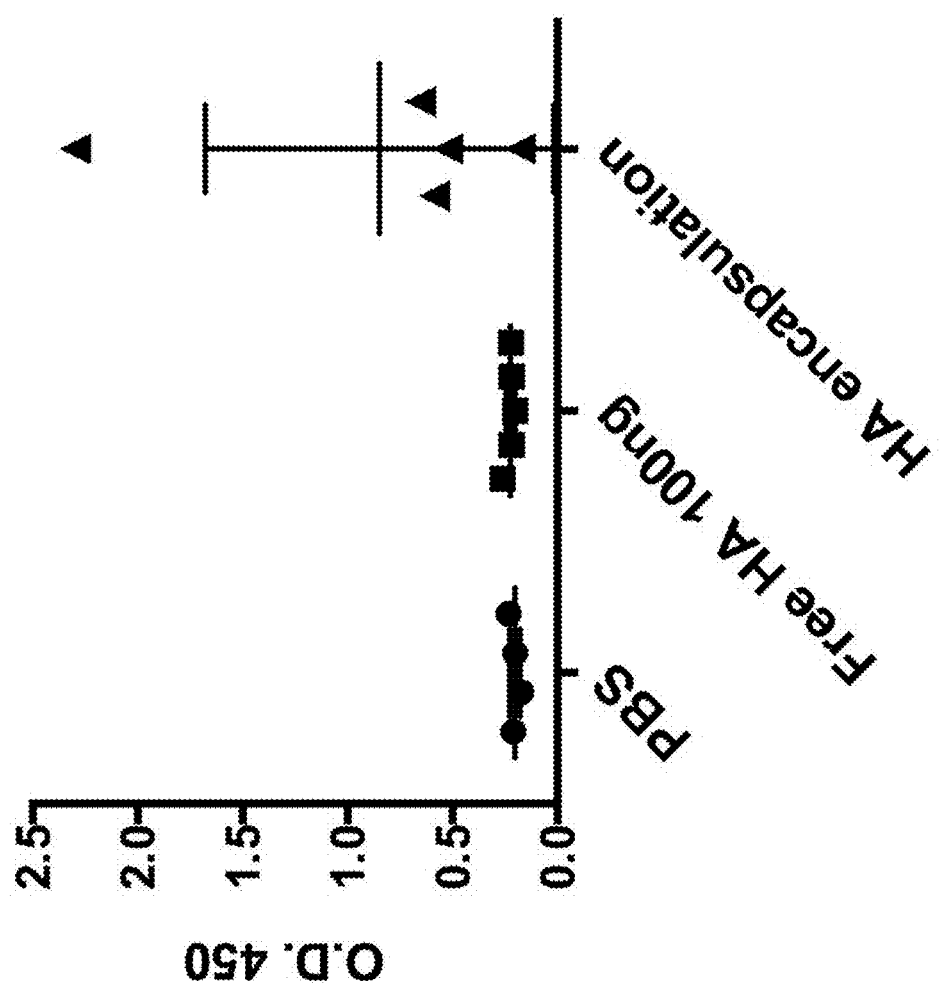
FIG. 7 shows antibody titers from the mice sera that were immunized with PBS, HA alone and HA encapsulating polymersomes without adjuvants. Only ACM encapsulated HA (polymersome of the present invention) was able to induce an IgG titer.

The polymersomes of the present invention can be of any size as long as the polymersomes are able to elicit an immune response. For example, the polymersomes may have a diameter of greater than 70 nm. The diameter of the polymersomes may range from about 100 nm to about 1 µm, or from about 100 nm to about 750 nm, or from about 100 nm to about 500 nm. The diameter of the polymersome may further range from about 125 nm to about 175 nm or, from about 125 nm to about 250 nm, from about 140 nm to about 240 nm, from about 150 nm to about 235 nm, from about 170 nm to about 230 nm, or from about 220 nm to about 180 nm, or from about 190 nm to about 210 nm. The diameter of the polymersomes may, for example, about 200 nm; about 205 nm or about 210 nm. When used as a collection to elicit an immune response, the collection of polymersomes is typically a monodisperse population. The mean diameter of the used collection/population of polymersomes is typically above 70 nm, or above 120 nm, or above 125 nm, or above 130 nm, or above 140 nm, or above 150 nm, or above 160 nm, or for above 170 nm, or above 180 nm, or above 190 nm (cf. also FIG. 2 in this respect). The mean diameter of the collection of polymersomes may, for example, also in range of the individual polymersomes mentioned above, meaning the mean diameter of the collection of polymersomes may be in the range of 100 nm to about 1 µm, or in the range of about 100 nm to about 750 nm, or in the range of about 100 nm to about 500 nm, or in the range from about 125 nm to about 250 nm, from about 140 nm to about 240 nm, from about 150 nm to about 235 nm, from about 170 nm to about 230 nm, or from about 220 nm to about 180 nm, or from about 190 nm to about 210 nm. The mean diameter of the collection of polymersomes may, for example, also be about 200 nm; about 205 nm or about 210 nm. The diameter can, for example, be determined by a dynamic light scattering (DLS) instrument using Z-average (d, nm), a preferred DLS parameter. Z-average size is the intensity weighted harmonic mean particle diameter (cf. Examples 1 and 2). In this context, it is noted that according to U.S. Pat. No. 8,323,696 of Hubbel et al, a collection of polymersomes should have a mean diameter of less than 70 nm to be able to elicit immune response. Similarly, Stano et al, supra, 2013, while wanting to use smaller polymersome, used, due to technical constraints, polymersomes having a diameter of 125 nm+/− 15 nm to elicit an immune response. Thus, it is surprising that a population/collection of polymersomes of the present invention with a mean diameter of, for example, than more 150 nm are able to induce both a cellular and a humoral immune response (cf. Example section). Such a collection of polymersomes may be in a form suitable for eliciting an immune response, for example, by injection or oral administration.

In some aspects, the present invention relates to compositions of the present invention suitable for intradermal, intraperitoneal, subcutaneous, intravenous, or intramuscular injection, or non-invasive administration of an antigen of the present invention, for example, oral administration or nasal administration. The composition may include a polymersome (e.g., carrier) of the present invention having a membrane (e.g., circumferential membrane) of an amphiphilic polymer. The composition further includes a soluble (e.g., solubilized) antigen encapsulated by the membrane of the amphiphilic polymer of the polymersome. The compositions of the present invention may be used for therapeutic purposes (for example, treatment of a subject suffering from a disease or for preventing from suffering from a disease, for example, by means of vaccination) or be used in antibody discovery, vaccine discovery, or targeted delivery.

In some aspects, polymersomes of the present invention have hydroxyl groups on their surface. In some further aspects, polymersomes of the present invention do not have hydroxyl groups on their surface.

In the present context, the term "encapsulated" means enclosed by a membrane (e.g., membrane of the polymersome of the present invention, e.g., embodied inside the lumen of said polymersome). With reference to an antigen the term "encapsulated" further means that said antigen is neither integrated into- nor covalently bound to- nor conjugated to said membrane (e.g., of a polymersome of the present invention). With reference to compartmentalization of the vesicular structure of polymersome as described herein the term "encapsulated" means that the inner vesicle is completely contained inside the outer vesicle and is surrounded by the vesicular membrane of the outer vesicle. The confined space surrounded by the vesicular membrane of the outer vesicle forms one compartment. The confined space surrounded by the vesicular membrane of the inner vesicle forms another compartment.

In the present context, the term "antigen" means any substance that may be specifically bound by components of the immune system. Only antigens that are capable of eliciting (or evoking or inducing) an immune response are considered immunogenic and are called "immunogens". Exemplary non-limiting antigens are polypeptides derived from a soluble portion of proteins, hydrophobic polypeptides rendered soluble for encapsulation as well as aggregated polypeptides that are soluble as aggregates. The antigen may originate from within the body ("self-antigen") or from the external environment ("non-self").

Membrane proteins form a class of antigens that typically produce a low immune response level. Of specific interest, soluble (e.g., solubilized) membrane proteins (MPs) and membrane-associated peptides (MAPs) and fragments (i.e., portions) thereof (e.g., the antigens mentioned herein) are encapsulated by a polymersome, which may allow them to be folded in a physiologically relevant manner. This greatly boosts the immunogenicity of such antigens so that when compared to free antigens, a smaller amount of the corresponding antigen can be used to produce the same level of the immune response. Furthermore, the larger size of the polymersomes (compared to free membrane proteins) allows them to be detected by the immune system more easily.

In the present context, the term "B16 peptide" refers to any neoantigen polypeptide derived from the spontaneous C57BL/6-derived B16 melanoma model (e.g., melanoma B16-F10 mouse model). Non-limiting examples thereof include the peptides of SEQ ID NO: 9, 10 and 11.

In the present context, the term "MC38 peptide" refers to any neoantigen polypeptide derived from the colon cancer MC38 mouse model. Non-limiting examples thereof include the peptides of SEQ ID NO: 1, 2 and 3.

In the present context, the term "Influenza hemagglutinin (HA)" refers to a glycoprotein found on the surface of influenza viruses. HA has at least 18 different antigens, which are all within the scope of the present invention. These subtypes are named H1 through H18. Non-limiting examples of "Influenza hemagglutinin (HA)" subtype H1 include the polypeptides of SEQ ID NOs: 5, 6, 7 and 8.

In the present context, the term "Swine Influenza hemagglutinin (HA)" refers to a glycoprotein found on the surface of swine influenza viruses, which is a family of influenza viruses endemic in pigs. Non-limiting examples of "Swine Influenza hemagglutinin (HA)" include subtype H1 of SEQ ID NO: 6.

Figure 12:
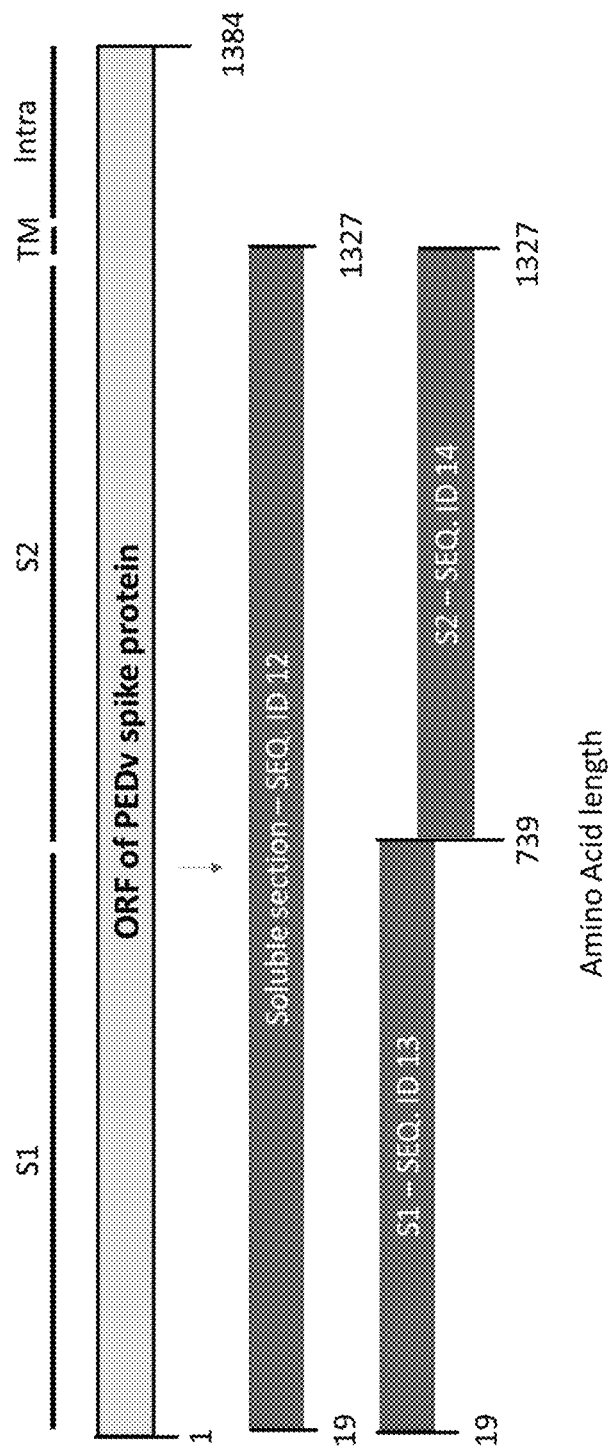
FIG. 12 shows a schematic representation of the Porcine Epidemic Diarrhea virus (PEDv) Spike protein (S Protein) (UniProtKB Accession number: V5TA78) and the soluble fragments of SEQ ID NO: 12 (amino acid residues 19 to 1327), SEQ ID NO: 13 (amino acid residues 19 to 739) and SEQ ID NO: 14 (amino acid residues 739 to 1327) that have been used for the encapsulation of soluble S Protein in polymersomes and subsequent immunization/vaccination of mice and pigs as described herein.

In the present context, the term "PEDv S Protein" refers to SPIKE glycoprotein present on the surface of Porcine epidemic diarrhea virus (PEDV), which is a family of coronavirus in pigs. Non-limiting examples of soluble "PEDv S Protein" as may be used in the present invention include the entire soluble fragment consisting of the S1 and S2 region having the amino acid sequence of SEQ ID NO: 12, the soluble fragment of the S1 region of SEQ ID NO: 13, or the soluble fragment of the S2 region of SEQ ID NO: 14, of the Porcine Epidemic Diarrhea virus (PEDv) Spike protein (S Protein) (UniProtKB Accession number: V5TA78). It is of course also possible to use shorter fragments of the entire soluble fragment of the S1 and the S2 region or of either of the S1 or S2 regions alone (cf. FIG. 12 in this respect) It is of course also possible to use in polymersomes of the present invention a fragment that contains part of the S1 and part of the S2, say for example, amino acids 500 to 939 of the deposited sequence of the Spike protein. It is also noted here that a polymersome of the present invention may have encapsulated one or more different soluble fragments of the Spike protein, for example, the S1 region, the S2 region and/or the entire S1 and S2 region. In illustrative embodiments of a polymersomes of the invention, it has encapsulated therein one type of soluble fragments (for example, only the S1 region), two different types of soluble fragments (for example, the S1 and S2 region), three different types of soluble fragments (the S1 region, the S2 region and the entire soluble fragment of S1 and S2 of SEQ ID NO: 12 (amino acid residues 19 to 1327)) or even four different types of fragments (for example, the S1 region, the S2 region, the entire soluble fragment of S1 and S2 of SEQ ID NO: 12 (amino acid residues 19 to 1327) and as fourth type, the above-mentioned fragment that contains part of the S1 and part of the S2, say for example, amino acids 500 to 939 of the Spike protein sequence). It is also noted here that a polymersome of the present invention having encapsulated one or more different soluble fragments of the Spike protein are used in one preferred embodiment as oral vaccine against the Porcine Epidemic Diarrhea virus.

In the present context, the term "oxidation-stable" refers to a measure of polymersomes (or the corresponding polymers or membranes) resistance to oxidation, for example, using the method described by Scott et al., 2012, In this method a polymersome with an encapsulated antigen is incubated in a 0.5% solution of hydrogen peroxide and the amount of free (released) antigen can be quantified with UV/fluorescence HPLC. Polymersomes which release a substantial or all of the encapsulated antigen under these oxidizing conditions are considered to be oxidation sensitive. Another method of determining whether a blockcopolymer and thus the resulting polymersome is oxidation stable or oxidation-sensitive is described in column 16 of U.S. Pat. No. 8,323,696. According to this method, polymers with functional groups that are oxidation-sensitive will be chemically altered by mild oxidizing agents, with a test for the same being enhanced solubility to 10% hydrogen peroxide for 20 h in vitro. As, for example, poly(propylene sulfide) (PPS) is an oxidation-sensitive polymer (see, for example, Scott et al 2012, supra and U.S. Pat. No. 8,323, 696) PPS can serve as a reference to determine whether a polymer of interest and the respective polymersome of interest is oxidation-sensitive or oxidation stable, If, for example, the same or a higher amount of antigen, or about 90% or more of the amount, or about 80% or more, or about 70% or more, or about 60% or more is released from polymersomes of interest as it is from a PPS polymersome that has encapsulated therein the same antigen, then the polymersome is considered oxidation sensitive. If about only 0.5% or less, or about only 1.0% or less, or about 2% or less, or about 5°/® of less, or about 10% or less, or about 20% or less, or about 30% or less, or about 40% or less or about 50% or less of antigen is released from polymersomes of interest as it is from a PPS polymersome that has encapsulated therein the same antigen, then the polymersome is considered oxidation-stable. Thus, in line with this, PPS polymersomes as described in U.S. Pat. No. 8,323,696 or. PPS-bl-PEG polymersomes, e.g., made from poly(propylene sulfide) (PPS) and poly(ethylene glycol) (PEG) as components as described in Stano et al, are not oxidation-stable polymersomes within the meaning of the present invention. Similarly, PPS30-PEG17 polymersomes are not oxidation-stable polymersomes within the meaning of the present invention. Other non-limiting examples of measuring oxidation stability include measurement of stability in the presence of serum components (e.g., mammalian serum, e.g., human serum components) or stability inside an endosome, for example.

In the present context, the term "reduction-stable" refers to a measure of polymersome resistance to reduction in a reducing environment.

In the present context, the term "serum" refers to blood plasma from which the clotting proteins have been removed.

In the present context, the term "oxidation-independent release" refers to a release of the polymersome content without or essentially without oxidation of the polymers forming the polymersomes.

The term "polypeptide" is equally used herein with the term "protein". Proteins (including fragments thereof, preferably biologically active fragments, and peptides, usually having less than 30 amino acids) comprise one or more amino acids coupled to each other via a covalent peptide bond (resulting in a chain of amino acids). The term "polypeptide" as used herein describes a group of molecules, which, for example, consist of more than 30 amino acids. Polypeptides may further form multimers such as dimers, trimers and higher oligomers, i.e. consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a heteromultimer is an antibody molecule, which, in its naturally occurring form, consists of two identical light polypeptide chains and two identical heavy polypeptide chains. The terms "polypeptide" and "protein" also refer to naturally modified polypeptides/proteins wherein the modification is effected e.g. by post-translational modifications like glycosylation, acetylation, phosphorylation and the like. Such modifications are well known in the art.

In the present context, the term "carbohydrates" refers to compounds such as aldoses and ketoses having the stoichiometric formula $Cn(H2O)n$ (e.g., hence "hydrates of carbon"). The generic term "carbohydrate" includes, but is not limited to, monosaccharides, oligosaccharides and polysaccharides as well as substances derived from monosaccharides by reduction of the carbonyl group (alditols), by oxidation of one or more terminal groups to carboxylic acids, or by replacement of one or more hydroxy group(s) by a hydrogen atom, an amino group, thiol group or similar groups. It also includes derivatives of these compounds.

In the present context, the term "polynucleotide" (also "nucleic acid", which can be used interchangeably with the term "polynucleotide") refers to macromolecules made up of nucleotide units which e.g., can be hydrolysable into certain pyrimidine or purine bases (usually adenine, cytosine, guanine, thymine, uracil), d-ribose or 2-deoxy-d-ribose and phosphoric acid. Non-limiting examples of "polynucleotide" include DNA molecules (e.g. cDNA or genomic DNA), RNA (mRNA), combinations thereof or hybrid molecules comprised of DNA and RNA. The nucleic acids can be double- or single-stranded and may contain double- and single-stranded fragments at the same time. Most preferred are double stranded DNA molecules and mRNA molecules.

In the present context, the term "antisense oligonucleotide" refers to a nucleic acid polymer, at least a portion of which is complementary to a nucleic acid which is present in a normal cell or in an affected cell. Exemplary "antisense oligonucleotide" include antisense RNA, siRNA, RNAi.

In the present context, the term "CD8(+) T cell-mediated immune response" refers to the immune response mediated by cytotoxic T cells (also known as TC, cytotoxic T lymphocyte, CTL, T-killer cells, cytolytic T cells, CD8(+) T-cells or killer T cells). Example of cytotoxic T cells include, but are not limited to antigen-specific effector CD8(+) T cells. In order for the T-cell receptors (TCR) to bind to the class I MHC molecule, the former must be accompanied by a glycoprotein called CD8, which binds to the constant portion of the class I MHC molecule. Therefore, these T cells are called CD8(+) T cells. Once activated, the TC cell undergoes "clonal expansion" with the help of the cytokine Interleukin-2 (IL-2), which is a growth and differentiation factor for T cells. This increases the number of cells specific for the target antigen that can then travel throughout the body in search of antigen-positive somatic cells.

In the present context, the term "clonal expansion of antigen-specific CD8(+) T cells" refers to an increase in the number of CD8(+) T cells specific for the target antigen.

In the present context, the term "cellular immune response" refers to an immune response that does not involve antibodies, but rather involves the activation of phagocytes, antigen-specific cytotoxic T-lymphocytes, and the release of various cytokines in response to an antigen.

In the present context, the term "cytotoxic phenotype of antigen-specific CD8(+) T cells" refers to the set of observable characteristics of antigen-specific CD8(+) T cells related to their cytotoxic function.

In the present context, the term "lymph node-resident macrophages" refers to macrophages, which are large white blood cell that is an integral part of our immune system that use the process of phagocytosis to engulf particles and then digest them, present in lymph nodes that are small, bean-shaped glands throughout the body.

In the present context, the term "humoral immune response" refers to an immune response mediated by macromolecules found in extracellular fluids such as secreted antibodies, complement proteins, and certain antimicrobial peptides. Its aspects involving antibodies are often called antibody-mediated immunity.

In the present context, the term "B cells", also known as B lymphocytes, are a type of white blood cell of the lymphocyte subtype. They function in the humoral immunity component of the adaptive immune system by secreting antibodies.

An "antibody" when used herein is a protein comprising one or more polypeptides (comprising one or more binding domains, preferably antigen binding domains) substantially or partially encoded by immunoglobulin genes or fragments of immunoglobulin genes. The term "immunoglobulin" (Ig) is used interchangeably with "antibody" herein. The recognized immunoglobulin genes include the kappa, lambda, alpha, gamma, delta, epsilon and mu constant region genes, as well as myriad immunoglobulin variable region genes. In particular, an "antibody" when used herein, is typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., IgG1, IgG2, IgG3, IgG4, IgA1, and IgA2, with IgG being preferred in the context of the present invention. An antibody relating to the present invention is also envisaged which has an IgE constant domain or portion thereof that is bound by the Fc epsilon receptor I. An IgM antibody consists of 5 of the basic heterotetramer unit along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each light chain includes an N-terminal variable (V) domain (VL) and a constant (C) domain (CL). Each heavy chain includes an N-terminal V domain (VH), three or four C domains (CHs), and a hinge region. The constant domains are not involved directly in binding an antibody to an antigen, but can exhibit various effector functions, such as participation of the antibody dependent cellular cytotoxicity (ADCC). If an antibody should exert ADCC, it is preferably of the IgG1 subtype, while the IgG4 subtype would not have the capability to exert ADCC.

The term "antibody" also includes, but is not limited to, but encompasses monoclonal, monospecific, poly- or multispecific antibodies such as bispecific antibodies, humanized, camelized, human, single-chain, chimeric, synthetic, recombinant, hybrid, mutated, grafted, and in vitro generated antibodies, with chimeric or humanized antibodies being preferred. The term "humanized antibody" is commonly defined for an antibody in which the specificity encoding CDRs of HC and LC have been transferred to an appropriate human variable frameworks ("CDR grafting"). The term "antibody" also includes scFvs, single chain antibodies, diabodies or tetrabodies, domain antibodies (dAbs) and nanobodies. In terms of the present invention, the term "antibody" shall also comprise bi-, tri- or multimeric or bi-, tri- or multifunctional antibodies having several antigen binding sites.

Furthermore, the term "antibody" as employed in the invention also relates to derivatives of the antibodies (including fragments) described herein. A "derivative" of an antibody comprises an amino acid sequence which has been altered by the introduction of amino acid residue substitutions, deletions or additions. Additionally, a derivative encompasses antibodies which have been modified by a covalent attachment of a molecule of any type to the antibody or protein. Examples of such molecules include sugars, PEG, hydroxyl-, ethoxy-, carboxy- or amine-groups but are not limited to these. In effect the covalent modifications of the antibodies lead to the glycosylation, pegylation, acetylation, phosphorylation, amidation, without being limited to these.

The antibody relating to the present invention is preferably an "isolated" antibody. "Isolated" when used to describe antibodies disclosed herein, means an antibody that has been identified, separated and/or recovered from a component of its production environment. Preferably, the isolated antibody is free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated antibody will be prepared by at least one purification step.

The term "essentially non-immunogenic" means that the block copolymer or amphiphilic polymer of the present invention does not elicit an adaptive immune response, i.e., in comparison to an encapsulated immunogen, the block copolymer or amphiphilic polymer shows an immune response of less than 30%, preferably 20%, more preferably 10%, particularly preferably less than 9, 8, 7, 6 or 5%.

The term "essentially non-antigenic" means that the block copolymer or amphiphilic polymer of the present invention does not bind specifically with a group of certain products that have adaptive immunity (e.g., T cell receptors or antibodies), i.e., in comparison to an encapsulated antigen the block copolymer or amphiphilic polymer shows binding of less than 30%, preferably 20%, more preferably 10%, particularly preferably less than 9, 8, 7, 6 or 5%.

Typically, binding is considered specific when the binding affinity is higher than $10^{-6}$M. Preferably, binding is considered specific when binding affinity is about $10^{-11}$ to $10^{-8}$ M (KD), preferably of about $10^{-11}$ to $10^{-9}$ M. If necessary, nonspecific binding can be reduced without substantially affecting specific binding by varying the binding conditions.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (He or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gln, Gly, His, Met, Phe, Ser, Thr, Trp, and Tyr).

"Polyclonal antibodies" or "polyclonal antisera" refer to immune serum containing a mixture of antibodies specific for one (monovalent or specific antisera) or more (polyvalent antisera) antigens which may be prepared from the blood of animals immunized with the antigen or antigens.

Furthermore, the term "antibody" as employed in the invention also relates to derivatives or variants of the antibodies described herein which display the same specificity as the described antibodies. Examples of "antibody variants" include humanized variants of non-human antibodies, "affinity matured" antibodies (see, e.g. Hawkins et al. J. Mol. Biol. 254, 889-896 (1992) and Lowman et al., Biochemistry 30, 10832-10837 (1991)) and antibody mutants with altered effector function (s) (see, e.g., U.S. Pat. No. 5,648,260).

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any method. For example, the monoclonal antibodies to be used in accordance with the present invention may be made by the hybridoma method first described by Kohler et al., Nature, 256: 495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352: 624-628 (1991) and Marks et al., J. Mol. Biol., 222: 581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain (s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Chimeric antibodies of interest herein include "primitized" antibodies comprising variable domain antigen-binding sequences derived from a non-human primate (e.g., Old World Monkey, Ape etc.) and human constant region sequences.

"Humanized" forms of non-human (e.g., murine) antibodies are chimeric immunoglobulins, immunoglobulin chains or fragments thereof (such as Fv, Fab, Fab', F (ab') 2 or other antigen-binding subsequences of antibodies) of mostly human sequences, which contain minimal sequence derived from non-human immunoglobulin. For the most part, humanized antibodies are human immunoglobulins (recipient antibody) in which residues from a hypervariable region (also CDR) of the recipient are replaced by residues from a hypervariable region of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody optimally also will comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992).

The term "human antibody" includes antibodies having variable and constant regions corresponding substantially to human germline immunoglobulin sequences known in the art, including, for example, those described by Kabat et al. (See Kabat, et al. (1991) loc. cit.). The human antibodies of the invention may include amino acid residues not encoded by human germline immunoglobulin sequences (e.g., mutations introduced by random or site-specific mutagenesis in vitro or by somatic mutation in vivo), for example in the CDRs, and in particular, CDR3. The human antibody can have at least one, two, three, four, five, or more positions replaced with an amino acid residue that is not encoded by the human germline immunoglobulin sequence.

As used herein, "in vitro generated antibody" refers to an antibody where all or part of the variable region (e.g., at least one CDR) is generated in a non-immune cell selection (e.g., an in vitro phage display, protein chip or any other method in which candidate sequences can be tested for their ability to bind to an antigen). This term thus preferably excludes sequences generated by genomic rearrangement in an immune cell.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). In one embodiment, the bispecific antibody comprises a first binding domain polypeptide, such as a Fab' fragment, linked via an immunoglobulin constant region to a second binding domain polypeptide.

Numerous methods known to those skilled in the art are available for obtaining antibodies or antigen-binding fragments thereof. For example, antibodies can be produced using recombinant DNA methods (U.S. Pat. No. 4,816,567). Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) Nature Genetics 7:13-21, US 2003-0070185, WO 96/34096, and WO96/33735.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See e.g., Morrison et al., Proc. Natl. Acad. ScL U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., EP 171496; EP 173494, GB 2177096. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) Science 229:1202-1207; by Oi et al. (1986) BioTechniques 4:214; and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., Proc. Natl. Acad. Sci. U.S.A., 80: 7308-7312, 1983; Kozbor et al, Immunology Today, 4: 7279, 1983; Olsson et al., Meth. Enzymol., 92: 3-16, 1982), and may be made according to the teachings of WO 92/06193 or EP 239400).

An antibody or fragment thereof may also be modified by specific deletion of human T cell epitopes or "deimmunization" by the methods disclosed in WO 98/52976 and WO 00/34317. Briefly, the heavy and light chain variable domains of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences, e.g., are disclosed in Tomlinson, et at. (1992) J. Mol. Biol. 227:776-798; Cook, G. P. et al. (1995) Immunol. Today Vol. 16 (5): 237-242; Chothia, et al. (1992) J. Mol. Biol. 227: 799-817; and Tomlinson et al. (1995) EMBO J. 14:4628-4638. The V BASE directory provides a comprehensive directory of human immunoglobulin variable region sequences (compiled by Tomlinson, L A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

"Effector cells", preferably human effector cells are leukocytes which express one or more FcRs and perform effector functions. Preferably, the cells express at least FcyRm and perform ADCC effector function. Examples of human leukocytes which mediate ADCC include peripheral blood mononuclear cells (PBMC), natural killer (NK) cells, monocytes, cytotoxic T cells and neutrophils. The effector cells may be isolated from a native source, e.g., blood.

Techniques for production of antibodies, including polyclonal, monoclonal, humanized, bispecific and heteroconjugate antibodies are known in the art, some of which are exemplified below.

1) Polyclonal Antibodies.

Polyclonal antibodies are generally raised in animals by multiple subcutaneous (sc) or intraperitoneal (ip) injections of the relevant antigen (e.g., encapsulated in a polymersome) and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysien residues), glutaraldehyde, succinic anhydride. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

For example, the animals are immunized against the antigen, immunogenic conjugates, or derivatives by combining the protein or conjugate (for rabbits or mice, respectively) with 3 volumes of Freund's complete adjuvant and injecting the solution intradermally at multiple sites. One month later, the animals are boosted with ⅕ to ⅟₁₀ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable used to enhance the immune response.

The term "immunizing" refers to the step or steps of administering one or more antigens to a non-human animal so that antibodies can be raised in the animal.

Specifically, the non-human animal is preferably immunized at least two, more preferably three times with said polypeptide (antigen), optionally in admixture with an adjuvant. An "adjuvant" is a nonspecific stimulant of the immune response. The adjuvant may be in the form of a composition comprising either or both of the following components: (a) a substance designed to form a deposit protecting the antigen (s) from rapid catabolism (e.g. mineral oil, alum, aluminium hydroxide, liposome or surfactant (e.g. pluronic polyol) and (b) a substance that nonspecifically stimulates the immune response of the immunized host animal (e.g. by increasing lymphokine levels therein).

Exemplary molecules for increasing lymphokine levels include lipopolysaccharide (LPS) or a Lipid A portion thereof; Bordetalla *pertussis; pertussis* toxin; *Mycobacterium tuberculosis*; and muramyl dipeptide (MDP). Examples of adjuvants include Freund's adjuvant (optionally comprising killed *M. tuberculosis*; complete Freund's adjuvant); aluminium hydroxide adjuvant; and monophosphoryl Lipid A-synthetic trehalose dicorynomylcolate (MPL-TDM).

The "non-human animal" to be immunized herein is preferably a rodent. A "rodent" is an animal belonging to the rodentia order of placental mammals. Exemplary rodents include mice, rats, guinea pigs, squirrels, hamsters, ferrets etc, with mice being the preferred rodent for immunizing according to the method herein. Other non-human animals which can be immunized herein include non-human primates such as Old World monkey (e.g. baboon or macaque, including Rhesus monkey and cynomolgus monkey; see U.S. Pat. No. 5,658,570); birds (e.g. chickens); rabbits; goats; sheep; cows; horses; pigs; donkeys; dogs etc.

By "screening" is meant subjecting one or more monoclonal antibodies (e.g., purified antibody and/or hybridoma culture supernatant comprising the antibody) to one or more assays which determine qualitatively and/or quantitatively the ability of an antibody to bind to an antigen of interest.

By "immuno-assay" is meant an assay that determines binding of an antibody to an antigen, wherein either the antibody or antigen, or both, are optionally adsorbed on a solid phase (i. e., an "immunoadsorbent" assay) at some stage of the assay. Exemplary such assays include ELISAs, radioimmunoassays (RIAs), and FACS assays. Given the above, the present invention provides thus a monoclonal or polyclonal antibody obtainable by the aforedescribed methods for the generation of an antibody, i.e., by immunizing a non-human animal as described before.

2) Monoclonal Antibodies.

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies. For example, the monoclonal antibodies may be made using the hybridoma method first described by Kohler et al., Nature, 256: 495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization.

Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986).

The immunizing agent will typically include the antigenic protein or a fusion variant thereof. Generally either peripheral blood lymphocytes ("PBLs") are used if cells of human origin are desired, or spleen cells or lymph node cells are used if non-human mammalian sources are desired. The lymphoctyes are then fused with an immortalized cell line using a suitable fusing agent, such as polyethylene glycol, to form a hybridoma cell. Goding, Monoclonal Antibodies: Principles and Practice, Academic Press (1986), pp. 59-103.

Immortalized cell lines are usually transformed mammalian cell, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor, J. Immunol., 133: 3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The culture medium in which the hybridoma cells are cultured can be assayed for the presence of monoclonal antibodies directed again desired antigen. Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., Anal. Biochem., 107: 220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as ascites tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., Curr. Opinion in Immunol., 5: 256-262 (1993) and Pluckthun, Immunol. Revs. 130: 151-188 (1992).

3) Humanized Antibodies

The antibodies of the invention may further comprise humanized or human antibodies. Humanized forms of non-human (e.g., murine) antibodies are chimeric immunoglobulins, immunoglobulin chains or fragments thereof (such as Fv, Fab, Fab', F (ab') 2 or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues.

Humanized antibodies may also comprise residues which are found neither in the recipient antibody nor in the imported CDR or framework sequences. In general, the humanized antibody will comprise substantially all of at least one, and typically two, variable domain, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. Jones et al., Nature 321: 522-525 (1986); Riechmann et al., Nature 332: 323-329 (1988) and Presta, Curr. Opin. Struct. Biol. 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., Nature 321: 522-525 (1986); Riechmann et al., Nature 332: 323-327 (1988); Verhoeyen et al., Science 239: 1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., J. Immunol.) 151: 2296 (1993); Chothia et al., J. Mol. Biol., 196: 901 (1987).

Another method uses a particular framework derived from the consensus sequence of all human antibodies of a particular subgroup of light or heavy chains. The same framework may be used for several different humanized antibodies. Carter et al., Proc. Natl. Acad. Sci. USA, 89: 4285 (1992); Presta et al., J. Immunol., 151: 2623 (1993).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen (s), is achieved. In general, the CDR residues are directly and most substantially involved in influencing antigen binding.

Various forms of the humanized antibody are contemplated. For example, the humanized antibody may be an antibody fragment, such as an Fab, which is optionally conjugated with one or more cytotoxic agent (s) in order to generate an immunoconjugate.

Alternatively, the humanized antibody may be an intact antibody, such as an intact IgGI antibody.

4) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255-258 (1993); Bruggermann et al., Year in Immun., 7: 33 (1993); U.S. Pat. No. 5,591,669 and WO 97/17852.

Alternatively, phage display technology can be used to produce human antibodies and antibody fragments in vitro, from immunoglobulin variable (V) domain gene repertoires from unimmunized donors. McCafferty et al., Nature 348: 552-553 (1990); Hoogenboom and Winter, J. Mol. Biol. 227: 381 (1991). According to this technique, antibody V domain genes are cloned in-frame into either a major or minor coat protein gene of a filamentous bacteriophage, such as M13, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., Curr. Opin Struct. Biol. 3: 564-571 (1993). Several sources of V-gene segments can be used for phage display. Clackson et al., Nature 352: 624-628 (1991) isolated a diverse array of anti-oxazolone antibodies from a small random combinatorial library of V genes derived from the spleens of immunized mice. A repertoire of V genes from unimmunized hman donors can be constructed and antibodies to a diverse array of antigens (including self-antigens) can be isolated essentially following the techniques described by Marks et al., J. Mol. Biol. 222: 581-597 (1991), or Griffith et al., EMBO J. 12: 725-734 (1993). See also, U.S. Pat. Nos. 5,565,332 and 5,573,905.

The techniques of Cole et al., and Boerner et al., are also available for the preparation of human monoclonal antibodies (Cole et al., Monoclonal Antibodies and Cancer Therapy, Alan R. Liss, p. 77 (1985) and Boerner et al., J. Immunol. 147 (1): 86-95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resemble that seen in human in all respects, including gene rearrangement, assembly and antibody repertoire. This approach is described, for example, in U.S. Pat. Nos. 5,545,807; 5,545,806, 5,569,825, 5,625,126, 5,633,425, 5,661,016 and in the following scientific publications: Marks et al., Bio/Technology 10: 779-783 (1992); Lonberg et al., Nature 368: 856-859 (1994); Morrison, Nature 368: 812-13 (1994), Fishwild et al., Nature Biotechnology 14: 845-51 (1996), Neuberger, Nature Biotechnology 14: 826 (1996) and Lonberg and Huszar, Intern. Rev. Immunol. 13: 65-93 (1995). Finally, human antibodies may also be generated in vitro by activated B cells (see U.S. Pat. Nos. 5,567,610 and 5,229,275).

5) Bispecific and polyspecific antibodies

Bispecific antibodies (BsAbs) are antibodies that have binding specificities for at least two different epitopes, including those on the same or another protein. Alternatively, one arm can be armed to bind to the target antigen, and another arm can be combined with an arm that binds to a triggering molecule on a leukocyte such as a T-cell receptor molecule (e.g., CD3), or Fc receptors for IgG (FcγR) such as FcγRI (CD64), FcγRII (CD32) and FcγRin (CD16), so as to focus and localize cellular defense mechanisms to the target antigen-expressing cell. Such antibodies can be derived from full length antibodies or antibody fragments (e.g. F(ab')$_2$ bispecific antibodies).

Bispecific antibodies may also be used to localize cytotoxic agents to cells which express the target antigen. Such antibodies possess one arm that binds the desired antigen and another arm that binds the cytotoxic agent (e.g., methotrexate).

Methods for making bispecific antibodies are known in the art. Traditional production of full length bispecific antibodies is based on the coexpression of two immunoglobulin heavy chain-light chain pairs, where the two chains have different specificities. Millstein et al., Nature, 305: 537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., EMBO J., 10: 3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecules provides for an easy way of separation. This approach is disclosed in WO 94/04690. For further details of generating bispecific antibodies, see, for example, Suresh et al., Methods in Enzymology 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chains (s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., Science 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab'fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175: 217-225 (1992) describes the production of fully humanized bispecific antibody F (ab') 2 molecules. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., J. Immunol., 148 (5): 1547-1553 (1992).

The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., Proc. Natl. Acad. Sci. USA, 90: 6444-6448 (1993) has provided an alternative mechanism for making bispecific/bivalent antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific/bivalent antibody fragments by the use of single-chain Fv (sFv) dimers has also been reported. See Gruber et al., J. Imnzunol., 152: 5368 (1994).

Antibodies with more than two valencies are contemplated. For example, trispecific antibodies can be prepared. Tutt et al., J. Immunol. 147: 60 (1991).

Exemplary bispecific antibodies may bind to two different epitopes on a given molecule. Alternatively, an anti-protein arm may be combined with an arm which binds to a triggering molecule on a leukocyte such as a T-cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein.

Another bispecific antibody of interest binds the protein of interest and further binds Human Serum Albumin.

The "diabody" technology described by Hollinger et al., Proc. Natl. Acad. Sci. USA, 90: 6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152: 5368 (1994).

Antibodies with more than two valencies are contemplated. For example, trispecific antibodies can be prepared. Tutt et al. J. Immunol. 147: 60 (1991).

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain (s) comprise two or more variable domains. For instance, the polypeptide chain (s) may comprise VDI (X1$_n$-VD2-(X2)n-Fc, wherein VDI is a first variable domain, VD2 is a second variable domain, Fc is one polypeptide chain of an Fc region, X1 and X2 represent an amino acid or polypeptide, and n is 0 or 1. For instance, the polypeptide chain (s) may comprise: VH-CHI-flexible linker-VH-CHI-Fc region chain; or VH-CHI-VH-CHI-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Heteroconjugate antibodies are also within the scope of the present invention.

Heteroconjugate antibodies are composed of two covalently joined antibodies. For example, one of the antibodies in the heteroconjugate can be coupled to avidin, the other to biotin. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

For additional antibody production techniques, see Antibodies: A Laboratory Manual, eds. Harlow et al., Cold Spring Harbor Laboratory, 1988. The present invention is not necessarily limited to any particular source, method of production, or other special characteristics of an antibody.

The antibody relating to the present invention is preferably an "isolated" antibody. "Isolated" when used to describe antibodies disclosed herein, means an antibody that has been identified, separated and/or recovered from a component of its production environment. Preferably, the isolated antibody is free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated antibody will be prepared by at least one purification step.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

Non-limiting examples of cancers include squamous cell carcinoma, small-cell lung cancer, non-small cell lung cancer, squamous non-small cell lung cancer (NSCLC), non NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of luekemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukaemia (T-Lbly/T-ALL), peripheral T-cell lymphoma, lymphoblastic lymphoma, post-transplantation, lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary, plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein may also be used for treatment of metastatic cancers, refractory cancers (e.g., cancers refractory to previous immunotherapy, e.g., with a blocking CTA-4 or PD-1 or PD-L1 antibody), and recurrent cancers.

The term "subject" is intended to include living organisms. Examples of subjects include mammals, e.g., humans, dogs, cows, horses, pigs, sheep, goats, cats, mice, rabbits, rats, and transgenic non-human animals. The subject (animal) can however be a non-mammalian animal such as a bird or a fish. In some preferred embodiments of the invention, the subject is a human, while in other some other preferred embodiments, the subject might be a farm animal, wherein the farm animal can be either a mammal or a non-mammalian animal. Examples of such non-mammalian animals are birds (e.g. poultry such as chicken, duck, goose or turkey), fishes (for example, fishes cultivated in aquaculture such as salmon, trout, or tilapia) or crustacean (such as shrimps or prawns). Examples of mammalian (life stock) animals includes goats; sheep; cows; horses; pigs; or donkeys. Other mammals include cats, dogs, mice and rabbits, for example. In illustrative embodiments the polymersomes of the present invention are used for the vaccination or immunization of the above-mentioned farm animals, both mammalian farm animals and non-mammalian farm animals (a bird, a fish, a crustacean) against virus infections (cf. the Example section in this regard). Accordingly, in such cases, polymersomes of the invention may have encapsulated therein soluble viral full length proteins or soluble fragments of viral full-length proteins.

When used for vaccinations of both humans and non-humans animals, polymersomes or compositions comprising polymersomes of the invention may be administered orally to the respective subject (cf. also the Example Section) dissolved only in a suitable (pharmaceutically acceptable) buffer such as phosphate-buffered saline (PBS) or 0.9% saline solution (an isotonic solution of 0.90% w/v of NaCl, with an osmolality of 308 mOsm/L). Alternatively, the polymersomes can be modified, for example, by a coating with natural polymers or can be formulated in particles of natural polymers such as alginate or chitosan or of synthetic polymers such as as poly(d,l-lactide-co-glycolide) (PLG), poly(d,l-lactic-coglycolic acid)(PLGA), poly(g-glutamicacid) (g-PGA) [31,32] or poly(ethylene glycol) (PEG). These particles can either be particles in the micrometer range ("macrobeads") or nanoparticles, or nanoparticles incorporated into macobeads all of which are well known in the art. See, for example. Han et al, "Chitosan/calcium-alginate beads for oral delivery of insulin", Applied Polymer Science, Volume 59, Issue11, 14 Mar. 1996, 1795-1801, the review of Sosnik "Alginate Particles as Platform for Drug Delivery by the Oral Route: State-of-the-Art" ISRN Pharmaceutics Volume 2014, Article ID 926157, Machado et al, Encapsulation of DNA in Macroscopic and Nanosized Calcium Alginate Gel Particles", Langmuir 2013, 29, 15926-15935, International Pat. Application WO 2015/110656, the review "Nanoparticle vaccines" of Liang Zhao et al. Vaccine 32 (2014) 327-337) or Li et al "Chitosan-Alginate Nanoparticles as a Novel Drug Delivery System for Nifedipine" Int J Biomed Sci vol. 4 no. 3 Sep. 2008, 221-228. In illustrative embodiments of these polymersomes and oral formulations, the polymersomes that are used for vaccination have encapsulated therein a viral antigen that comprises a soluble portion of Influenza hemagglutinin, Swine Influenza hemagglutinin, Foot and Mouth Disease (FMD) virus protein such as the VP1, VP2 or VP3 coat protein (the VP1 coat protein contains the main antigenic determinants of the FMD virion, and hence changes in its sequence should be responsible for the high antigenic variability of the virus), Ovalbumin (OVA) or of the Porcine epidemic diarrhea (PED) virus SPIKE protein. As evident from the use of polymersomes comprising a soluble portion of the influenza hemagglutinin or a Foot and Mouth Disease (FMD) virus protein such as the VP1, VP2 or VP3 coat protein, the viral disease can affect any animal including birds and mammals, wherein a mammal can also be a human.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the infection and the general state of the subject's own immune system. The term "patient" includes human and other mammalian subjects that receive either prophylactic or therapeutic treatment.

The appropriate dosage, or therapeutically effective amount, of the antibody or antigen binding portion thereof will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations. The pharmaceutical composition can be administered as a sole therapeutic or in combination with additional therapies as needed.

If the pharmaceutical composition has been lyophilized, the lyophilized material is first reconstituted in an appropriate liquid prior to administration. The lyophilized material may be reconstituted in, e.g., bacteriostatic water for injection (BWFI), physiological saline, phosphate buffered saline (PBS), or the same formulation the protein had been in prior to lyophilization.

Pharmaceutical compositions for injection may be presented in unit dosage form, e.g., in ampoules or in multi-dose containers, with an added preservative. In addition, a number of recent drug delivery approaches have been developed and the pharmaceutical compositions of the present invention are suitable for administration using these new methods, e. g., Inject-ease, Genject, injector pens such as Genen, and needleless devices such as MediJector and BioJector. The present pharmaceutical composition can also be adapted for yet to be discovered administration methods. See also Langer, 1990, Science, 249: 1527-1533.

The pharmaceutical composition can also be formulated as a depot preparation. Such long acting formulations may be administered by implantation (for example subcutaneously, into the ligament or tendon, subsynovially or intramuscularly), by subsynovial injection or by intramuscular injection. Thus, for example, the formulations may be modified with suitable polymeric or hydrophobic materials (for example as a emulsion in an acceptable oil) or ion exchange resins, or as sparingly soluble derivatives, for example, as a sparingly soluble salt.

The pharmaceutical compositions may also be in a variety of conventional depot forms employed for administration to provide reactive compositions. These include, for example, solid, semi-solid and liquid dosage forms, such as liquid solutions or suspensions, slurries, gels, creams, balms, emulsions, lotions, powders, sprays, foams, pastes, ointments, salves, balms and drops.

The pharmaceutical compositions may, if desired, be presented in a vial, pack or dispenser device which may contain one or more unit dosage forms containing the active ingredient. In one embodiment, the dispenser device can comprise a syringe having a single dose of the liquid formulation ready for injection. The syringe can be accompanied by instructions for administration.

The pharmaceutical composition may further comprise additional pharmaceutically acceptable components. Other pharmaceutically acceptable carriers, excipients, or stabilizers, such as those described in Remington's Pharmaceutical Sciences 16th edition, Osol, A. Ed. (1980) may also be included in a protein formulation described herein, provided that they do not adversely affect the desired characteristics of the formulation. As used herein, "pharmaceutically acceptable carrier" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are non-toxic to recipients at the dosages and concentrations employed and include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, asparagine, 2-phenylalanine, and threonine; sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone.

The formulations described herein are useful as pharmaceutical compositions in the treatment and/or prevention of the pathological medical condition as described herein in a patient in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

As used herein, the term "treating" and "treatment" refers to administering to a subject a therapeutically effective amount of a pharmaceutical composition according to the invention. A "therapeutically effective amount" refers to an amount of the pharmaceutical composition or the antibody which is sufficient to treat or ameliorate a disease or disorder, to delay the onset of a disease or to provide any therapeutic benefit in the treatment or management of a disease.

As used herein, the term "prophylaxis" refers to the use of an agent for the prevention of the onset of a disease or disorder. A "prophylactically effective amount" defines an amount of the active component or pharmaceutical agent sufficient to prevent the onset or recurrence of a disease.

As used herein, the terms "disorder" and "disease" are used interchangeably to refer to a condition in a subject. In particular, the term "cancer" is used interchangeably with the term "tumor".

The kit of the invention will typically comprise the container described above and one or more other containers comprising materials desirable from a commercial and user standpoint, including buffers, diluents, filters, needles, syringes, and package inserts with instructions for use.

In the present context, the term "liposome" refers to a spherical vesicle having at least one lipid bilayer.

In the present context, the term "endosome" refers to a membrane-bound compartment (i.e., a vacuole) inside eukaryotic cells to which materials ingested by endocytosis are delivered.

In the present context, the term "late-endosome" refers to a pre-lysosomal endocytic organelle differentiated from early endosomes by lower lumenal pH and different protein composition. Late endosomes are more spherical than early endosomes and are mostly juxtanuclear, being concentrated near the microtubule organizing center.

In the present context, the term "T helper cells" (also called TH cells or "effector CD4(+) T cells") refers to T lymphocytes that assist other white blood cells in immunologic processes, including maturation of B cells into plasma cells and memory B cells, and activation of cytotoxic T cells and macrophages. These cells are also known as "CD4(+) T cells" because they express the CD4 glycoprotein on their surfaces. Helper T cells become activated when they are presented with e.g., peptide antigens, by MHC class II molecules, which are expressed on the surface of antigen-presenting cells (APCs).

As used herein, the term "self-antigen" refers to any molecule or chemical group of an organism which acts as an antigen in inducing antibody formation in another organism but to which the healthy immune system of the parent organism is tolerant.

As used herein, the term "% identity" refers to the percentage of identical amino acid residues at the corresponding position within the sequence when comparing two amino acid sequences with an optimal sequence alignment as exemplified by the ClustalW or X techniques as available from www.clustal.org, or equivalent techniques. Accordingly, both sequences (reference sequence and sequence of interest) are aligned, identical amino acid residues between both sequences are identified and the total number of identical amino acids is divided by the total number of amino acids (amino acid length). The result of this division is a percent value, i.e. percent identity value/degree.

An immunization method of the present invention can be carried out using a either a full length soluble encapsulated antigen (e.g., protein) or fragment of the protein in a synthetic environment that allows its proper folding, and therefore the probability of isolating antibodies capable of detecting corresponding antigens (e.g., a membrane protein) in vivo would be higher. Moreover, the immunization and antibody generation can be carried out without any prior knowledge of the membrane protein structure, which may otherwise be necessary when using a peptide-based immunization approach.

Further, when compared to other techniques, the method of the present invention allows for a rapid and cost-effective production of membrane protein encapsulated in an oxidation-stable membrane environment.

In some aspects, the present invention relates to a method for eliciting an immune response to an antigen (e.g., an immunogen) in a subject. The method may include administering to the subject a composition including a polymersome of the present invention having a membrane (e.g., circumferential) of an amphiphilic polymer. The composition further includes a soluble antigen encapsulated by the membrane of the amphiphilic polymer of the polymersome of the present invention. The immunogen may be a membrane-associated protein. In some further aspects, the polymersome of the present invention comprises a lipid polymer. The administration may be carried out in any suitable fashion, for example, by oral administration, topical administration or injection.

The frequency of the administration (e.g. oral administration or injection) may be determined and adjusted by a person skilled in the art, dependent on the level of response desired. For example, weekly or bi-weekly administration (e.g. orally or by injection) of polymersomes of the present invention may be given to the subject, which may include a mammalian animal. The immune response can be measured by quantifying the blood concentration level of antibodies (titres) in the mammalian animal against the initial amount of antigen encapsulated by the polymersome of the present invention (cf., the Example Section).

The structure of the polymersomes may include amphiphilic block copolymers self-assembled into a vesicular format and encapsulating various antigens (e.g., soluble proteins, etc.), that are encapsulated by methods of solvent re-hydration, direct dispersion or by spontaneous self-assembly (e.g., Example 1 as described herein).

In the present context, the term "soluble antigen" as used herein means an antigen capable of being dissolved or liquefied. The term "soluble antigen" includes antigens that were "solubilized", i.e., rendered soluble or more soluble, especially in water, by the action of a detergent or other agent. Exemplary non-limiting soluble antigens of the present invention include: polypeptides derived from a non-soluble portion of proteins, hydrophobic polypeptides rendered soluble for encapsulation as well as aggregated polypeptides that are soluble as aggregates.

In some aspects, the antigens (e.g., membrane proteins) of the present invention are solubilized with the aid of detergents, surfactants, temperature change or pH change. The vesicular structure provided by the amphiphilic block copolymers allows the antigens (e.g., membrane protein) to be folded in a physiologically correct and functional manner, allowing the immune system of the target mammalian animal to detect said antigens, thereby producing a strong immune response.

In some aspects, the injection of the composition of the present invention may include intraperitoneal, subcutaneous, or intravenous, intramuscular injection, or non-invasive administration. In some other aspects, the injection of the composition of the present invention may include intradermal injection.

In some other aspects, the immune response level may be further heightened or boosted by including an adjuvant in the composition including the polymersome of the present invention. In such aspects, the polymersome and the adjuvant can be administered simultaneously to the subject.

In some aspects, a block copolymer or an amphiphilic polymer of the polymersome of the present invention is neither immunostimulant nor adjuvant.

In some other aspects, a block copolymer or an amphiphilic polymer of the polymersome of the present invention is immunostimulant and/or adjuvant.

In some further aspects, a polymersome of the present invention is immunogenic.

In some further aspects, a polymersome of the present invention is non-immunogenic.

In some aspects, the adjuvant may be administered separately from the administration of the composition of the present invention including the polymersome of the present invention. The adjuvant may be administered before, simultaneously, or after the administration of the composition including the polymersome encapsulating an antigen of the present invention. For example, the adjuvant may be injected to the subject after injecting the composition including the polymersome encapsulating an antigen of the present invention. In some aspects, the adjuvant can be encapsulated together with the antigen in the polymersomes.

A person skilled in the art would readily recognize and appreciate that the types of adjuvant to be injected depend on the types of antigen to be injected. The antigen may be an antigen of bacterial, viral, or fungi origin. For example, in the case where the antigen is OVA, the adjuvant may be Sigma Adjuvant System (SAS). Other antigen-adjuvant pairs are also suitable for use in the methods of the present invention. In certain aspects, the use of adjuvants is not needed. In yet other aspects, the present method works better, i.e., stronger immune response being evoked, without the use of adjuvants.

In some aspects, a membrane protein may be a transmembrane protein, G protein-coupled receptor, neurotransmitter receptor, kinase, porin, ABC transporter, ion transporter, acetylcholine receptor and cell adhesion receptor. The membrane proteins may also be fused to or coupled with a tag or may be tag-free. If the membrane proteins are tagged, then the tag may, for example, be selected from well-known affinity tags such as VSV, His-tag, Strep-tag®, Flag-tag, Intein-tag or GST-tag or a partner of a high affinity binding pair such as biotin or avidin or from a label such as a fluorescent label, an enzyme label, NMR label or isotope label.

In some aspects, the membrane proteins of fragments (or portions) thereof may be presented prior to encapsulation, or encapsulated simultaneously with the production of the protein through a cell-free expression system. The cell-free expression system may be an in vitro transcription and translation system.

The cell-free expression system may also be an eukaryotic cell-free expression system such as the TNT system based on rabbit reticulocytes, wheat germ extract or insect extract, a prokaryotic cell-free expression system or an archaic cell-free expression system.

As mentioned above, the polymersomes may be formed of amphiphilic di-block or tri-block copolymers. In various aspects, the amphiphilic polymer may include at least one monomer unit of a carboxylic acid, an amide, an amine, an alkylene, a dialkylsiloxane, an ether or an alkylene sulphide.

In some aspects, the amphiphilic polymer may be a polyether block selected from the group consisting of an oligo(oxyethylene) block, a poly(oxyethylene) block, an oligo(oxypropylene) block, a poly(oxypropylene) block, an oligo(oxybutylene) block and a poly(oxybutylene) block. Further examples of blocks that may be included in the polymer include, but are not limited to, poly(acrylic acid), poly(methyl acrylate), polystyrene, poly(butadiene), poly(2-methyloxazoline), poly(dimethyl siloxane), poly(e-caprolactone), poly(propylene sulphide), poly(N-isopropylacrylamide), poly(2-vinylpyridine), poly(2-(diethylamino)ethyl methacrylate), poly(2-diisopropylamino)ethylmethacrylate), poly(2-methacryloyloxy)ethylphosphorylcholine, poly (isoprene), poly(isobutylene), poly(ethylene-co-butylene) and poly(lactic acid). Examples of a suitable amphiphilic polymer include, but are not limited to, poly(ethyl ethylene)-b-poly(ethylene oxide) (PEE-b-PEO), poly(butadiene)-b-poly(ethylene oxide) (PBD-b-PEO), poly(styrene)-b-poly (acrylic acid) (PS-PAA), poly(dimethylsiloxane)-poly (ethylene oxide (herein called PDMS-PEO) also known as poly(dimethylsiloxane-b-ethylene oxide), poly(2-methyloxazoline)-b-poly(dimethylsiloxane)-b-poly(2-methyloxazoline) (PMOXA-bPDMS-bPMOXA) including for example, triblock copolymers such as $PMOXA_{20}$-$PDMS_{54}$-$PMOXA_{20}$ (ABA) employed by May et al., 2013, poly(2-methyloxazoline)-b-poly(dimethylsiloxane)-b-poly (ethylene oxide) (PMOXA-b-PDMS-b-PEO), poly(ethylene oxide)-b-poly(propylene sulfide)-b-poly(ethylene oxide) (PEO-b-PPS-b-PEO) and a poly(ethylene oxide)-poly(butylene oxide) block copolymer. A block copolymer can be further specified by the average block length of the respective blocks included in a copolymer. Thus, $PB_M PEO_N$ indicates the presence of polybutadiene blocks (PB) with a length of M and polyethyleneoxide (PEO) blocks with a length of N. M and N are independently selected integers, which may for example be selected in the range from about 6 to about 60. Thus, $PB_{35}PEO_{18}$ indicates the presence of polybutadiene blocks with an average length of 35 and of polyethyleneoxide blocks with an average length of 18. In certain aspects, the PB-PEO diblock copolymer comprises 5-50 blocks PB and 5-50 blocks PEO. Likewise, $PB_{10}PEO_{24}$ indicates the presence of polybutadiene blocks with an average length of 10 and of polyethyleneoxide blocks with an average length of 24. Illustrative examples of suitable PB-PEO diblock copolymers that can be used in the present invention include the diblock copolymers $PBD_{21}$-$PEO_{14}$ (that is also commercially available) and $[PBD]_{21}$-$[PEO]_{12}$, (cf, WO2014/077781A1 and Nallani et al., 2011), As a further example $E_O B_P$ indicates the presence of ethylene oxide blocks (E) with a length of O and butadiene blocks (B) with a length of P. Thus, O and P are independently selected integers, e.g. in the range from about 10 to about 120. Thus, $E_{16}E_{22}$ indicates the presence of ethylene oxide blocks with an average length of 16 and of butadiene blocks with an average length of 22.

Turning to another preferred block copolymer that is used to form polymersome of the invention, poly(dimethylsiloxane-b-ethyleneoxide) (PDMS-PEO), it is noted that both linear and comb-type PDMS-PEO can be used herein (cf.

Gaspard et al, "Mechanical Characterization of Hybrid Vesicles Based on Linear Poly(Dimethylsiloxane-b-Ethylene Oxide) and Poly(Butadiene-b-Ethylene Oxide) Block Copolymers" Sensors 2016, 16(3), 390 which describes polymersomes formed from PDMS-PEO).

The structure of linear PDMS-PEO is shown in the following as formula (I)

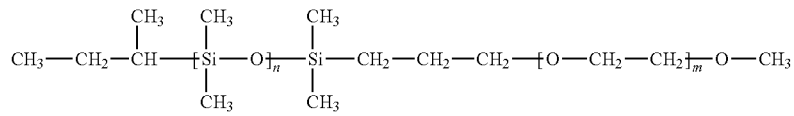

while the structure of comb-type PDMS-PEO is shown in the following formula (II):

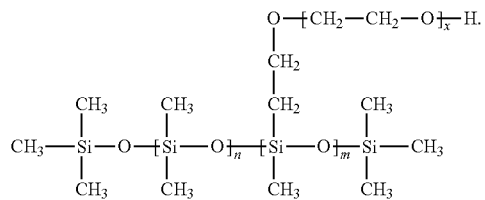

In line with the structural formula (I), the terminology $PDMS_n\text{-}PEO_m$, indicates the presence of polydimethylsiloxane (PDMS) blocks with a length of n and polyethyleneoxide (PEO) blocks with a length of m. m and n are independently selected integers, each of which may, for example, be selected in the range from about 5 or about 6 to about 100, from about 5 to about 60 or from about 6 to about 60 or from about 5 to 50. For example, linear PDMS-PEO such as $PDMS_{12}\text{-}PEO_{46}$ or $PDMS_{47}PEO_{36}$ are commercially available from Polymer Source Inc., Dorval (Montreal) Quebec, Canada. Accordingly, the PDMS-PEO block copolymer may comprise 5-100 blocks PDMS and 5-100 blocks PEO, 6-100 blocks PDMS and 6-100 blocks PEO, 5-100 blocks PDMS and 5-60 blocks PEO, or 5-60 blocks PDMS and 5-60 blocks PEO.

In accordance with the above, the present invention relates in one aspect to the method of eliciting an immune response in a subject, comprising administering to the subject a polymersome formed from PDMS-PEO carrying an antigen. The antigen can be associated/physically linked with the PDMS-PEO polymersome in any suitable way. For example, the PDMS-PEO polymersome may have a soluble antigen encapsulated therein as described in the present invention. Alternatively or in addition, the polymersome may have an antigen integrated/incorporated into the circumferential membrane of the polymersome as described in WO2014/077781A1. In this case, antigen is a membrane protein that is integrated with its (one or more) transmembrane domain into the circumferential membrane of the PDMS-PEO-polymersome. The integration can be achieved as described in WO2014/077781A1 or Nallani et al, "Proteopolymersomes: in vitro production of a membrane protein in polymersome membranes", Biointerphases, 1 Dec. 2011, page 153. In case, the antigen is encapsulated in the PDMS-PEO polymersome, it may be a soluble antigen selected from the group consisting of a polypeptide, a carbohydrate, a polynucleotide and combinations thereof. The present invention further relates to a method for production of such encapsulated antigens in a polymersome formed from PDMS-PEO as well as to polymersomes produced by said method.

The present invention further relates to compositions comprising PDMS-PEO polymersomes carrying an antigen. Also, in these compositions, the antigen can be associated/physically linked with the PDMS-PEO polymersome in any suitable way. For example, the PDMS-PEO polymersome may have a soluble antigen encapsulated therein as described in the present invention. Alternatively or in addition, the polymersome may have an antigen integrated/incorporated into the circumferential membrane of the polymersome as described in WO2014/077781A1. The present invention also relates to vaccines comprising such PDMS-PEO polymersomes carrying an antigen, methods of eliciting an immune response or methods for treatment, amelioration, prophylaxis or diagnostics of cancers, autoimmune or infectious diseases, such methods comprising providing PDMS-PEO polymersomes carrying an antigen to subject in need thereof.

In accordance with the above, the present invention also relates to the in vitro and in vivo use of a PDMS-PEO polymersomes carrying (or transporting) an antigen in a manner suitable for eliciting an immune response. The antigen can either be encapsulated in the PDMS-PEO polymersome or, for example, incorporated into the circumferential membrane of the polymersome as described in WO2014/077781A1.

In certain aspects, the polymersome of the present invention may contain one or more compartments (or otherwise termed "multicompartments"). Compartmentalization of the vesicular structure of polymersome allows for the co-existence of complex reaction pathways in living cell and helps to provide a spatial and temporal separation of many activities inside a cell. Accordingly, more than one type of antigens may be encapsulated by the polymersome of the present invention. The different antigens may have the same or different isoforms. Each compartment may also be formed of a same or a different amphiphilic polymer. In various aspects, two or more different antigens are integrated into the circumferential membrane of the amphiphilic polymer. Each compartment may encapsulate at least one of peptide, protein, and nucleic acid. The peptide, protein, polynucleotide or carbohydrate may be immunogenic.

Further details of suitable multicompartmentalized polymersomes can be found in WO 20121018306, the contents of which being hereby incorporated by reference in its entirety for all purposes.

The polymersomes may also be free-standing or immobilized on a surface, such as those described in WO 2010/1123462, the contents of which being hereby incorporated by reference in its entirety for all purposes.

In the case where the polymersome carrier contains more than one compartment, the compartments may comprise an outer block copolymer vesicle and at least one inner block copolymer vesicle, wherein the at least one inner block copolymer vesicle is encapsulated inside the outer block copolymer vesicle. In some aspects, each of the block copolymer of the outer vesicle and the inner vesicle includes a polyether block such as a poly(oxyethylene) block, a poly(oxypropylene) block, and a poly(oxybutylene) block. Further examples of blocks-that may be included in the copolymer include, but are not limited to, poly(acrylic acid), poly(methyl acrylate), polystyrene, poly(butadiene), poly(2-methyloxazoline), poly(dimethyl siloxane), poly(L-isocyanoalanine(2-thiophen-3-yl-ethyl)amide), poly(e-caprolactone), poly(propylene sulphide), poly(N-isopropylacrylamide), poly(2-vinylpyridine), poly(2-(diethylamino)ethyl methacrylate), poly(2-(diisopropylamino)ethylmethacrylate), poly(2-(methacryloyloxy)ethylphosphorylcholine) and poly(lactic acid). Examples of suitable outer vesicles and inner vesicles include, but are not limited to, poly(ethyl ethylene)-b-poly(ethylene oxide) (PEE-b-PEO), poly(butadiene)-b-poly(ethylene oxide) (PBD-b-PEO), poly(styrene)-b-poly(acrylic acid) (PS-b-PAA), poly(ethylene oxide)-poly(caprolactone) (PEO-b-PCL), poly(ethylene oxide)-poly(lactic acid) (PEO-b-PLA), poly(isoprene)-poly(ethylene oxide) (PI-b-PEO), poly(2-vinylpyridine)-poly(ethylene oxide) (P2VP-b-PEO), poly(ethylene oxide)-poly(N-isopropylacrylamide) (PEO-b-PNIPAm), poly(ethylene glycol)-poly(propylene sulfide) (PEG-b-PPS), poly (methylphenylsilane)-poly(ethylene oxide) (PMPS-b-PEO-b-PMPS-b-PEO-b-PMPS), poly(2-methyloxazoline)-b-poly-(dimethylsiloxane)-b-poly(2-methyloxazoline) (P MOXA-b-PDMS-b-P MOXA), poly(2-methyloxazoline)-b-poly(dimethylsiloxane)-b-poly(ethylene oxide) (PMOXA-b-PDMS-b-PEO), poly[styrene-b-poly(L-isocyanoalanine(2-thiophen-3-yl-ethyl)amide)] (PS-b-PIAT), poly(ethylene oxide)-b-poly(propylene sulfide)-b-poly(ethylene oxide) (PEO-b-PPS-b-PEO) and a poly(ethylene oxide)-poly(butylene oxide) (PEO-b-PBO) block copolymer. A block copolymer can be further specified by the average number of the respective blocks included in a copolymer. Thus $PS_M$-$PIAT_N$ indicates the presence of polystyrene blocks (PS) with M repeating units and poly(L-isocyanoalanine(2-thiophen-3-yl-ethyl)amide) (PIAT) blocks with N repeating units. Thus, M and N are independently selected integers, which may for example be selected in the range from about 5 to about 95. Thus, $PS_{40}$-$PIAT_{50}$ indicates the presence of PS blocks with an average of 40 repeating units and of PIAT blocks with an average of 50 repeating units.

In some aspects, the invention relates to a method for production of an encapsulated antigen in polymersome, said method comprising: i) dissolving an amphiphilic polymer of the present invention in chloroform, preferably said amphiphilic polymer is polybutadiene-polyethylene oxide (BD); ii) drying said dissolved amphiphilic polymer to form a polymer film; iii) adding a solubilized antigen to said dried amphiphilic polymer film from step ii), wherein said antigen is selected from the group consisting of: (a) a polypeptide; preferably said polypeptide is an antigen is according to the present invention; (b) a carbohydrate; (c) a combination of a) and/or b) and/or c); iv) rehydrating said polymer film from step iii) to form polymer vesicles; v) optionally, filtering polymer vesicles from step iv) to purify polymer vesicles monodisperse vesicles; and/or vi) optionally, isolating said polymer vesicles from step iv) or v) from the non-encapsulated antigen.

In some other aspects, the invention relates to other methods for production of an encapsulated antigen in polymersome including methods based on mixing a non-aqueous solution of polymers in aqueous solution of antigens, sonication of corresponding mixed solutions of polymers and antigens, or extrusion of corresponding mixed solutions of polymers and antigens. Exemplary methods include those described in Rameez et al, Langmuir 2009, and in Neil et al Langmuir 2009, 25(16), 9025-9029.

Compared to existing uptake and cross-presentation vehicles and methods based thereon the polymersomes of present invention inter alia offer the following advantages that are also aspects of the present invention:

The polymersomes are very efficient in uptake and cross-presentation to the immune system;

The immune response comprises a $CD8^{(+)}$ T cell-mediated immune response;

The polymersomes are oxidation-stable;

The humoral response is stronger compared to that produced by free antigen-based techniques with or without adjuvants;

The immune response induced by polymersomes of the present invention could still be even further boosted using adjuvants;

The polymers of polymersomes of the present invention are inherently robust and can be tailored or functionalized to increase their circulation time in the body;

The polymersomes of the present invention are stable in the presence of serum components;

The polymers of polymersomes are inexpensive and quick to synthesize;

The amount of an antigen required to elicit an immune response by the methods of the present invention using polymersomes of the present invention is less compared to free antigen-based techniques with or without adjuvants.

The invention is also characterized by the following items:

1. A polymersome (e.g., an oxidation-stable polymersome) comprising a soluble encapsulated antigen, wherein said soluble encapsulated antigen is selected from the group consisting of:
   i) a polypeptide;
   ii) a carbohydrate;
   iii) a polynucleotide, preferably said polynucleotide is not an antisense oligonucleotide, further preferably said polynucleotide is a DNA or mRNA molecule.
   iv) a combination of i) and/or ii) and/or iii).

2. The polymersome according to any one of preceding items, wherein said polymersome is capable of eliciting a $CD8^{(+)}$ T cell-mediated immune response, preferably said eliciting is an in vivo, ex vivo or in vitro eliciting.

3. The polymersome according to any one of preceding items, wherein said antigen comprises a soluble portion of a membrane protein (MP) or a membrane-associated peptide (MAP), preferably said antigen comprises a soluble portion of Influenza hemagglutinin, Swine Influenza hemagglutinin, Ovalbumin (OVA), Porcine epidemic diarrhea virus SPIKE protein, B16 peptide or MC38 peptide, further preferably said antigen comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14.

4. The polymersome according to any one of preceding items, wherein said polymersome is stable in the presence of serum components, preferably said stability is an in vivo, ex vivo or in vitro stability.

5. The polymersome according to any one of preceding items, wherein said polymersome is stable inside an endosome, preferably said stability is an in vivo, ex vivo or in vitro stability.
6. The polymersome according to any one of preceding items, wherein said polymersome has an improved oxidation stability compared to corresponding oxidation stability of a liposome, preferably said improved stability is an in vivo, ex vivo or in vitro improved stability.
7. The polymersome according to any one of preceding items, wherein said polymersome is capable of releasing its content comprising said soluble encapsulated antigen in an oxidation-independent manner and triggering $CD8^{(+)}$ T cell-mediated immune response, preferably said releasing is an in vivo, ex vivo or in vitro releasing.
8. The polymersome according to any one of preceding items, wherein said polymersome is capable of eliciting a cellular immune response, wherein said cellular immune response comprises a $CD8^{(+)}$ T cell-mediated immune response, preferably said immune response is an in vivo, ex vivo or in vitro immune response.
9. The polymersome according to any one of preceding items, wherein said polymersome is capable of eliciting a cellular and/or humoral immune response, wherein said cellular immune response comprises a $CD8^{(+)}$ T cell-mediated immune response, preferably immune response is an in vivo, ex vivo or in vitro immune response.
10. The polymersome according to any one of preceding items, wherein said humoral immune response comprises production of specific antibodies, further preferably said immune response is an in vivo, ex vivo or in vitro immune response.
11. The polymersome according to any one of preceding items, wherein said polymersome is capable of enhancing the frequency of effector $CD4^{(+)}$ T cells, preferably said enhancing is an in vivo, ex vivo or in vitro enhancing.
12. The polymersome according to any one of preceding items, wherein said cellular immune response comprises a T-cell mediated immune response, preferably said immune response is an in vivo, ex vivo or in vitro immune response.
13. The polymersome according to any one of preceding items, wherein said polymersome is capable of enhancing clonal expansion of antigen-specific $CD8^{(+)}$ T cells compared to a free antigen, preferably said expansion is an in vivo, ex vivo or in vitro expansion.
14. The polymersome according to any one of preceding items, wherein said polymersome is capable of inducing antigen-specific effector $CD8^{(+)}$ T cells, preferably said inducing is an in vivo, ex vivo or in vitro inducing.
15. The polymersome according to any one of preceding items, wherein said polymersome is capable of enhancing a cytotoxic phenotype of antigen-specific $CD8^{(+)}$ T cells, preferably said enhancing is an in vivo, ex vivo or in vitro enhancing.
16. The polymersome according to any one of preceding items, wherein said polymersome is capable of targeting of lymph node-resident macrophages and/or B cells, preferably said targeting is an in vivo, ex vivo or in vitro targeting.
17. The polymersome according to any one of preceding items, wherein said polymersome is reduction-stable, preferably said polymersome is reduction-stable in the presence of serum components, further preferably said reduction-stability is an in vivo, ex vivo or in vitro reduction-stability.
18. The polymersome according to any one of preceding items, wherein said polymersome has reduced permeability, preferably said reduced permeability is compared to a corresponding permeability of a liposome, further preferably said permeability is an in vivo, ex vivo or in vitro permeability.
19. The polymersome according to any one of preceding items, wherein said polymersome is capable of releasing its content inside an endosome, preferably said endosome is a late-endosome, further preferably said releasing is an in vivo, ex vivo or in vitro releasing.
20. The polymersome according to any one of preceding items, wherein said polymersome is capable of one or more of the following:
 i) eliciting a cellular immune response; preferably said cellular immune response comprises a $CD8^{(+)}$ T cell-mediated immune response; further preferably said cellular immune response is a $CD8^{(+)}$ T cell-mediated immune response; most preferably said cellular immune response is against a soluble portion of Influenza hemagglutinin, Swine Influenza hemagglutinin, Ovalbumin (OVA), Porcine epidemic diarrhea virus SPIKE protein, B16 peptide or MC38 peptide, further most preferably said cellular immune response is against a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 SEQ ID NOs: 12-14;
 ii) releasing polymersome content inside an endosome, preferably said endosome is a late endosome; further preferably said content comprises a soluble portion of Influenza hemagglutinin, Swine Influenza hemagglutinin, Ovalbumin (OVA), Porcine epidemic diarrhea virus SPIKE protein, B16 peptide or MC38 peptide, most preferably said content comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SED ID NOs: 12-14;
 iii) releasing polymersome content in an oxidation-independent manner and triggering $CD8^{(+)}$ T cell-mediated immune response; preferably said content comprises a soluble portion of Influenza hemagglutinin, Swine Influenza hemagglutinin, Ovalbumin (OVA), Porcine epidemic diarrhea virus SPIKE protein, B16 peptide or MC38 peptide, further preferably said content comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NOs: 12-14;

iv) stimulating an immune response to said antigen; preferably said antigen comprises a soluble portion of Influenza hemagglutinin, Swine Influenza hemagglutinin, Ovalbumin (OVA), Porcine epidemic diarrhea virus SPIKE protein, B16 peptide or MC38 peptide, further preferably said antigen comprises a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NOs:12-14;

v) triggering a cross-protection induced by a $CD8^{(+)}$ T cell-mediated immune response; preferably said response is against a soluble portion of Influenza hemagglutinin, Swine Influenza hemagglutinin, Porcine epidemic diarrhea virus SPIKE protein, Ovalbumin (OVA), B16 peptide or MC38 peptide, further preferably said response is against a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14;

vi) delivering a peptide or protein to an antigen-presenting cell (APC); preferably said peptide or protein comprises or is derived from a soluble portion of Influenza hemagglutinin, Swine Influenza hemagglutinin, Ovalbumin (OVA), Porcine epidemic diarrhea virus SPIKE protein, B16 peptide or MC38 peptide, further preferably said peptide or protein comprises or is derived from a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14;

vii) triggering an immune response comprising a $CD8^{(+)}$ T cell-mediated immune response and/or $CD4^{(+)}$ T cell-mediated immune response; preferably said response is against a soluble portion of Influenza hemagglutinin, Swine Influenza hemagglutinin, Ovalbumin (OVA), Porcine epidemic diarrhea virus SPIKE protein, B16 peptide or MC38 peptide, further preferably said response is against a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14;

viii) stimulating an immune response in a subject; preferably said response is against a soluble portion of Influenza hemagglutinin, Swine Influenza hemagglutinin, Ovalbumin (OVA), Porcine epidemic diarrhea virus SPIKE protein, B16 peptide or MC38 peptide, further preferably said response is against a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14;

ix) immunizing a non-human animal; preferably said immunizing is against a soluble portion of Influenza hemagglutinin, Swine Influenza hemagglutinin, Ovalbumin (OVA), Porcine epidemic diarrhea virus SPIKE protein, B16 peptide or MC38 peptide, further preferably said immunizing is against a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14;

x) said polymersome has an altered antigenicity compared to corresponding antigenicity of said antigen without said polymersome; preferably said antigen is a soluble portion of Influenza hemagglutinin, Swine Influenza hemagglutinin, Ovalbumin (OVA), Porcine epidemic diarrhea virus SPIKE protein, B16 peptide or MC38 peptide, further preferably said antigen is a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14;

xi) said polymersome has an altered immunogenicity compared to corresponding immunogenicity of said antigen without said polymersome, preferably said immunogen is a soluble portion of Influenza hemagglutinin, Swine Influenza hemagglutinin, Ovalbumin (OVA), Porcine epidemic diarrhea virus SPIKE protein, B16 peptide or MC38 peptide, further preferably said immunogen is a polypeptide which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14.

21. The polymersome according to any one of preceding items, wherein said polymersome has one or more of the following properties:
   i) said polymersome comprises an oxidation-stable membrane; and/or
   ii) said polymersome is synthetic; and/or
   iii) said polymersome is free from non-encapsulated antigens or in a mixture with free non-encapsulated antigens; and/or
   iv) said polymersome comprises a membrane of an amphiphilic polymer; and/or
   v) said polymersome comprises amphiphilic synthetic block copolymers forming a vesicle membrane; and/or
   vi) said polymersome has a diameter greater than 70 nm, wherein preferably the diameter is a range of about 100 nm to about 1 µm, or in the range from about 120 nm to about 250 nm, or from about 125 nm to about 250 nm, from about 140 nm to about 240 nm, from about 150 nm to about 235 nm, from about 170 nm to about 230 nm, or from about 220 nm to about 180 nm, or from about 190 nm to about 210 nm and/or
   vii) said polymersome has a vesicular morphology;
   viii) said polymersome is self-assembling.

22. The polymersome of item 21, wherein the polymersome is in the form of a collection of polymersomes, wherein the mean diameter of the collection of polymersomes is in the range of about 100 nm to about 1 µm, or in the range from about 100 nm to about 750 nm, or from about 100 nm to about 500 nm, or from about 120 nm to about 250 nm, from about 125 nm to about 250 nm, from about 140 nm to about 240 nm, from about 150 nm to about 235 nm, from about 170 nm to about 230 nm, or from about 220 nm to about 180 nm, or from about 190 nm to about 210 nm.

23. The polymersome according to any one of preceding items, wherein said antigen is an immunogen.

24. The polymersome according to any one of preceding items, wherein said antigen is selected from a group consisting of: i) a self-antigen, ii) a non-self antigen, iii) a non-self immunogen and iv) a self-immunogen.

25. The polymersome according to any one of preceding items, wherein said antigen is selected from the group consisting of:
   i) a polypeptide which is at least 80% or more (e.g., at least 85%, at least 90%, at least 95%, at least 96%, at least 97%, at least 98%, at least 99% or 100%) identical to a viral polypeptide sequence; preferably said viral polypeptide sequence is Influenza hemagglutinin or Swine Influenza hemagglutinin, further preferably said viral polypeptide sequence is selected from the group consisting of: SEQ ID NO: 5, SEQ ID NO: 6, SEQ ID NO: 7 and SEQ ID NO: 8;
   ii) a polypeptide which is at least 80% or more (e.g., at least 85%, at least 90%, at least 95%, at least 96%, at least 97%, at least 98%, at least 99% or 100%) identical to a bacterial polypeptide sequence;
   iii) a polypeptide which is at least 80% or more (e.g., at least 85%, at least 90%, at least 95%, at least 96%, at least 97%, at least 98%, at least 99% or 100%) identical to a mammalian or avian polypeptide sequence, preferably said mammalian or avian polypeptide sequence is Ovalbumin (OVA), a polypeptide which is at least 80% or more (e.g., at least 85%, at least 90%, at least 95%, at least 96%, at least 97%, at least 98%, at least 99% or 100%) identical of a SPIKE protein, B16 peptide or MC38 peptide, further preferably said mammalian or avian polypeptide sequence is selected from the group consisting of: SEQ ID NO: 4, SEQ ID NO: 1, SEQ ID NO: 2, SEQ ID NO: 3, SEQ ID NO: 9, SEQ ID NO: 10, SEQ ID NO: 11 and SEQ ID NOs:12-14.

26. The polymersome according to any one of preceding items, wherein said mammalian polypeptide sequence is selected from the group consisting of: human, rodent, rabbit and horse polypeptide sequence.

27. The polymersome according to any one of preceding items, wherein said antigen is an antibody or a fragment thereof.

28. The polymersome according to any one of preceding items, wherein said antigen is selected from the group consisting of:
   i) Influenza hemagglutinin (HA), preferably selected from the group consisting of: SEQ ID NO: 5, SEQ ID NO: 6, SEQ ID NO: 7 and SEQ ID NO: 8;
   ii) Swine Influenza hemagglutinin (HA), preferably SEQ ID NO: 6;
   iii) Ovalbumin (OVA), preferably SEQ ID NO: 4;
   iv) Porcine epidemic diarrhea virus (PED), Spike Protein, preferably SEQ ID NOs: 12-14;
   v) B16 peptide, preferably selected from the group consisting of: SEQ ID NO: 9, SEQ ID NO: 10 and SEQ ID NO: 11;
   vi) MC38 peptide, preferably selected from the group consisting of: SEQ ID NO: 1, SEQ ID NO: 2 and SEQ ID NO: 3;
   vii) B16 and MC38 peptides, preferably said peptides are independently selected the groups: i) SEQ ID NOs: 1-3 and ii) SEQ ID NOs: 9-11.

29. The polymersome according to any one of preceding items, wherein said polymersome is selected from the group consisting of: cationic, anionic and nonionic polymersome and mixtures thereof.

30. The polymersome according to any one of preceding items, wherein said block copolymer or amphiphilic polymer is essentially non-immunogenic or essentially non-antigenic, preferably said block copolymer or amphiphilic polymer is non-immunogenic or non-antigenic.

31. The polymersome according to any one of preceding items, wherein said block copolymer or amphiphilic polymer is oxidation-stable.

32. The polymersome according to any one of preceding items, wherein said block copolymer or said amphiphilic polymer is neither immunostimulant nor adjuvant.

33. The polymersome according to any one of preceding items, wherein said amphiphilic polymer comprises a diblock or a triblock (A-B-A or A-B-C) copolymer.

34. The polymersome according to any one of preceding items, wherein said amphiphilic polymer comprises a copolymer poly(N-vinylpyrrolidone)-b-PLA.

35. The polymersome according to any one of preceding items, wherein said amphiphilic polymer comprises at least one monomer unit of a carboxylic acid, an amide, an amine, an alkylene, a dialkylsiloxane, an ether or an alkylene sulphide.

36. The polymersome according to any one of preceding items, wherein the amphiphilic polymer is a polyether block selected from the group consisting of an oligo (oxyethylene) block, a poly(oxyethylene) block, an oligo(oxypropylene) block, a poly(oxypropylene) block, an oligo(oxybutylene) block and a poly(oxybutylene) block.
37. The polymersome according to any one of preceding items, wherein said amphiphilic polymer is a poly (butadiene)-poly(ethylene oxide) (PB-PEO) diblock copolymer.
38. The polymersome according to any one of preceding items, wherein said PB-PEO diblock copolymer comprises 5-50 blocks PB and 5-50 blocks PEO.
39. The polymersome according to any one of preceding items, wherein said amphiphilic polymer is a poly (dimethylsiloxane)-poly(ethylene oxide) (PDMS-PEO) diblock copolymer, wherein preferably said PB-PEO diblock copolymer preferably comprises 5-100 blocks PDMS and 5-100 blocks PEO.
40. The polymersome according to any one of preceding items, wherein said polymersomes may comprises of block copolymers or amphiphilic polymers only or mixed with lipids.
41. The polymersome according to anyone of preceding items, wherein said the lipids comprises of synthetic or natural lipids or lipid mixtures or combination of synthetic and natural lipids.
42. The polymersome according to any one of preceding items, wherein said amphiphilic polymer is a poly (lactide)-poly(ethylene oxide)/1-palmitoyl-2-oleoyl-sn-glycero-3-phospho-L-serine (PLA-PEO/POPC) copolymer, preferably said PLA-PEO/POPC has a ratio of 50:50 and above (e.g., 50/50 or 75/25 or 90/10) of PLA-PEO to POPC (e.g., PLA-PEO/POPC).
43. The polymersome according to any one of preceding items, wherein said amphiphilic polymer is a poly (caprolactone)-poly(ethylene oxide)/1-palmitoyl-2-oleoyl-sn-glycero-3-phospho-L-serine (PCL-PEO/POPC) copolymer, preferably said PCL-PEO/POPC has a ratio of 50:50 and above (e.g., 50/50 or 75/25 or 90/10) of PCL-PEO to POPC (e.g., PCL-PEO/POPC).
44. The polymersome according to any one of preceding items, wherein said amphiphilic polymer is polybutadiene-polyethylene oxide (BD) or a poly (dimethylsiloxane)-poly(ethylene oxide) (PDMS-PEO) diblock copolymer.
45. The polymersome according to any one of preceding items, wherein said polymersome comprises diblock copolymers $PBD_{21}$-$PEO_{14}$ (herein referred to as "BD21"), $PDMS_{47}$-$PEO_{36}$ (PDMS-PEO) or the triblock copolymer $PMOXA_{12}$-$PDMS_{55}$-$PMOXA_{12}$.
46. The polymersome according to any one of preceding items, wherein said polymersome comprises one or more compartments.
47. The polymersome according to any one of preceding items, wherein said polymersome comprises one or more compartments, wherein each one of said one or more compartments encapsulates at least one peptide, protein, and nucleic acid, preferably said at least one of said peptide, protein, and nucleic acid is immunogenic or antigenic, further preferably said each one of the one or more compartments is comprised of a same or different amphiphilic polymer.
48. The polymersome according to any one of preceding items, wherein said polymersome comprises more than one compartment, wherein said compartments comprise an outer block copolymer vesicle and at least one inner block copolymer vesicle, wherein said at least one inner block copolymer vesicle is encapsulated inside the outer block copolymer vesicle, preferably said outer block copolymer vesicle is a polymersome formed of a copolymer independently selected from the group consisting of:
i) poly[styrene-b-poly(L-isocyanoalanine(2-thiophen-3-yl-ethyl)amide)] (PS-PIAT),
ii) poly(butadiene)-poly(ethylene oxide) (PBD-PEO),
iii) poly(ethylene oxide)-poly(caprolactone) (PEO-PCL),
iv) poly(ethyl ethylene)-poly(ethylene oxide) (PEE-PEO),
v) poly(ethylene oxide)-poly(lactic acid) (PEO-PLA),
vi) poly(isoprene)-poly(ethylene oxide) (PI-PEO),
vii) poly(2-vinylpyridine)-poly(ethylene oxide) (P2VP-PEO),
viii) poly(ethylene oxide)-poly(N-isopropylacrylamide) (PEO-PNIPAm),
ix) poly(styrene)-poly(acrylic acid) (PS-PAA),
x) poly(ethylene glycol)-polypropylene sulfide) (PEG-PPS),
xi) poly(2-methyloxazoline)-poly(dimethylsiloxane)-poly(2-methyloxazoline) (PMOXA-PDMS-PMOXA),
xii) poly(ethylene oxide)-poly(dimethyl siloxane)-poly(2-methyloxazoline) (PEO-PDMS-PMOXA), and
xiii) poly(methylphenylsilane)-poly(ethylene oxide) (PMPS-PEO-PMPS-PEO-PMPS);
further preferably said at least one inner block copolymer vesicle is a polymersome formed of a copolymer independently selected from the group consisting of:
xiv) poly[styrene-b-poly(L-isocyanoalanine(2-thiophen-3-yl-ethyl)amide)] (PS-PIAT),
xv) poly(butadiene)-poly(ethylene oxide) (PBD-PEO),
xvi) poly(ethylene oxide)-poly(caprolactone) (PEO-PCL),
xvii) poly(ethyl ethylene)-poly(ethylene oxide) (PEE-PEO),
xviii) poly(ethylene oxide)-poly(lactic acid) (PEO-PLA),
xix) poly(isoprene)-poly(ethylene oxide) (PI-PEO),
xx) poly(2-vinylpyridine)-poly(ethylene oxide) (P2VP-PEO),
xxi) poly(ethylene oxide)-poly(N-isopropylacrylamide) (PEO-PNIPAm),
xxii) poly(styrene)-poly(acrylic acid) (PS-PAA),
xxiii) poly(ethylene glycol)-polypropylene sulfide) (PEG-PPS),
xxiv) poly(2-methyloxazoline)-poly(dimethylsiloxane)-poly(2-methyloxazoline) (PMOXA-PDMS-PMOXA),
xxv) poly(ethylene oxide)-poly(dimethyl siloxane)-poly(2-methyloxazoline) (PEO-PDMS-PMOXA), and
xxvi) poly(methylphenylsilane)-poly(ethylene oxide) (PMPS-PEO-PMPS-PEO-PMPS).
49. The polymersome according to any one of the preceding items, wherein said polymersome comprises a lipid polymer.
50. The polymersome according to any one of the preceding items, wherein the polymersome further comprises encapsulated adjuvant.
51. A method for production of encapsulated antigen in polymersome, said method comprising:

i) dissolving an amphiphilic polymer in chloroform, preferably said amphiphilic polymer is Polybutadiene-Polyethylene oxide (BD);
ii) drying said dissolved amphiphilic polymer to form a polymer film;
iii) adding a solubilized antigen to said dried amphiphilic polymer film from step ii), wherein said antigen is selected from the group consisting of:
a) a polypeptide; preferably said polypeptide antigen is according any one of preceding items, further preferably said polypeptide antigen comprises a soluble portion of Influenza hemagglutinin, Swine Influenza hemagglutinin, Ovalbumin (OVA), Porcine epidemic diarrhea virus SPIKE protein, B16 peptide or MC38 peptide, most preferably said polypeptide antigen is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14;
b) a carbohydrate;
c) a polynucleotide, wherein said polynucleotide is not an antisense oligonucleotide, preferably said polynucleotide is a DNA or mRNA molecule;
d) a combination of (a) and/or (b) and/or (c);
iv) rehydrating said polymer film from step iii) to form polymer vesicles;
v) optionally, filtering polymer vesicles from step iv) to purify polymer vesicles monodisperse vesicles; and/or
vi) optionally, isolating said polymer vesicles from step iv) or v) from the non-encapsulated antigen.

52. The method for production of encapsulated antigen in polymersome according to according to any one of preceding items, wherein said polymersome is the polymersome according to any one of preceding items.

53. A polymersome produced by a method for production of encapsulated antigen in polymersome according to any one of preceding items.

54. A composition comprising a polymersome according to any one of preceding items.

55. The composition according to any one of preceding items, wherein said composition is a pharmaceutical or diagnostic composition.

56. The composition according to any one of preceding items, wherein said composition is an immunogenic, antigenic or immunotherapeutic composition.

57. The composition according to any one of preceding items, further comprising one or more immunostimulants and/or one or more adjuvants.

58. The composition according to any one of preceding items, wherein said composition is a vaccine.

59. The composition according to any one of preceding items, formulated for intradermal, intraperitoneal, intramuscular, subcutaneous, intravenous injection, or non-invasive administration to a mucosal surface.

60. Isolated antigen presenting cells or a hybridoma cell exposed to the polymersome or composition according to any one of preceding items.

61. The antigen presenting cells according to any one of preceding items, wherein said antigen presenting cells comprise a dendritic cell.

62. The antigen presenting cells according to any one of preceding items, wherein said antigen presenting cells comprise macrophages.

63. The antigen presenting cells according to any one of preceding items, wherein said antigen presenting cells comprise B-cells.

64. A vaccine comprising the polymersome, composition, antigen presenting cells or hybridoma according to any one of preceding items, and further comprising a pharmaceutically accepted excipient or carrier.

65. The vaccine according to any one of preceding items, wherein:

i) said antigen comprises Influenza hemagglutinin (HA), wherein said vaccine is an Influenza vaccine, preferably said Influenza hemagglutinin (HA) is at least 60% or more (e.g., at least 65%, at least 70%, at least 75%, at least 80%, at least 85%, at least 90%, at least 95%, at least 96%, at least 97%, at least 98%, at least 99% or 100%) identical to polypeptide selected from the group consisting of: SEQ ID NO: 5, SEQ ID NO: 6, SEQ ID NO: 7 and SEQ ID NO: 8;

ii) said antigen comprises Swine Influenza hemagglutinin (HA), wherein said vaccine is Swine Influenza vaccine, preferably said Swine Influenza hemagglutinin (HA) is at least 60% or more (e.g., at least 65%, at least 70%, at least 75%, at least 80%, at least 85%, at least 90%, at least 95%, at least 96%, at least 97%, at least 98%, at least 99% or 100%) identical to SEQ ID NO: 6;

iii) said antigen comprises Ovalbumin (OVA), wherein said vaccine is a cancer vaccine, preferably said Ovalbumin (OVA) is at least 60% or more (e.g., at least 65%, at least 70%, at least 75%, at least 80%, at least 85%, at least 90%, at least 95%, at least 96%, at least 97%, at least 98%, at least 99% or 100%) identical to SEQ ID NO: 4;

iv) said antigen comprises SPIKE protein (PEDv S), wherein said vaccine is as PED Vaccine, preferably said Porcine epidemic diarrhea virus SPIKE protein (S protein) which is at least 80% or more (e.g., at least 85%, at least 90%, at least 95%, at least 96%, at least 97%, at least 98%, at least 99% or 100%) identical of SEQ ID NOs: 12-14, v) said antigen comprises B16 peptide, wherein said vaccine is a cancer vaccine, preferably said peptide is selected from the group consisting of: SEQ ID NO: 9-11;

vi) said antigen comprises MC38 peptide, wherein said vaccine is a cancer vaccine preferably said peptide is selected from the group consisting of: SEQ ID NO: 1-3;

vii) said antigen comprises B16 and MC38 peptides, wherein said vaccine is a cancer vaccine, preferably said peptides are independently selected the groups: i) SEQ ID NOs: 1-3 and ii) SEQ ID NOs: 9-11;

viii) said antigen is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 9, SEQ ID NO: 10, SEQ ID NO: 11; wherein said vaccine is a cancer vaccine.

66. A kit comprising the polymersome, composition, antigen presenting cells, hybridoma or vaccine according to any one of preceding items.

67. A method of eliciting an immune response in a subject (e.g. human), comprising:
   i) providing the polymersome, composition, antigen presenting cells, hybridoma or vaccine according to any one of preceding items to said subject,
   ii) administering said polymersome, composition, antigen presenting cells, hybridoma or vaccine to said subject, preferably said administering is intradermal, intraperitoneal, intramuscular, subcutaneous, intravenous injection, or non-invasive administration to a mucosal surface.
68. The method of eliciting an immune response according to any one of preceding items, wherein said immune response is a broad immune response.
69. The method of eliciting an immune response according to any one of preceding items, wherein said immune response comprises a $CD8^{(+)}$ T cell-mediated immune response and/or $CD4^{(+)}$ T cell-mediated immune response.
70. A method for the treatment or prevention of an infectious disease, a cancer or autoimmune disease in a subject in need thereof (e.g. human) comprising administering to said subject a therapeutically effective amount of the polymersome, composition, antigen presenting cells, hybridoma or vaccine according to any one of preceding items, preferably said infectious disease is a viral or bacterial infectious disease.
71. A method for immunizing a non-human animal, said method comprising the following steps:
   i) providing the polymersome, composition, antigen presenting cells, hybridoma or vaccine according to any one of preceding items;
   ii) immunizing said non-human animal with said polymersome, composition, antigen presenting cells, hybridoma or vaccine.
72. A method for preparation of an antibody, comprising:
   i) immunizing a non-human mammal with the polymersome, composition, antigen presenting cells, hybridoma or vaccine according to any one of preceding items;
   ii) isolating an antibody obtained in step (i).
73. The method according to any one of preceding items, wherein said antibody is a monoclonal antibody (mAb).
74. The polymersome, composition, antigen presenting cells, hybridoma or vaccine according to any one of preceding items, for use as a medicament.
75. The polymersome, composition, antigen presenting cells, hybridoma or vaccine according to any one of preceding items for use in one or more of the following methods:
   i) in a method of antibody discovery and/or screening and/or preparation;
   ii) in a method of vaccine discovery and/or screening and/or preparation;
   iii) in a method of production or preparation of an immunogenic or immunostimulant composition;
   iv) in a method of targeted delivery of a protein and/or peptide, preferably said targeted delivery is a targeted delivery of an antigenic protein and/or peptide according to any one of preceding items; further preferably said antigenic protein and/or peptide comprises a soluble portion of a membrane protein (MP) or a membrane-associated peptide (MAP), most preferably said antigen comprises a soluble portion of Influenza hemagglutinin, Swine Influenza hemagglutinin, Ovalbumin (OVA), Porcine epidemic diarrhea virus SPIKE protein, B16 peptide or MC38 peptide, further most preferably said antigen is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14; further most preferably said targeted delivery is carried out in a subject;
   v) in a method of stimulating an immune response to an antigen, preferably said antigen is according to any one of preceding items, further preferably said antigen comprises a soluble portion of Influenza hemagglutinin, Swine Influenza hemagglutinin, Ovalbumin (OVA), Porcine epidemic diarrhea virus SPIKE protein, B16 peptide or MC38 peptide; further most preferably said antigen is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14; further most preferably for use in stimulating an immune response to said antigen in a subject;
   vi) in a method of triggering cross-protection induced by $CD8^{(+)}$ T cell-mediated immune response, preferably in a method of triggering cross-protection induced by $CD8^{(+)}$ T cell-mediated immune response against an antigen is according to any one of preceding items according to any one of preceding items; further preferably said antigen comprises a soluble portion of Influenza hemagglutinin, Swine Influenza hemagglutinin, Ovalbumin (OVA), Porcine epidemic diarrhea virus SPIKE protein, B16 peptide or MC38 peptide; most preferably said antigen is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14;
   vii) in a method of delivering a peptide and/or protein to an antigen-presenting cells (APCs) according to any one of preceding items; preferably said peptide and/or protein is an antigen according to any one of preceding items; further preferably said antigen comprises a soluble portion of Influenza hemagglutinin, Swine Influenza hemagglutinin, Ovalbumin (OVA), Porcine epidemic diarrhea virus SPIKE protein, B16 peptide or MC38 peptide; most preferably said antigen is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14;
viii) in a method of triggering an immune response comprising a CD8$^{(+)}$ T cell-mediated immune response and/or CD4$^{(+)}$ T cell-mediated immune response; preferably said response is against an antigen according to any one of preceding items; further preferably said antigen comprises a soluble portion of Influenza hemagglutinin, Swine Influenza hemagglutinin, Ovalbumin (OVA), Porcine epidemic diarrhea virus SPIKE protein, B16 peptide or MC38 peptide; further preferably said response is against an antigen which is at least 60% or more (e.g., at least 65%, at least 70%, at least 75%, at least 80%, at least 85%, at least 90%, at least 95%, at least 96%, at least 97%, at least 98%, at least 99% or 100%) identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, and SEQ ID NOs:12-14;
ix) in a method for treatment, amelioration, prophylaxis or diagnostics of an infectious disease, preferably said infectious disease is a viral or bacterial infectious disease; further preferably said viral infectious disease is selected from a group consisting of: influenza infection, respiratory syncytial virus infection, herpes virus infection.
x) in a method for treatment, amelioration, prophylaxis or diagnostics of a cancer or an autoimmune disease;
xi) in a method for sensitizing cancer cells to chemotherapy;
xii) in a method for induction of apoptosis in cancer cells;
xiii) in a method for stimulating an immune response in a subject;
xiv) in a method for immunizing a non-human animal;
xv) in a method for preparation of hybridoma;
xvi) in a method according to any one of preceding items;
xvii) in a method according to any one of preceding i)-xvi), wherein said method is in vivo and/or ex vivo and/or in vitro method;
xviii) in a method according to any one of preceding i)-xvii), wherein said antigen is heterologous to the environment in which said antigen is used.

76. Use of the polymersome, composition, antigen presenting cells, hybridoma or vaccine according to any one of preceding items for one or more of the following:
i) for antibody discovery and/or screening and/or preparation;
ii) for vaccine discovery and/or screening and/or preparation;
iii) for production or preparation of an immunogenic or immunostimulant composition;
iv) for targeted delivery of proteins and/or peptides, preferably said targeted delivery is a targeted delivery of antigenic proteins and/or peptides; further preferably said targeted delivery is carried out in a subject;
v) for stimulating an immune response to an antigen, preferably for use in stimulating an immune response to an antigen in a subject;
vi) for triggering cross-protection induced by a CD8$^{(+)}$ T cell-mediated immune response;
vii) for delivering a peptide or protein to an antigen-presenting cell (APC); preferably said peptide or protein is an antigen, further preferably said peptide or protein is immunogenic or immunotherapeutic;
viii) for triggering an immune response comprising a CD8$^{(+)}$ T cell-mediated immune response and/or CD4$^{(+)}$ T cell-mediated immune response;
ix) in a method for treatment, amelioration, prophylaxis or diagnostics of an infectious disease, preferably said infectious disease is a viral or bacterial infectious disease; further preferably said viral infectious disease is selected from a group consisting of: influenza infection, respiratory syncytial virus infection; herpes virus infection;
x) for treatment, amelioration, prophylaxis or diagnostics of a cancer or an autoimmune disease;
xi) for sensitizing cancer cells to chemotherapy;
xii) for induction of apoptosis in cancer cells;
xiii) for stimulating an immune response in a subject;
xiv) for immunizing a non-human animal;
xv) for preparation of hybridoma;
xvi) in a method according to any one of preceding items;
xvii) for use according to any one of preceding i)-xvi), wherein said use is in vivo and/or ex vivo and/or in vitro use;
xviii) for use according to any one of preceding i)-xvii), wherein said antigen is heterologous to the environment in which said antigen is used.

77. A method of eliciting an immune response in a subject, comprising administering to a subject a polymersome formed from PDMS-PEO carrying an antigen.

78. The method of item 77, wherein the antigen is encapsulated within the PDMS-PEO polymersome.

79. The method of item 78, wherein the antigen encapsulated in the PDMS-PEO polymersome is a soluble antigen.

80. The method of item 79, wherein the antigen is selected from the group consisting of a polypeptide, a carbohydrate, a polynucleotide and combinations thereof.

81. The method of item 77, wherein the antigen is integrated into the circumferential membrane of the PDMS-PEO polymersome.

82. A PDMS-PEO polymersomes carrying an antigen.

83. A polymersome of item 82, wherein the antigen is encapsulated within the PDMS-PEO polymersome.

84. The polymersome of item 83, wherein the antigen encapsulated in the PDMS-PEO polymersome is a soluble antigen.

85. The polymersome of item 84, wherein the antigen is selected from the group consisting of a polypeptide, a carbohydrate, a polynucleotide and combinations thereof.

86. The polymersome of item 85, wherein the antigen is integrated into the circumferential membrane of the PDMS-PEO polymersome 87. The polymersome of item 86, wherein the antigen is a membrane-associated protein or lipid antigen.

88. The polymersome of item 87, wherein the membrane-associated protein is selected from the group consisting of a transmembrane protein, G protein-coupled receptor, neurotransmitter receptor, kinase, porin, ABC transporter, ion transporter, acetylcholine receptor, and a cell adhesion receptor.

89. A pharmaceutical composition comprising a polymersome of any of items 82 to 88.

90. The in vitro and in vivo use of a PDMS-PEO as defined in any of items 82 to 88 or a pharmaceutical composition of item 89 for eliciting an immune response.

EXAMPLES OF THE INVENTION

In order that the invention may be readily understood and put into practical effect, some aspects of the invention are described by way of the following non-limiting examples.

Materials and Methods

Example 1: Encapsulation of Ovalbumin, Peptides, Soluble HA, PEDv SPIKE Protein and eGFP DNA in Polymersomes A 100 mg/ml stock of Polybutadiene-Polyethylene oxide (herein referred to as "BD21") is dissolved in chloroform. 100 µL of the 100 mg/ml BD21 stock is then deposited into a borosilicate (12×75 mm) culture tube and slowly dried under a stream of nitrogen gas to form a thin polymer film. The film was further dried under vacuum for 6 hours in a desiccator. A 1 mL solution of 1-5 mg/ml solubilized Ovalbumin (OVA) protein in 1×PBS buffer was then added to the culture tube. The mixture was stirred at 600 rpm, 4° C. for at least 18 hours to rehydrate the film and to allow the formation of polymer vesicles. The turbid suspension was extruded through a 200-nm pore size Whatman Nucleopore membrane with an extruder (Avanti 1 mL liposome extruder, 21 strokes) to obtain monodisperse vesicles [e.g., Fu et al., 2011, Lim. S. K, et al., 2017]. The protein containing BD21 polymer vesicles were purified from the non-encapsulated proteins by dialyzing the mixture against 1 L of 1×PBS using a dialysis membrane (300 kDa MWCO, cellulose ester membrane).

The final vesicle mixture was analysed for non-encapsulated protein using size-exclusion chromatography. Fractions of the vesicle peak from SEC were used to quantify the amount of protein encapsulation via SDS-PAGE. Vesicle size and mono-dispersity was characterized by dynamic light scattering instrument (Malvern, United Kingdom) (100× dilution with 1×PBS). For quantification of OVA encapsulated in polymersomes, samples were pre-treated with 20% DMSO followed by sample buffer, after which they were loaded on to the SDS-PAGE analysis.

For peptides encapsulation (exemplified by MC 38 neoantigen peptides of SEQ ID NO: 1, 2 and 3), a similar protocol was followed. Peptides concentration was 0.5-0.3 mg/ml dissolved in PBS for encapsulation. After dialysis, an amount of encapsulated peptides was determined using Phenylalanine fluorescence (ex 270 nm/em 310 nm) using a Cary Eclipse Spectrophotometer (Agilent). Encapsulation of all 3 peptides was performed individually and concentration was determined to be 20-30 µg/ml for all peptides. An equivalent volume of each of 3 encapsulated peptides was mixed together just before injection into mice.

For HA encapsulation, a similar protocol was followed. Recombinant HA (H1N1/A/Puerto Rico/8/1934 strain) at a concentration of 10 ug/ml was dissolved in PBS for encapsulation. After dialysis, an amount of encapsulated peptides was determined by western blot. HA concentration after encapsulation was determined to be around 1 ug/ml. 100 ul were injected in mice.

For PEDv SPIKE protein encapsulation in BD21 polymersomes, a similar protocol was followed as described above. PEDv SPIKE protein (different constructs, SEQ ID Nos: 12-14) were expressed using Baculovirus expression system. Proteins isolated from the insect cells were added for encapsulation. Whereas, for encapsulation of PEDv SPIKE protein in polymersomes made of poly(dimethyl siloxane)-poly(ethylene oxide) ($PDMS_{46}$-$PEO_{37}$ obtained from Polymer Source, Quebec, Canada), or a mixture of block copolymers and lipids such as $PDMS_{46}$-$PEO_{37}$ (/DSPE-PEG, PLA-PEG/POPC, PLA-PEG/Asolectin, a different protocol was followed in order to show the generality of the methods. Polymer and or polymer lipid mixture were dissolved in ethanol or any water miscible solvent and added dropwise to a protein solution to self-assemble and the proteins are encapsulated into polymersomes during self-assembly. Non-encapsulated proteins were removed by dialysis with PBS. After dialysis, amount of each polymersome sample encapsulated proteins was determined by densitometry. The concentration of proteins after encapsulation was determined to be around 1 µg/ml for each of these polymersome formulations. Polymersomes were encapsulated either with soluble SPIKE protein (SEQ 12) or S1 region of SPIKE protein (SEQ 13) and S2 region of SPIKE protein (SEQ 14). 100-200 µl of polymersomes (either only with soluble SPIKE protein or with mixture of polymersomes with S1 and S2 region of SPIKE proteins) were injected in mice and 1 ml of such polymersomes was orally administered to pigs.

For eGFR DNA encapsulation, a similar protocol as OVA encapsulation was followed. Briefly, block co-polymers such as poly(butadiene)-poly(ethyleneoxide) (BD21), poly (butadiene)-poly(ethyleneoxide) modified with functional groups (e.g., $NH_2$, COOH) at the end of poly(ethylene oxide) chain (BD21-$NH_2$), mixture of block copolymers and lipids such as PLA-PEG/POPC, PLA-PEG/Asolectin, Dimethylaminoethane-carbamoyl (DC)-Cholesterol, 1,2-dioleoyl-3-trimethylammonium-propane (DOTAP) were dissolved in chloroform and transferred to a glass tube and slowly dried under a stream of nitrogen gas to form a thin film. The film was further dried under vacuum for 6 hours in a desiccator. 1 µg of eGFP DNA was added to the film and rehydrated overnight. Afterwards, the samples were extruded with 0.2 um polycarbonate filter and dialyzed in HEPES Buffer.

Example 2: Transfection of eGFP DNA Encapsulated Polymersomes with HEK293T Cells HEK293T cells were seeded with a density of 50,000 cells/well into a 48-well plate. For transfections (the Lipofectamine 2000 transfection), 1,000 µL of Opti-MEM I (Invitrogen), 2 µL of Lipofectamine 2000 (Invitrogen), and 1 µg of SF-GFP PC DNA (or polymersomes formulation containing 1 µg of SF-GFP PC DNA) were mixed. The transfection complexes were formed during 20 min incubation at RT. For transfection, the lipofectamine complex was added to the cells and incubated for 24 hr to 72 hr at 37C and 5% CO2. The efficiency of transfection was measured by GFP fluorescence, Ex 485 nm, Em 520 nm). For cellular uptake fluorescence measured at Ex 530 nm Em 560 nm. For imaging, aspirated the cell media followed by washed the cells with DPBS (with Ca2+/Mg2+) and fixed with 4% p-formaldehyde. Then, the glass cover-slip was removed and flipped into a glass slide containing a drop of 20 ul mounting media with DAPI. Finally, sealed the cover-slip with nail polish and stored at 4 C for future imaging. Fluorescence microscopy was used for imaging.

Example 3: Immunization of OVA Encapsulated Polymersomes for Antibody Titers

C57bl/6 mice were immunized using free OVA with or without Sigma Adjuvant System (SAS) and OVA encapsulated ACMs (polymersomes) by doing a prime and a boost 21 days later. All immunizations were performed with a final amount of OVA: 5-10 ug OVA/injection/mouse. Final bleeds were collected 42 days after prime. ELISA was then performed to assess titers: OVA was coated onto MaxiSorp plates (1 ug/ml) overnight. Plates were blocked using 3% BSA in PBS for 1 h at RT. All sera were diluted at 1:100 and incubated on plates for 1 h at RT. After 3 washes with PBS+0.05% Tween 20, secondary antibody anti-mouse IgG HRP coupled was incubated at 1:10,000 dilution for 1 h, RT (room temperature). After 3 washes with PBS/Tween 20 buffer, TMB substrate was added and reaction was stopped using 1M HCl. Optical densities were quantified at 450 nm.

Example 4: Immunization of HA encapsulated polymersomes for antibody titers

Similarly, Balb/c mice were immunized with free HA proteins (SEQ ID NO: 7), ACM encapsulated HA (polymersomes) in PBS or PBS control. All immunizations were performed with a same final amount of HA: 100 ng HN injection/mouse. Final bleeds were collected 42 days after prime and ELISA were performed as above using 1 ug/ml HA for plate coating.

Example 5: Immunization of MC 38 Neo-Antigen Peptides Encapsulated Polymersomes for Cellular Response To observe a specific CD8 T cell response after immunization we used a MC-38 syngeneic tumour model. C57bl/6 mice were inoculated with subcutaneously at the right flank with MC-38 tumour cells ($3 \times 10^5$) in 0.1 ml of PBS for tumour development. The inoculation day is defined as Day 0. The animals were randomized based on the bodyweights and immunizations were started at day 4 after the inoculation. Immunizations consisted of: free peptides, ACM encapsulated peptides (polymersomes) with and without co-treatment with a commercially available anti-PD-1 antibody. Peptides were: Reps1 P45A (SEQ ID NO: 1), Adpgk R304M (SEQ ID NO: 2) and Dpagt1 V213L (SEQ ID NO: 3) and were obtained from Genscript. 200 ul of peptides and peptides in ACMs were immunized subcutaneously on day 4, 11 and 18. The concentration of peptides in ACMs was determined to be 20-30 µg/ml, whereas for peptides alone 10 µg per injection per mice was used. The anti-PD1 antibody was injected intraperitoneally on day 5, 8, 12, 15, 19 and 22 at 5 mg/kg dosage. Animals were checked for any effects of tumour growth and treatments on normal behaviour such as mobility, food and water consumption, body weight gain/loss (body weights will be measured 3 times per week). Tumour sizes were measured 3 times per week in two dimensions using a caliper, and the volume was expressed in $mm^3$ using the formula: $V=0.5 \, a \times b^2$ where a and b are the long and short diameters of the tumour, respectively.

Example 6: Immunization of Mice and Pigs with PEDv Spike Protein Encapsulated Polymersomes Mice were immunised with ACM encapsulated PEDv spike protein and boosted with a second dose after 21 days, 150 ul-200 µl of polymersomes encapsulated with PEDv Spike protein were immunized. Sera was collected from the final bleed and was used for ELISA. Moreover, these sera were tested for their ability to neutralise the PEDV strain USA/Colorado/2013 (CO/13) through a conventional virus neutralisation. Furthermore, weaned pigs were orally vaccinated with 1 ml of polymersome encapsulated with PED SPIKE protein (after a prime on day 1 and a boost on day 14). A simple physiological solution was used for the oral vaccination.

Results

Encapsulation of Proteins and DNA of Example 1:

OVA encapsulated polymersomes were purified by dialysis and size exclusion column (SEC) to remove the non-encapsulated proteins and analysed by dynamic light scattering. As shown in FIG. 2A, FIGS. 3 and 4, an elution profile of OVA encapsulated polymersomes from SEC and a monodisperse population was observed.

Dynamic light scattering (DLS) data is presented in FIG. 2B for various of different polymersomes having encapsulated therein OVA, PEDv SPIKE protein or eGFP DNA. They are all measuring a mean diameter of 120 nm-180 nm using Z-average (d, nm), a preferred DLS parameter. Z-average size is the intensity weighted harmonic mean particle diameter, the values are in good agreement with earlier data [Fu et al., 2011, Lim. S. K, et al., 2017] of polymersomes.

Encapsulated eGFP DNA and Transfection Data of Example 2:

eGFP DNA encapsulated polymersomes were transfected with HEK293T cells and after transfection, the uptake of ACM polymersomes were measured by fluorescence plate reader at Ex 530 nm and Em 560 nm and the transfection efficiency was measured by the GFP fluorescence (Ex 485 nm, Em 520 nm). As shown in FIG. 5, it is clear that polymersomes with DNA are able to penetrate into the cells and releasing the DNA to express the DNA to protein, all the polymersome formulations are taken up the cells and are able to release the DNA, whereas the ratio of the polymersomes release versus the protein expression correlates well with its stability and biodegradability (FIG. 5A). Non-biodegradable polymersomes such as BD21 are taken up in smaller amount and the expression levels were lower comparing to the biodegradable polymersomes. Similar results were observed from the fluorescence images of cells as well (FIG. 5B & FIG. 5C).

Encapsulated OVA and Titers of Example 3:

OVA encapsulated polymersomes were immunized in C57bl/6 mice by doing a prime and a boost 21 days later. Final bleeds were used for performing the ELISA. As shown in FIG. 6, it is clear that OVA encapsulated polymersomes is the only formulation able to trigger a titer in comparison to free OVA, OVA with adjuvants or control samples (PBS alone). The reason why OVA with SAS did not produce a titer may be due to the small amount of OVA used in the trial (around 5 ug per injection). Hence ACM encapsulated OVA was able to trigger a B cell response toward OVA in the form of an IgG serum titer specific for Ovalbumin.

Encapsulated HA and Titers of Example 4:

HA (H1N1/A/Puerto Rico/8/1934 strain, SEQ ID NO: 7) encapsulated polymersomes were immunized in Balb/c mice by doing a prime and a boost 21 days later. Final bleeds were used for performing the ELISA. As shown in FIG. 7, it is clear that HA encapsulated polymersomes is the only formulation able to trigger a titer in comparison to free HA or control samples (PBS alone). The reason why free HA did not produce a titer may be due to the small amount of HA used in the trial (around 100 ng per injection). Hence ACM encapsulated HA was able to trigger a B cell response toward HA in the form of an IgG serum titer specific for HA.

Figure 8:
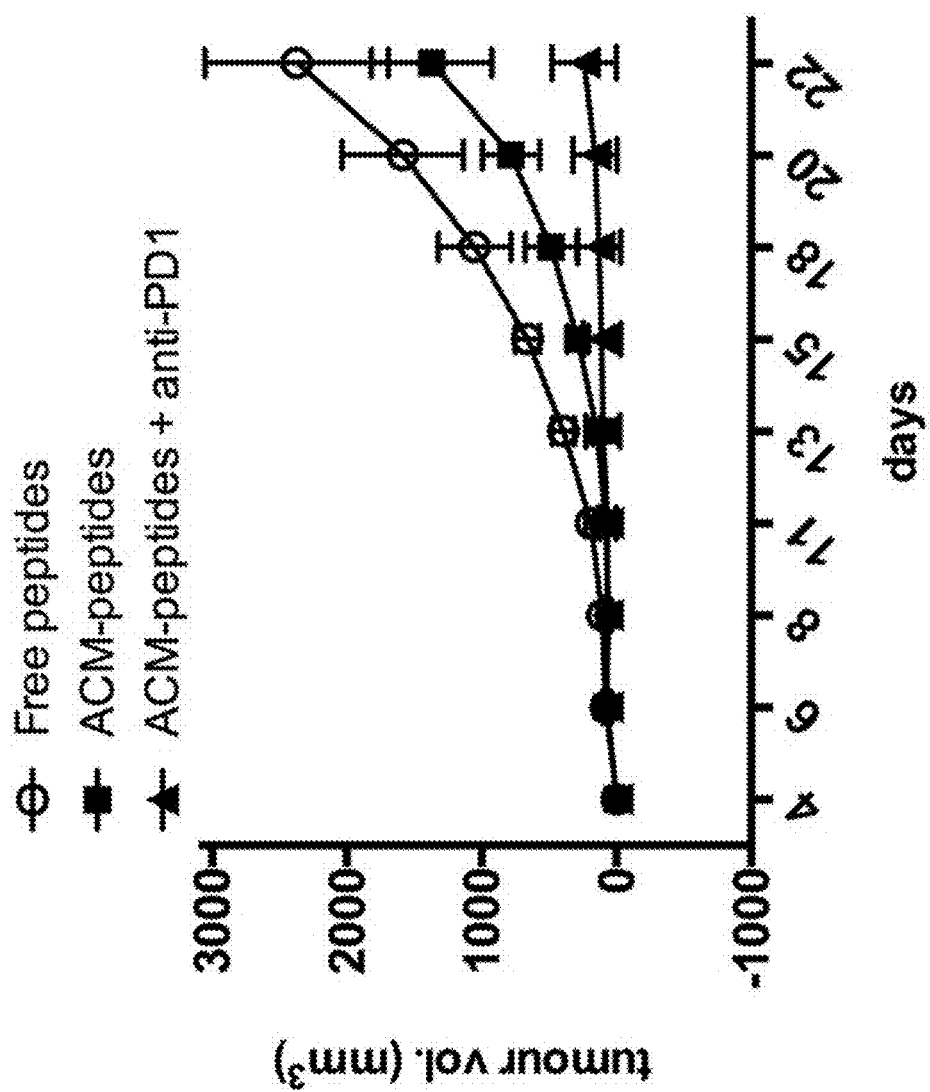
FIG. 8 shows results for a MC-38 mouse tumor model. Tumor volume was monitored in mice immunized with free peptides (open circle), ACM encapsulated peptides (closed square, polymersomes of the present invention) or with ACM encapsulated peptides together with an anti-PD1 antibody treatment (closed triangle). Tumor development was altered by ACM encapsulated peptides (polymersomes of the present invention) over free peptides, which is further potentiated by addition of the anti-PD1 antibody. No adjuvant was added in any of the groups.

Encapsulated MC-38 neo antigen peptides and CD8 T cell response of Example 5:

In order to show that ACM encapsulated antigen are able to trigger a CD8 T cell response we used a well-defined MC-38 syngeneic mouse tumour model which relies on the delivery of known CD8 antigenic peptides. High quantities of these peptides combined with adjuvants have been shown to trigger tumour control in therapeutic mouse models (e.g., Kuai et al., 2017, Luo et al., 2017). In addition, these effects were clearly correlated to the presence of peptide-specific CD8 T cells in the mouse blood. Hence any tumour development difference between groups would be directly attributed to the presence of a peptide-specific pool of CD8 T cells. 4 days after inoculation with MC-38 cell lines, mice were immunized with either free peptides, ACM encapsulated peptides (polymersomes) with and without anti-PD1 antibody treatment as described in the section Materials and Methods herein. As shown in FIG. 8, immunization with encapsulated peptides was able to trigger an inhibitory effect in tumour development compared to free peptides. This effect was dramatically potentiated whenever anti-PD1 antibody injections were added. This data demonstrated that ACM encapsulated peptides (polymersomes) were able to trigger a peptide-specific CD8 T cell response most likely via the delivery of these peptides to dendritic cells, which resulted in tumour control. This effect was increased by addition of a checkpoint inhibitor such the anti-PD1 antibody. Indeed, MC-38 has been shown to express PD-L1 molecule at their cell surface which is known to inhibit T cells killing activity inside tumours. Hence inhibition of such interaction by an antibody blocking PD1/PD-L1 interaction is known to reveal the presence of tumour specific T cells even further. Altogether this data clearly demonstrates that ACM encapsulated antigens (polymersomes) were able to trigger an antigen specific CD8 T cell response without addition of adjuvant.

Figure 9:
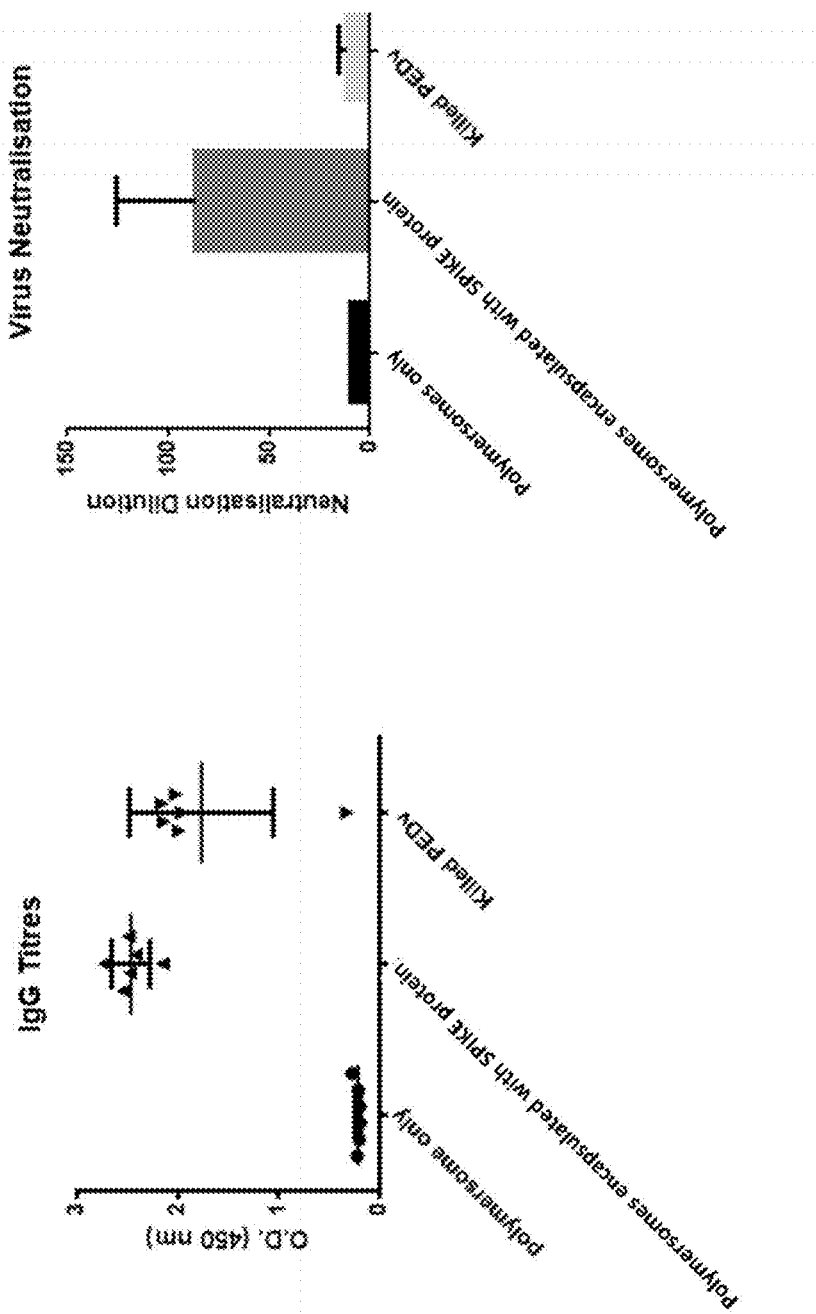
FIG. 9 shows IgG Antibody titres and virus neutralisation (against the strain PEDv USA/Colorado/2013 (CO/13)) from mice sera that were immunised with PBS and with a soluble fragment of the PEDv S Protein that has been encapsulated in a polymersome used as herein ("Polymersomes encapsulated with SPIKE protein") and in comparison, with killed PED virus ("Killed PEDv") and ACM polymersomes only (i.e., without any antigen, "polymersomes only"). From the IgG Titre of FIG. 9, it is evident that both the ACM encapsulated fragment of the PEDv S Protein and the killed virus induce IgG titres. The virus neutralisation data shows that only the ACM encapsulated PEDv S protein results in a significant neutralising titre while the with a negative control (ACM Polymersomes without any antigen) and killed PED virus show negligible neutralisation.
Figure 10:
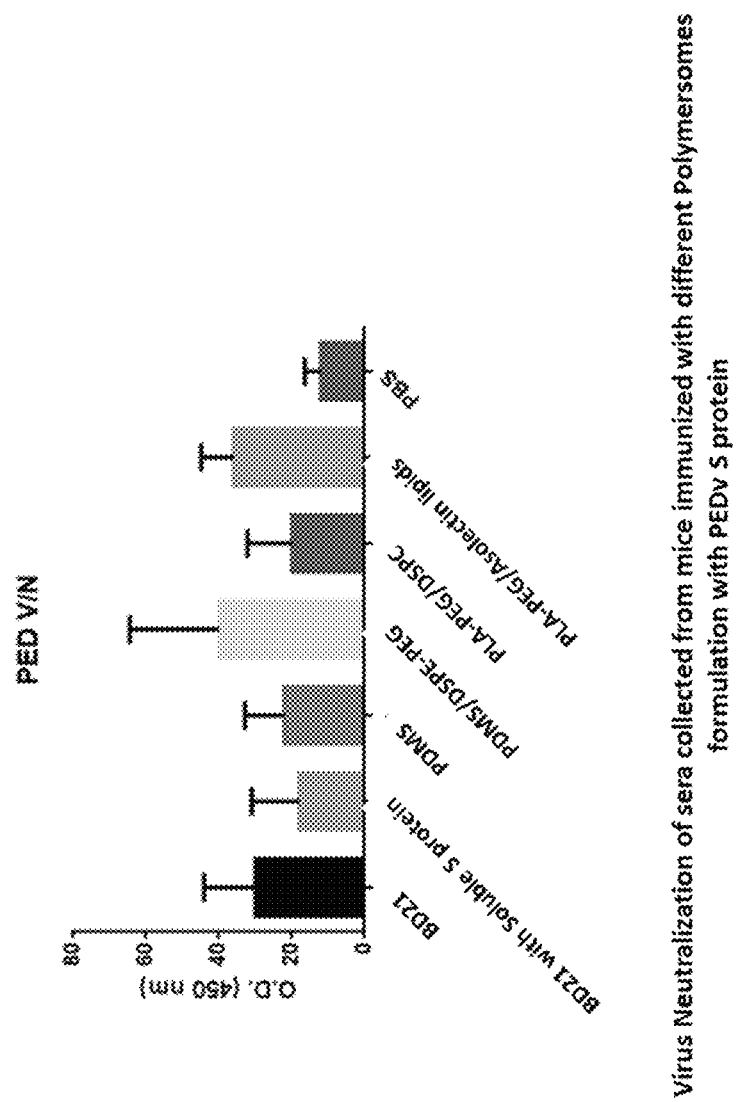
FIG. 10 shows virus neutralization data (against the strain PEDv USA/Colorado/2013 (CO/13)) from sera generated from mice after immunization with PBS and different polymersomes (e.g., BD21 (as defined later), $PDMS_{46}$-$PEO_{37}$ (marked in the figure just as "PDMS"), $PDMS_{46}$-$PEO_{37}$ with DSPE-PEG (distearoylphosphatidylethanolamine [DSPE] polyethylene glycol) as added lipid, polyethylene glycol-polylactic acid (PLA-PEG) with added Asolectin lipids (commercially available phospholipids from soybean) encapsulating either full length soluble PED spike protein (in the case of "BD21 with soluble S protein") or a S1 or S2 fragment thereof (in all other cases). From FIG. 10, it is evident that the groups of mice immunized with PBS sample do not show any virus neutralization, whereas all polymersome formulations show varying degree of virus neutralization regardless of whether they encapsulate the full length protein or a fragment thereof.
Figure 11:
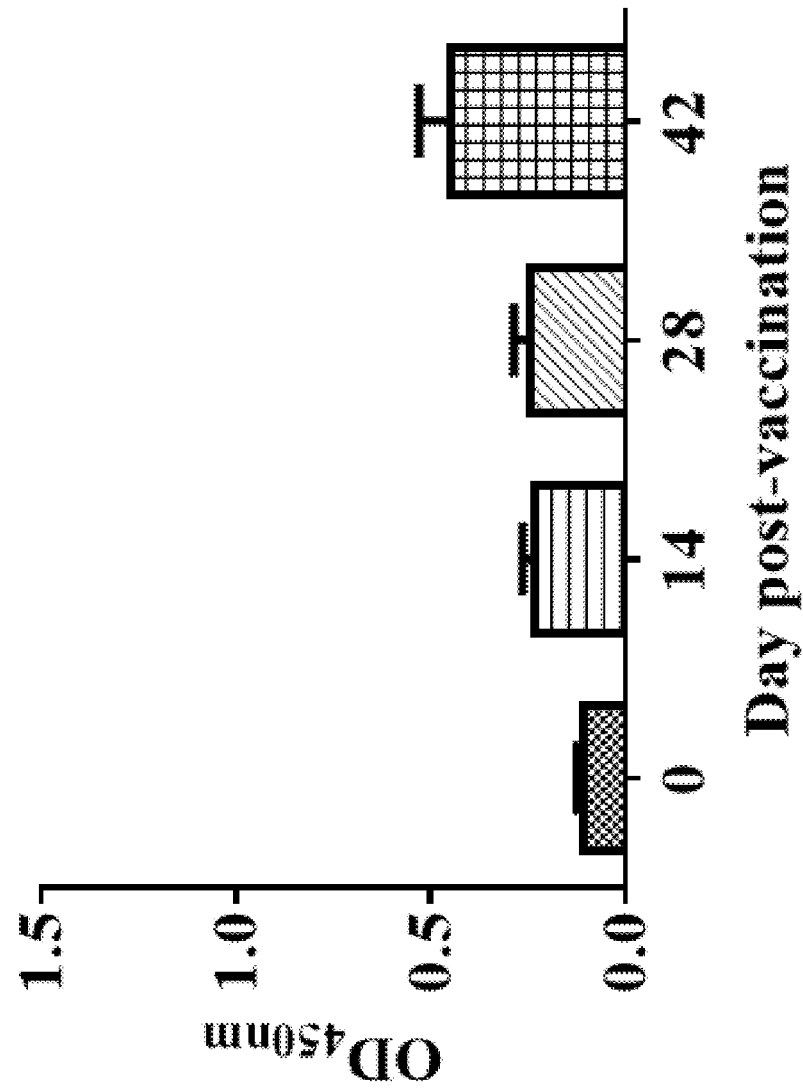
FIG. 11 shows IgA Antibody titers from swine immunised orally with ACM encapsulated PEDv S protein without the use of adjuvants. Titres are from faecal swabs.

Encapsulated PEDv Spike Protein and IgG, IgA and Virus Neutralisation Response of Example 6:

Mice were immunised with ACM encapsulated PEDv spike protein and boosted with a second dose after 21 days. Sera was collected from the final bleed and was used for ELISA. As can be seen in FIG. 8, antibodies that bind to SPIKE Protein coated on ELISA PLATE and the titers are of similar level to the animals vaccinated with killed virus in comparison with ACM vaccinated mice. Moreover, the sera were tested for their ability to neutralise the PEDV strain USA/Colorado/2013 (C0/13) through a conventional virus neutralisation experiment (FIG. 9). In here, it was observed that the virus neutralization occurs only for the sera from the mice immunized with ACM vaccine (i.e., ACM encapsulated PED Spike protein) while no neutralization was observed for the sera from the mice vaccinated with killed virus. Furthermore, different polymersomes (e.g., BD21, $PDMS_{46}$-$PEO_{37}$ (marked in FIG. 10 only as "PDMS"), $PDMS_{46}$-$PEO_{37}$/DSPE-PEG, PLA-PEG/Asolectin lipids) encapsulated with full length soluble protein and polymersomes mixture containing S1 and S2 region were immunized and the sera were tested for virus neutralization (FIG. 10). From FIG. 10, it is evident that the groups of mice immunized with PBS sample doesn't show any virus neutralization, whereas all other polymersome formulation shows varying degree of virus neutralization. Furthermore, when weaned pigs were orally vaccinated with ACM encapsulated PED SPIKE protein (after a prime on day 1 and a boost on day 14, an increase in specific IgA antibodies against the virus was observed from the faecal swabs collected and measured via ELISA, (see FIG. 11).

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of certain embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied herein may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

REFERENCES

Liu et al., Immune responses to vaccines delivered by encapsulation into and/or adsorption onto cationic lipid-PLGA hybrid nanoparticles, Journal of Controlled Release, 225 (2016): 230-239.

Hilbert et al., Biodegradable microspheres containing influenza A vaccine: immune response to mice, Vaccine 17 (1999): 1065-1073.

Miller et al., Adjuvant compositions and related methods, U.S. Pat. No. 9,636,397B2, Gerber et al., Adjuvant and vaccine compositions, US2015/0044242 A1.

Maji et al., A lipid based antigen delivery system efficiently facilitates MHC class-I Antigen Presentation in Dendritic Cells to Stimulate CD8+ T cells, Scientific Reports 6 (2016): 27206.

Moon et al., Interlayer-crosslinked multilamellar vesicles as synthetic vaccines for potent humoral and cellular responses, Nature Materials 10 (2011): 243-251.

May et al., "In Vitro Expressed GPCR Inserted in Polymersome Membranes for Ligand-Binding Studies" (2013) Angew. Chem. Int. Ed., 52, pages 749-753Kuai et al., Designer vaccine nanodiscs for personalized cancer immunotherapy, Nat Mater. (2017) 16(4):489-496.

Luo et al., A STING-activating nanovaccine for cancer immunotherapy, Nat Nanotechnol. (2017) 12(7):648-654.

Quer et al, "Polymersomes enhance the immunogenicity of influenza subunit vaccine", POLYMER CHEMISTRY, GB, (2012), vol. 2, no. 7, page 1482

Nallani et al., Method for eliciting an immune response to an immunogen, WO2014/077781A1.

Nallani et al., Proteopolymersomes: In vitro production of a membrane protein in polymersome membranes (2011), Biointerphases, 6(4), pages 153-157.

Neil et al, A Novel Method for the Encapsulation of Biomolecules into Polymersomes via Direct Hydration, Langmuir (2009), 25(16), 9025-9029.

Rameez et al. Large Scale Production of Vesicles by Hollow Fiber Extrusion: A Novel Method for Generating Polymersome Encapsulated Hemoglobin Dispersions Langmuir (2010) 26 (7), pp 5279-5285 Stano et al., Tunable T cell immunity towards a protein antigen using polymersomes vs. solid-core nanoparticles, Biomaterials 34 (2013): 4339-4346.

Fu et al., Multicompartmentalized polymersomes for selective encapsulation of biomacromolecules, Chemical Communication, 2011, 47, 2862-2864.

Lim. S. K, et al., Spontaneous formation of nanometer scale tubular vesicles in aqueous mixtures of lipid and block copolymer amphiphiles, Soft Matter 2017, 1107-1115.

Scott et al., Dendritic cell activation and T cell priming with adjuvant- and antigen-loaded oxidation-sensitive polymersomes, Biomaterials 33 (2012) 6211e6

What is claimed is:

1. An oxidation-stable polymersome comprising:
a soluble polypeptide antigen encapsulated within a lumen of the polymersome formed by an enclosing polymersome membrane,
wherein
said polymersome has a diameter ranging from about 100 nm to about 1 μm,
said polymersome membrane comprises a poly(butadiene)-poly(ethylene oxide) (PB-PEO) diblock copolymer amphiphilic polymer, wherein said PB-PEO diblock copolymer comprises a poly(butadiene)$_{21}$-poly(ethylene oxide)$_{14}$ diblock, and
said polymersome is capable of eliciting a CD8(+) T cell-mediated immune response to the polypeptide antigen.

2. The polymersome according to claim 1, wherein said polypeptide antigen comprises a soluble portion of a membrane protein (MP) or a membrane-associated peptide (MAP).

3. The polymersome according to claim 1, wherein said polymersome is capable of releasing its content comprising said polypeptide antigen in an oxidation-independent manner and triggering CD8(+) T cell-mediated immune response.

4. The polymersome according to claim 1, wherein said polypeptide antigen comprises a polypeptide which is at least 60% or more identical to a polypeptide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NOs: 12-14.

5. The polymersome according to claim 1, wherein the polymersome is in the form of a collection of polymersomes, wherein the mean diameter of the collection of polymersomes is in the range of about 100 nm to about 1 μm.

6. The polymersome according to claim 1, wherein said polypeptide antigen is selected from a group consisting of: i) a self-antigen, ii) a non-self antigen, iii) a non-self immunogen and iv) a self-immunogen.

7. The polymersome according to claim 1, wherein said polypeptide antigen is selected from the group consisting of:
i) Influenza hemagglutinin (HA) selected from the group consisting of: SEQ ID NO: 5, SEQ ID NO: 6, SEQ ID NO: 7 and SEQ ID NO: 8;
ii) Swine Influenza hemagglutinin (HA) of SEQ ID NO: 6;
iii) Ovalbumin (OVA) of SEQ ID NO: 4;
iv) B16 peptide selected from the group consisting of: SEQ ID NO: 9, SEQ ID NO: 10 and SEQ II) NO: II;
v) MC38 peptide selected from the group consisting of: SEQ ID NO: 1, SEQ ID NO: 2 and SEQ ID NO: 3;
vi) B16 and MC38 peptides, wherein said peptides are independently selected the groups: i) SEQ ID NOs: 1-3 and ii) SEQ ID NOs: 9-11;
vii) Porcine epidemic diarrhea virus SPIKE protein and a soluble fragment thereof, wherein said fragment is of SEQ ID NOs: 12, 13 or 14.

8. The polymersome according to claim 1, wherein said polymersome has a diameter of about 120 nm or 140 nm.

9. The polymersome according to claim 1, wherein said PB-PEO diblock copolymer consists of diblock copolymer PBD$_{21}$-PEO$_{14}$.

10. The polymersome according to claim 1, wherein the membrane of the polymersome further comprises at least one lipid.

11. The polymersome of claim 10, wherein the lipid is a synthetic lipid, a natural lipid or a combination of a synthetic and natural lipid.

12. The polymersome of claim 11, wherein the lipid is selected from the group consisting of distearoylphosphatidylethanolamine polyethylene glycol, asolectin, 1,2-dioleoyl-3-trimethylammonium-propane and 1-palmitoyl-2-oleoyl-sn-glycero-3-phospho-L-serine.

13. A vaccine comprising the polymersome according to claim 1, and further comprising a pharmaceutically accepted excipient or carrier.

* * * * *